United States Patent
Cohen et al.

(10) Patent No.: US 9,207,237 B2
(45) Date of Patent: *Dec. 8, 2015

(54) SYSTEMS, METHODS, AND WORKFLOWS FOR OPTOGENETICS ANALYSIS

(71) Applicant: President and Fellows of Harvard College, Cambridge, MA (US)

(72) Inventors: Adam E. Cohen, Cambridge, MA (US); Joel Kralj, Somerville, MA (US); Adam D. Douglass, Salt Lake City, UT (US); Daniel Hochbaum, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/303,178

(22) Filed: Jun. 12, 2014

(65) Prior Publication Data

US 2014/0295413 A1    Oct. 2, 2014

Related U.S. Application Data

(63) Continuation-in-part of application No. 13/818,432, filed as application No. PCT/US2011/048793 on Aug. 23, 2011.

(60) Provisional application No. 61/412,972, filed on Nov. 12, 2010, provisional application No. 61/376,049, filed on Aug. 23, 2010.

(51) Int. Cl.
| | |
|---|---|
| *C12M 1/34* | (2006.01) |
| *G01N 33/566* | (2006.01) |
| *G01N 33/543* | (2006.01) |
| *A61K 49/00* | (2006.01) |

(52) U.S. Cl.
CPC .......... *G01N 33/566* (2013.01); *A61K 49/0017* (2013.01); *A61K 49/0097* (2013.01); *G01N 33/54373* (2013.01); *G01N 2333/705* (2013.01)

(58) Field of Classification Search
CPC .................................................. G01N 33/566
See application file for complete search history.

(56) References Cited

U.S. PATENT DOCUMENTS

| | | | |
|---|---|---|---|
| 5,290,699 A | 3/1994 | Oesterhelt et al. | |
| 5,661,035 A | 8/1997 | Tsien et al. | |
| 5,925,523 A | 7/1999 | Dove et al. | |
| 6,107,066 A | 8/2000 | Tsien et al. | |
| 6,200,759 B1 | 3/2001 | Dove et al. | |
| 6,243,197 B1 | 6/2001 | Schalz | |
| 6,885,492 B2 | 4/2005 | DeSimone et al. | |
| 6,898,004 B2 | 5/2005 | Shimizu et al. | |
| 6,972,892 B2 | 12/2005 | DeSimone et al. | |
| 6,991,910 B2 | 1/2006 | Adorante et al. | |
| 7,459,333 B2 | 12/2008 | Richards et al. | |
| 7,560,709 B2 | 7/2009 | Kimura et al. | |
| 7,736,897 B2 | 6/2010 | Tao et al. | |
| 7,964,853 B2 | 6/2011 | Araya | |
| 8,202,699 B2 | 6/2012 | Hegemann et al. | |
| 8,401,609 B2 | 3/2013 | Deisseroth et al. | |
| 8,532,398 B2 | 9/2013 | Filkins et al. | |
| 8,562,658 B2 | 10/2013 | Shoham et al. | |
| 8,580,937 B2 | 11/2013 | Spudich et al. | |
| 8,603,790 B2 | 12/2013 | Deisseroth et al. | |
| 8,617,876 B2 | 12/2013 | Farrar et al. | |
| 8,647,870 B2 | 2/2014 | Hegemann et al. | |
| 8,716,447 B2 | 5/2014 | Deisseroth et al. | |
| 2002/0021490 A1 | 2/2002 | Kasahara et al. | |
| 2005/0202398 A1 | 9/2005 | Hegemann et al. | |
| 2009/0142852 A1 | 6/2009 | Friedrich et al. | |
| 2009/0229669 A1 | 9/2009 | Birge et al. | |
| 2009/0268511 A1 | 10/2009 | Birge et al. | |
| 2011/0165681 A1 | 7/2011 | Boyden et al. | |
| 2011/0200568 A1 | 8/2011 | Ikeda et al. | |
| 2013/0170026 A1 | 7/2013 | Cohen et al. | |
| 2013/0224756 A1 | 8/2013 | Cohen et al. | |
| 2014/0093907 A1 | 4/2014 | Miller et al. | |

FOREIGN PATENT DOCUMENTS

| | | |
|---|---|---|
| EP | 2 023 127 A1 | 2/2009 |
| EP | 2 112 510 A1 | 10/2009 |
| WO | WO 01/59446 A2 | 8/2001 |
| WO | WO 01/83701 A2 | 11/2001 |
| WO | WO 2004/063326 A2 | 7/2004 |
| WO | WO 2007/019398 A1 | 2/2007 |

(Continued)

OTHER PUBLICATIONS

Invitation to Pay Additional Fees for PCT/US2012/066303, mailed Mar. 21, 2013.
International Search Report and Written Opinion for PCT/US2012/066303, mailed May 28, 2013.
International Preliminary Report on Patentability for PCT/US2012/066303, mailed Jun. 5, 2014.
International Search Report and Written Opinion for PCT/US2011/048793, mailed Dec. 13, 2011.
International Preliminary Report on Patentability for PCT/US2011/048793, Mar. 7, 2013.
GenBank Submission; NIH/NCBI, Accession No. AAY82897. Ewers et al., Jun. 1, 2006. 1 page.
GenBank Submission; NIH/NCBI, Accession No. NC_010364.1. Pfeiffer et al., Jun. 10, 2013. 1 page.
GenBank Submission; NIH/NCBI, Accession No. P29563. Uegaki et al., Oct. 29, 2014. 3 pages.
GenBank Submission; NIH/NCBI, Accession No. P69051. Sugiyama et al., Oct. 29, 2014. 3 pages.

(Continued)

*Primary Examiner* — Albert Navarro
(74) *Attorney, Agent, or Firm* — Wolf, Greenfield & Sacks, P.C.

(57) ABSTRACT

The invention provides methods for characterizing cellular physiology by incorporating into an electrically excitable cell an optical reporter of, and an optical actuator of, electrical activity. A signal is obtained from the optical reporter in response to a stimulation of the cell. Either or both of the optical reporter and actuator may be based on genetically-encoded rhodopsins incorporated into the cell. The invention provides all optical methods that may be used instead of, or as a complement to, traditional patch clamp technologies and that can provide rapid, accurate, and flexible assays of cellular physiology.

64 Claims, 26 Drawing Sheets

(56) References Cited

FOREIGN PATENT DOCUMENTS

| WO | WO 2007/131180 A2 | 11/2007 |
|---|---|---|
| WO | WO 2008/149055 A1 | 12/2008 |
| WO | WO 2010/027446 A2 | 3/2010 |
| WO | WO 2010/056970 A2 | 5/2010 |
| WO | WO 2012/027358 A1 | 3/2012 |

OTHER PUBLICATIONS

GenBank Submission; NIH/NCBI, Accession No. P96787. Ihara et al., Oct. 29, 2014. 3 pages.

GenBank Submission; NIH/NCBI, Accession No. Z35086.1. Seidel et al., Sep. 9, 2004. 2 pages.

GenBank Submission; NIH/NCBI, Accession No. AAG01180. Idnurm et al., Mar. 21, 2001. 1 page.

GenBank Submission; NIH/NCBI, Accession No. AAG42454. Wang et al., Dec. 26, 2000. 1 page.

GenBank Submission; NIH/NCBI, Accession No. AF349981. Béjà et al., May 11, 2004. 1 page.

GenBank Submission; NIH/NCBI, Accession No. AF349983. Béjà et al., May 11, 2004. 1 page.

GenBank Submission; NIH/NCBI, Accession No. BAA06678. Tateno et al., Feb. 7, 1999. 1 page.

GenBank Submission; NIH/NCBI. Accession No. GU045593.1. Chow et al., Jan. 6, 2010. 1 page.

GenBank Submission; NIH/NCBI, Accession No. HM367071. Han et al., Apr. 13, 2011. 1 page.

GenBank Submission; NIH/NCBI. Accession No. M11720.1. Dunn et al., Apr. 26, 1993. 1 page.

Akemann et al., Imaging neural circuit dynamics with a voltage-sensitive fluorescent protein. J Neurophysiol. Oct. 2012;108(8):2323-37. doi: 10.1152/jn.00452.2012. Epub Jul. 18, 2012.

Akemann et al., Two-photon voltage imaging using a genetically encoded voltage indicator. Sci Rep. 2013;3:2231. doi: 10.1038/srep02231.

Ataka et al., A genetically targetable fluorescent probe of channel gating with rapid kinetics. Biophys J. Jan. 2002;82(1 Pt 1):509-16.

Atasoy et al., A Flex switch targets Channelrhodopsin-2 to multiple cell types for imaging and long-range circuit mapping. J Neurosci. Jul. 9, 2008;28(28):7025-30. doi: 10.1523/JNEUROSCI.1954-08.2008.

Baker et al., Genetically encoded fluorescent sensors of membrane potential. Brain Cell Biol. Aug. 2008;36(1-4):53-67.

Baker et al., Three fluorescent protein voltage sensors exhibit low plasma membrane expression in mammalian cells. J Neurosci Methods. Mar. 30, 2007;161(1):32-38.

Barondeau et al., Mechanism and energetics of green fluorescent protein chromophore synthesis revealed by trapped intermediate structures. Proc Natl Acad Sci U S A. Oct. 14, 2003;100(21):12111-6. Epub Oct. 1, 2003.

Bean, The action potential in mammalian central neurons. Nat Rev Neurosci. Jun. 2007;8(6):451-65.

Béjà et al., Proteorhodopsin phototrophy in the ocean. Nature. Jun. 14, 2001;411(6839):786-9.

Béjà et al., Bacterial rhodopsin: evidence for a new type of phototrophy in the sea. Science. Sep. 15, 2000;289(5486):1902-6.

Bergo et al., Conformational changes detected in a sensory rhodopsin II-transducer complex. J Biol Chem. Sep. 19, 2003;278(38):36556-62.

Bernstein et al., Optogenetics and thermogenetics: technologies for controlling the activity of targeted cells within intact neural circuits. Curr Opin Neurobiol. Feb. 2012;22(1):61-71. doi: 10.1016/j.conb.2011.10.023. Epub Nov. 24, 2011.

Boyden et al., Millisecond-timescale, genetically targeted optical control of neural activity. Nat Neurosci. Sep. 2005;8(9):1263-8. Epub Aug. 14, 2005.

Brack et al., Picosecond time-resolved absorption and fluorescence dynamics in the artificial bacteriorhodopsin pigment BR6.11. Biophys J. Aug. 1993;65(2):964-72.

Canepari et al., Combining calcium imaging with other optical applications. Cold Spring Harbor Protocols. 2013. pbd. Top066167.

Cans et al., Positioning Lipid Membrane Domains in Giant Vesicles by Micro-organization of Aqueous Cytoplasm Mimic. J. Am. Chem. Soc., 2008;130(23):7400-7406.

Cao et al., Genetically targeted optical electrophysiology in intact neural circuits. Cell. Aug. 15, 2013;154(4):904-13. doi: 10.1016/j.cell.2013.07.027. Epub Aug. 8, 2013.

Cardin et al., Targeted optogenetic stimulation and recording of neurons in vivo using cell-type-specific expression of Channelrhodopsin-2. Nat. Protoc. Feb. 2010;5(2):247-54. doi: 10.1038/nprot.2009.228. Epub Jan. 21, 2010.

Carlson et al., Circular permutated red fluorescent proteins and calcium ion indicators based on mCherry. Protein Eng Des Sel. Dec. 2013;26(12):763-72. doi: 10.1093/protein/gzt052. Epub Oct. 22, 2013.

Chanda et al., A hybrid approach to measuring electrical activity in genetically specified neurons. Nat Neurosci. Nov. 2005;8(11):1619-26. Epub Oct. 2, 2005.

Chen et al., Paired-pulse depression of unitary quantal amplitude at single hippocampal synapses. Proc Natl Acad Sci U S A. Jan. 27, 2004;101(4):1063-8. Epub Jan. 13, 2004.

Chen et al., Ultrasensitive fluorescent proteins for imaging neuronal activity. Nature. Jul. 18, 2013;499(7458):295-300. doi: 10.1038/nature12354.

Chow et al., High-performance genetically targetable optical neural silencing by light-driven proton pumps. Nature. Jan. 7, 2010;463(7277):98-102.

Chung et al., Diagnostic potential of laser-induced autofluorescence emission in brain tissue. J Korean Med Sci. Apr. 1997;12(2):135-42.

Depry et al., Multiplexed visualization of dynamic signaling networks genetically encoded fluorescent protein-based biosensors. Pflugers Arch. Mar. 2013;465(3):373-81. doi: 10.1007/s00424-012-1175-y. Epub Nov. 9, 2012.

Derossi et al., Cell internalization of the third helix of the Antennapedia homeodomain is receptor-independent. J. Biol Chem. Jul. 26, 1996;271(30):18188-93.

Diester et al., An optogenetic toolbox designed for primates. Nat Neurosci. Mar. 2011;14(3):387-97. doi: 10.1038/nn.2749. Epub Jan. 30, 2011.

Dioumaev et al., Proton transfers in the photochemical reaction cycle of proteorhodopsin. Biochemistry.Apr. 30, 2002;41(17):5348-58.

Dioumaev et al., Proton transport by proteorhodopsin requires that the retinal Schiff base counterion Asp-97 be anionic. Biochemistry. Jun. 3, 2003;42(21):6582-7.

Dooley et al., Imaging dynamic redox changes in mammalian cells with green fluorescent protein indicators. J Biol Chem. May 21, 2004;279(21):22284-93. Epub Feb. 25, 2004.

Enami et al., Crystal structures of archaerhodopsin-1 and -2: Common structural motif in archaeal light-driven proton pumps. J Mol Biol. May 5, 2006;358(3):675-85.

Flock et al., Optical properties of Intralipid: a phantom medium for light propagation studies. Lasers Surg Med. 1992;12(5):510-9.

Friedrich et al., Proteorhodopsin is a light-driven proton pump with variable vectoriality. J Mol Biol. Aug. 30, 2002;321(5):821-38.

Fromherz et al., ANNINE-6plus, a voltage-sensitive dye with solubility, strong membrane binding and high sensitivity. Eur. Biophys J. Apr. 2008;37(4):509-14.

Furuta et al., Brominated 7-hydroxycoumarin-4-ylmethyls: photolabile protecting groups with biologically useful cross-sections for two photon photolysis. Proc Natl Acad Sci U S A. Feb. 16, 1999;96(4):1193-200.

Gabriel et al., Direct observation in the millisecond time range of fluorescent molecule asymmetrical interaction with the electropermeabilized cell membrane. Biophys J. Nov. 1997;73(5):2630-7.

Giovannoni et al., Proteorhodopsin in the ubiquitous marine bacterium SAR11. Nature. Nov. 3, 2005;438(7064):82-5.

Gong et al., Imaging neural spiking in brain tissue using FRET-opsin protein voltage sensors. Nat Commun. Apr. 22, 2014;5:3674. doi: 10.1038/ncomms4674.

Gradinaru et al., Molecular and cellular approaches for diversifying and extending optogenetics. Cell. Apr. 2, 2010;141(1):154-65.

(56) References Cited

OTHER PUBLICATIONS

Hochbaum et al., All-optical electrophysiology in mammalian neurons using engineered microbial rhodopsins. Nat Methods. Jun. 22, 2014. doi: 10.1038/nmeth.3000. [Epub ahead of print].
Hoffmann et al., Photoactive mitochondria: in vivo transfer of a light-driven proton pump into the inner mitochondrial membrane of Schizosaccharomyces pombe. Proc Natl Acad Sci U S A. Sep. 27, 1994;91(20):9367-71.
Hou et al., Temporal dynamics of microbial rhodopsin fluorescence reports absolute membrane voltage. Biophys J. Feb. 4, 2014;106(3):639-48. doi: 10.1016/j.bpj.2013.11.4493.
Huggins et al., Optimal experimental design for sampling voltage on dendritic trees in the low-SNR regime. J Comput Neurosci. Apr. 2012;32(2):347-66. doi: 10.1007/s10827-011-0357-5. Epub Aug. 23, 2011.
Huys et al., Efficient estimation of detailed single-neuron models. J Neurophysiol. Aug. 2006;96(2):872-90. Epub Apr. 19, 2006.
Ichas et al., Mitochondria are excitable organelles capable of generating and conveying electrical and calcium signals. Cell. Jun. 27, 1997;89(7):1145-53.
Ihara et al., Evolution of the archaeal rhodopsins: evolution rate changes by gene duplication and functional differentiation. J Mol Biol. Jan. 8, 1999;285(1):163-74.
Jin et al., Single action potentials and subthreshold electrical events imaged in neurons with a fluorescent protein voltage probe. Neuron. Sep. 6, 2012;75(5):779-85. doi: 10.1016/j.neuron.2012.06.040.
Kirkton et al., Engineering biosynthetic excitable tissues from unexcitable cells for electrophysiological and cell therapy studies. Nat Commun. 2011;2:300. doi: 10.1038/ncomms1302.
Klapoetke et al., Independent optical excitation of distinct neural populations. Nat Methods. Mar. 2014;11(3):338-46. doi: 10.1038/nmeth.2836. Epub Feb. 9, 2014.
Kleinlogel et al., A gene-fusion strategy for stoichiometric and co-localized expression of light-gated membrane proteins. Nat Methods. Nov. 6, 2011;8(12):1083-8. doi: 10.1038/nmeth.1766.
Knöpfel et al., Toward the second generation of optogenetic tools. J Neurosci. Nov. 10, 2010;30(45):14998-5004.
Kochendoerfer et al., How color visual pigments are tuned. Trends Biochem Sci. Aug. 1999;24(8):300-5.
Kolodner et al., Electric-field-induced Schiff-base deprotonation in D85N mutant bacteriorhodopsin. Proc Natl Acad Sci U S A. Oct. 15, 1996;93(21):11618-21.
Kralj et al., Electrical spiking in *Escherichia coli* probed with a fluorescent voltage-indicating protein. Science. Jul. 15, 2011;333(6040):345-8.
Kralj et al., Optical recording of action potentials in mammalian neurons using a microbial rhodopsin. Nat Methods. Nov. 27, 2011;9(1):90-5. doi: 10.1038/nmeth.1782.
Kramer et al., New photochemical tools for controlling neuronal activity. Curr Opin Neurobiol. Oct. 2009;19(5):544-52. doi: 10.1016/j.conb.2009.09.004. Epub Oct. 12, 2009.
Krauthamer et al., Action potential-induced fluorescence changes resolved with an optical fiber carrying excitation light. J Fluoresc. Dec. 1991;1(4):207-13.
Krylova et al., A versatile, bar-coded nuclear marker/reporter for live cell fluorescence and multiplexed high content imaging. PLoS One. May 14, 2013;8(5):e63286. doi: 10.1371/journal.pone.0063286. Print 2013.
Kuner et al., A genetically encoded ratiometric indicator for chloride: capturing chloride transients in cultured hippocampal neurons. Neuron. Sep. 2000;27(3):447-59.
Lam et al., Improving FRET dynamic range with bright green and red fluorescent proteins. Nat Methods. Oct. 2012;9(10):1005-12. doi: 10.1038/nmeth.2171. Epub Sep. 9, 2012.
Lanyi, Proton translocation mechanism and energetics in the light-driven pump bacteriorhodopsin. Biochim Biophys Acta. Dec. 7, 1993;1183(2):241-61.
Lanyi., Bacteriorhodopsin. Annu Rev Physiol. 2004;66:665-88.
Lenz et al., First steps of retinal photoisomerization in proteorhodopsin. Biophys J. Jul. 1, 2006;91(1):255-62.
Liang et al., Patterned Photostimulation with Digital Micromirror Devices to Investigate Dendritic Integration Across Branch Points. J Vis Exp. 2011;40:e2003. Video Article.
Liem et al., The patch clamp technique. Neurosurgery. Feb. 1995;36(2):382-92.
Lin et al., Brain tumor demarcation using optical spectroscopy; an in vitro study. J Biomed Opt. Apr. 2000;5(2):214-20.
Lin et al., Characterization of engineered channelrhodopsin variants with improved properties and kinetics. Biophys J. Mar. 4, 2009;96(5):1803-14. doi: 10.1016/j.bpj.2008.11.034.
Lundby et al., Engineering of a genetically encodable fluorescent voltage sensor exploiting fast Ci-VSP voltage-sensing movements. PLoS One. Jun. 25, 2008;3(6):e2514. doi: 10.1371/journal.pone.0002514.
Ma et al., Role of ER export signals in controllling surface potassium channel numbers. Science. Jan. 12, 2001;291(5502):316-9.
MacLaurin et al., Mechanism of voltage-sensitive fluorescence in a microbial rhodopsin. Proc Natl Acad Sci U S A. Apr. 9, 2013;110(15):5939-44. doi: 10.1073/pnas.1215595110. Epub Mar. 25, 2013.
Man et al., Diversification and spectral tuning in marine proteorhodopsins. EMBO J. Apr. 15, 2003;22(8):1725-31.
Martinac et el., Ion channels in microbes. Physiol Rev. Oct. 2008;88(4):1449-90.
Maruyama et al., Detecting cell using non-negative matrix factorization on calcium imaging data. Neutral Netw. Jul. 2014;55:11-9. doi: 10.1016/j.neunet.2014.03.007. Epub Mar. 24, 2014.
Marvin et al., An optimized fluorescent probe for visualizing glutamate neurotransmission. Nat Methods. Feb. 2013;10(2):162-70. doi: 10.1038/nmeth.2333. Epub Jan. 13, 2013.
Mattis et al., Principles for applying optogenetic tools derived from direct comparitive analysis of microbial opsins. Nat Methods. Dec. 18, 2011;9(2):159-72. doi: 10.1038/nmeth.1808.
Melkonian et al., A light and electron microscopic study of Scherffelia dubia, a new member of the scaly green flagellates (Prasinophyceae). Nord J Bot. 1986;6(2):235-256.
Miller et al., Optically monitoring voltage in neurons by photo-induced electron transfer through molecular wires. Proc Natl Acad Sci U S A. Feb. 7, 2012;109(6):2114-9. doi: 10.1073/pnas.1120694109. Epub Jan. 24, 2012.
Mogi et al., Aspartic acid substitutions affect proton translocation by bacteriorhodopsin. Proc Natl Acad Sci U S A. Jun. 1988;85(12):4148-52.
Molokanova et al., Bright future of optical assays for ion channel drug discovery. Drug Discov Today. Jan. 2008;13(1-2):14-22.
Mukamel et al., Automated analysis of cellular signals from large-scale calcium imaging data. Neuron. Sep. 24, 2009;63(6):747-60. doi: 10.1016/j.neuron.2009.08.009.
Murata et al., Phosphoinositide phosphate activity coupled to an intrinsic voltage sensor. Nature. Jun. 30, 2005;435(7046):1239-43. Epub May 18, 2005.
Mutoh et al., Genetically engineered fluorescent voltage reporters. ACS Chem Neurosci. Aug. 15, 2012;3(8):585-92. doi: 10.1021/cn300041b. Epub Jun. 6, 2012.
Mutoh et al., Spectrally-resolved response properties of the three most advanced FRET based fluorescent protein voltage probes, PLoS One. 2009;4(2):e4555.
Nagel et al., Light activation of channelrhodopsin-2 in excitable cells of Caenorhabditis elegans triggers rapid behavioral responses. Curr Biol. Dec. 20, 2005;15(24):2279-84.
Neutze et al., Bacteriorhodopsin: a high-resolution structural view of vectorial proton transport. Biochim Biophys Acta. Oct. 11, 2002;1565(2):144-67.
Oldach et al., Genetically encoded fluorescent biosensors for live-cell visualization of protein phosphorylation. Chem Biol. Feb. 20, 2014;21(2):186-97. doi: 10.1016/j.chembiol.2013.12.012. Epub Jan. 30, 2014.
Park et al., Screening fluorescent voltage indicators with spontaneously spiking HEK cells. PLoS One. Dec. 31, 2013;8(12):e85221. doi: 10.1371/journal.pone.0085221. eCollection 2013.
Peron et al., From cudgel to scalpel: toward precise neural control with optogenetics. Nat Methods. Jan. 2011;8(1):30-4. doi: 10.1038/nmeth.f.325. Epub Dec. 20, 2010.

(56) References Cited

OTHER PUBLICATIONS

Perron et al., Second and third generation voltage-sensitive fluorescent proteins for monitoring membrane potential. Front Mol Neurosci. Jun. 22, 2009;2:5. doi: 10.3389/neuro.02.005.2009. eCollection 2009.

Popovic et al., The spatio-temporal characteristics of action potential initiation in layer 5 pyramidal neurons: a voltage imaging study. J Physiol. Sep. 1, 2011;589(Pt 17):4167-87. doi: 10.1113/jphysiol. 2011.209015. Epub Jun. 13, 2011.

Przybylo et al., Fluorescence techniques for determination of the membrane potentials in high throughput screening. J Fluoresc. Nov. 2010;20(6):1139-57. doi: 10.1007/s10895-010-0665-6.

Pucihar et al., Measuring the induced membrane voltage with Di-8-ANEPPS. J Vis Exp. Nov. 19, 2009;(33). pii: 1659. doi: 10.3791/1659. Video Article.

Rousso et al., pKa of the protonated Schiff base and aspartic 85 in the bacteriorhodopsin binding site is controlled by a specific geometry between the two residues. Biochemistry. Sep. 19, 1995;34(37):12059-65.

Sakai et al., Design and characterization of a DNA-encoded, voltage-sensitive fluorescent protein. Eur J Neurosci. Jun. 2001;13(12):2314-8.

San Martin et al., Imaging mitochondrial flux in single cells with a FRET sensor for pyruvate.PLoS One. Jan. 21, 2014;9(1):e85780. doi: 10.1371/journal.pone.0085780. eCollection 2014.

Scanziani et al., Electrophysiology in the age of light. Nature Oct. 15, 2009;461(7266):930-9. doi: 10.1038/nature08540.

Schoenenberger et al., Optimizing the spatial resolution of Channelrhodopsin-2 activation. Brain Cell Biol. Aug. 2008;36(1-4):119-27. doi: 10.1007/s11068-008-9025-8. Epub Jul. 25, 2008.

Shaner et al., A guide to choosing fluorescent proteins. Nat Methods. Dec. 2005;2(12):905-9.

Sheves et al., Controlling the pKa of the bacteriorhodopsin Schiff base by use of artificial retinal analogues. Proc Natl. Acad Sci. U S A. May 1986;83(10):3262-6.

Siegel et al., A genetically encoded optical probe of membrane voltage. Neuron. Oct. 1997;19(4):735-41.

Sineshchekov et al., Light-induced intramolecular charge movements in microbial rhodopsins in intact *E. coli* cells. Photochem Photobiol Sci. Jun. 2004;3(6):548-54. Epub Mar. 18, 2004.

Sjulson et al., Rational optimization and imaging in vivo of a genetically encoded optical voltage reporter. J Neurosci. May 21, 2008;28(21):5582-93.

Soppa et al., Bacteriorhodopsin mutants of Halobacterium sp. GRB. II. Characterization of mutants. J Biol Chem. Aug. 5, 1989;264(22):13049-56.

St-Pierre et al., High-fidelity optical reporting of neuronal electrical activity with an ultrafast fluorescent voltage sensor. Nat Neurosci. Jun. 2014;17(6):884-9. doi: 10.1038/nn.3709. Epub Apr. 22, 2014.

Subramaniam et al., Protonation state of Asp (Glu)-85 regulates the purple-to-blue transition in bacteriorhodopsin mutants Arg-82-Ala and Asp-85-Glu: the blue form is inactive in proton translocation. Proc Natl Acad Sci U S A. Feb. 1990;87(3):1013-7.

Takahashi et al., Light-addressed single-neuron stimulation in dissociated neuronal cultures with sparse expression of ChR2. Biosystems. Feb. 2012;107(2):106-12. doi: 10.1016/j.biosystems. 2011.10.002, Epub Oct. 14, 2011.

Tantama et al., Imaging energy status in live cells with a fluorescent biosensor of the intracellular ATP-to-ADP ratio. Nat Commun. 2013;4:2550. doi: 10.1038/ncomms3550.

Tateno et al., The novel ion pump rhodopsins from Haloarcula form a family independent from both the bacteriorhodopsin and archaerhodopsin families/tribes. Arch Biochem Biophys. Nov. 15, 1994;315(1):127-32.

Tsuda et al., Probing the function of neuronal populations: combining micromirror-based optogenetic photostimulation with voltage-sensitive dye imaging. Neurosci Res. Jan. 2013;75(1):76-81. doi: 10.1016/j.neures.2012.11.006. Epub Dec. 17, 2012.

Venkatachalam et al., Flash memory: photochemical imprinting of neuronal action potentials onto a microbial rhodopsin. J Am Chem Soc. Feb. 12, 2014;136(6):2529-37. doi: 10.1021/ja411338t. Epub Jan. 27, 2014.

Vogt et al., Combining membrane potential imaging with L-glutamate or GABA photorelease. PLoS One. 2011;6(10):e24911. doi: 10.1371/journal.pone.0024911. Epub Oct. 11, 2011.

Wachter., The family of GFP-like proteins: structure, function, photophysics and biosensor applications. Introduction and perspective. Photochem Photobiol. Mar.-Apr. 2006;82(2):339-44.

Wang et al., Laser-evoked synaptic transmission in cultured hippocampal neurons expressing channelrhodopsin-2 delivered by adeno-associated virus. J Neurosci Methods. Oct. 15, 2009;183(2):165-75. doi: 10.1016/j.jneumeth.2009.06.024. Epub Jun. 26, 2009.

Wardill et al., A neuron-based screening platform for optimizing genetically-encoded calcium indicators. PLoS One. Oct. 14, 2013;8(10):e77728. doi: 10.1371/journal.pone.0077728. eCollection 2013.

Waschuk et al., Leptosphaeria rhodopsin: bacteriorhodopsin-like proton pump from a eukaryote. Proc Natl Acad Sci U S A. May 10, 2005;102(19):6879-83. Epub Apr. 28, 2005.

Williams et al., Computational optogenetics: empirically-derived voltage- and light-sensitive channelrhodopsin-2 model. PLoS Comput Biol. 2013;9(9):e1003220. doi: 10.1371/journal.pcbi. 1003220. Epub Sep. 12, 2013.

Wu et al., Improved orange and red $Ca^{2+}$ indicators and photophysical considerations for optogenetic applications. ACS Chem Neurosci. Jun. 19, 2013;4(6):963-72. doi: 10.1021/cn400012b. Epub Mar. 19, 2013.

Yan et al., Palette of fluorinated voltage-sensitive hemicyanine dyes. Proc Natl Acad Sci U S A. Dec. 11, 2012;109(50):20443-8. doi: 10.1073/pnas.1214850109. Epub Nov. 20, 2012.

Yizhar et al., Optogenetics in neural systems. Neuron. Jul. 14, 2011;71(1):9-34. doi: 10.1016/j.neuron.2011.06.004.

Zhao et al., An expanded pallete of genetically encoded $Ca^{2+}$ indicators. Science. Sep. 30, 2011;333(6051):1888-91. doi: 10.1126/science.1208592. Epub Sep. 8, 2011.

Zhao et al., Molecular evolution by staggered extension process (StEP) in vitro recombination. Nat Biotechnol. Mar. 1998;16(3):258-61.

SYSTEMS, METHODS, AND WORKFLOWS FOR OPTOGENETICS ANALYSIS

CROSS-REFERENCE TO RELATED APPLICATION

This application is a continuation-in-part of U.S. patent application, U.S. Ser. No. 13/818,432, filed May 13, 2013, which is a national stage filing under 35 U.S.C. §371 of international PCT application, PCT/US2011/048793, filed Aug. 23, 2011, which claims priority under 35 U.S.C. §119(e) to U.S. provisional patent applications, U.S. Ser. No. 61/376,049, filed Aug. 23, 2010 and U.S. Ser. No. 61/412,972, filed Nov. 12, 2010, the contents of each of which are incorporated herein by reference in their entirety.

FIELD OF INVENTION

The invention relates to methods of characterizing the electrophysiology of cells.

BACKGROUND

In the late 1700s, Luigi Galvani observed a frog carcass move in response to electric stimulus. This led to the insight that cells are affected by and can transmit electrical signals. Two hundred years later, the patch clamp provided a way to study the electrical physiology of cells. See, e.g., Liem et al., 1995, The patch clamp technique, Neurosurgery 36(2):382-92.

The patch clamp technique can potentially illustrate processes such as signal transduction and synaptic transmission as well as consequences of conditions such as demyelination, brain and spinal cord injury, and cardiac arrhythmias—to give but a few examples. Unfortunately, the technique is remarkably difficult and time-consuming to implement. To set up a patch clamp, the tip of a glass pipette must be pushed against a patch of cell membrane and suction applied to create a clamp between the pipette and the patch. The patch ruptures, cytosol enters the pipette, and measurements are made in the pipette to determine the membrane electrical properties. Variations of this basic theme are known, but they all require the fundamentally difficult and limiting steps of physically clamping a pipette to a patch of cell membrane.

SUMMARY

The invention provides methods for characterizing cellular physiology by incorporating into one or more electrically excitable cells an optical reporter of, and an optical actuator of, electrical activity. The actuator and reporter can be in the same cell or in different cells that are functionally coupled (e.g. by synapses or electrical gap junctions). A signal is obtained from the optical reporter in response to a stimulation of the actuator. Either or both of the optical reporter and actuator may be based on genetically-encoded microbial rhodopsins whose genes have been incorporated into the cell. The invention provides all-optical methods that may be used instead of, or as a complement to, traditional patch clamp technologies and that can provide rapid, accurate, and flexible assays of cellular physiology and synaptic function.

The invention further includes methods for converting a somatic cell such as a fibroblast into a specific type of electrically excitable cell using stem cell or lineage conversion technologies. A sample may be taken from a patient or other subject and converted into a neuron, a cardiomyocyte, a glial cell, any other suitable cell type, and even into specific cellular sub-types such as a motor neuron. The invention additionally provides for genome editing, so that variants of a genome of a sample or subject may be studied. By these means, a condition known to affect a certain tissue type may be studied, or the cellular phenotype of a certain mutation as well as the wild-type allele may be studied. The "optical patch clamp" methods of the invention provide for a rapid and productive way to study cellular physiology. Using methods of the invention, conditions may be diagnosed, drugs tested, and cellular function may be illustrated. This gives practitioners valuable tools for studying processes such as signal transduction and synaptic transmission as well as consequences of conditions such as demyelination, brain and spinal cord injury, and cardiac arrhythmias.

In certain aspects, the invention provides a method for characterizing a cell by incorporating into an electrically excitable cell an optical reporter of electrical activity. An optical actuator of electrical activity may also be incorporated, either into the cell or into another cell (e.g., one that is in synaptic connection with the cell). A signal is obtained from the optical reporter in response to a stimulation of the cell. The cell is characterized by evaluating the signal.

The observed signal may comprise a probability of a voltage spike in response to the stimulation of the cell, for example, a changed probability of a voltage spike in response to the stimulation of the cell relative to a control. The observed signal may also comprise a change in the waveform of a voltage spike; a change in the propagation of a voltage spike; or a sub-threshold excitatory or inhibitory change in membrane voltage that does not comprise a voltage spike. Characterizing the cell may include evaluating a response of the cell to exposure to a compound; measuring a concentration of an ion; determining progress of a treatment; or diagnosing a disease. A disease such as Cockayne syndrome, Down Syndrome, Dravet syndrome, familial dysautonomia, Fragile X Syndrome, Friedreich's ataxia, Gaucher disease, hereditary spastic paraplegias, Machado-Joseph disease, Phelan-McDermid syndrome (PMDS), polyglutamine (polyQ)-encoding CAG repeats, spinal muscular atrophy, Timothy syndrome, Alzheimer's disease, frontotemporal lobar degeneration, Huntington's disease, multiple sclerosis, Parkinson's disease, spinal and bulbar muscular atrophy, or amyotrophic lateral sclerosis may be studied or diagnosed.

In certain embodiments, the actuator, reporter, or both are incorporated by transforming the electrically active cell with a vector that includes a nucleic acid encoding the optical actuator of electrical activity, the optical reporter of electrical activity, or both. Thus one or any number of individual cells may include both an optical actuator of, and an optical reporter of, electrical activity. Alternatively, an optical actuator may be incorporated into one or any number of individual cells and an optical reporter may be incorporated into one or any number of other cells (e.g., cell or cells in synaptic connection with the reporter cell or cells).

The actuator and reporter may be incorporated into different cells for applications such as studying synaptic transmission and network properties in cultured neurons. Transmission is also important for characterizing the strength of the gap junction connections in cardiac cultures.

The optical actuator may be a genetically-encoded rhodopsin or modified rhodopsin such as a microbial channelrhodopsin. For example, sdChR, a channelrhodopsin from *Scherffelia dubia*, may be used or an improved version of sdChR— dubbed CheRiff—may be used as an optical actuator. "CheRiff" refers to a version of sdChR that uses mouse codon optimization, a trafficking sequence, and the mutation E154A as described herein.

The optical reporter may be a genetically-encoded rhodopsin or modified rhodopsin such as a microbial rhodopsin that exhibits fluorescence. For example modified versions of the microbial rhodopsin protein Archaerhodopsin 3 (Arch) from *Halorubum sodomense* may be used.

In some embodiments, the method includes obtaining a somatic cell and converting the somatic cell into the electrically excitable cell. A somatic cell may be converted into the electrically active cell by direct conversion or via an induced pluripotent stem cell (iPS) intermediary or an embryonic stem cell.

The optical actuator may initiate an action potential in response to the stimulation (e.g., illuminating the cell). The cell can be illuminated using an instrument of the invention that provides spatially resolved light from a digital micromirror array or a spatial light modulator. In some embodiments, the excitation and emission wavelengths of the optical reporter comprise light that does not stimulate the cell. Since the reporter wavelengths and actuator wavelength can be spectrally orthogonal, the invention provides methods for illuminating the cell and obtaining the signal simultaneously. Methods may include obtaining a control cell and observing a control signal generated by a control optical reporter in the control cell. Obtaining the control cell may include editing a genome from the cell such that the control cell and the cell are isogenic but for a mutation.

The invention includes methods for processing the observed signal or signals and resolving single-cells signals from among numerous signals from spatially overlapping cells. Obtaining the signal may include observing a cluster of different cells with a microscope and using a computer to isolate the signal generated by the optical reporter from a plurality of signals from the individual cells. The computer isolates the signal by performing an independent component analysis and identifying a spike train associated with the cell. A microscope of the invention may be used to obtain an image of a plurality of clusters of cells. Unlike other systems that require one image per cluster or per cell, a wide field microscope system with signal deconvolution can image and distinguish a plurality of cells or clusters per image.

Aspects of the invention provide a method for characterizing an interaction between cells. The method includes incorporating into a first electrically excitable cell an optical actuator of electrical activity, incorporating into a second electrically excitable cell an optical reporter of electrical activity, and culturing the first electrically excitable cell and the second electrically excitable cell in proximity to one another. A signal is obtained from the optical reporter in response to a stimulation of the first electrically excitable cell. The signal is evaluated, thereby characterizing an interaction between the first electrically excitable cell and the second electrically excitable cell. The first electrically excitable cell and the second electrically excitable cell may be of the same cell type or different, for example, either or both may be a neuron, a cardiomyocyte, or a glial cell. The characterized interaction may be, for example, excitatory neurotransmission, inhibitory neurotransmission, or the conduction velocity of cardiac action potential. In some embodiments, incorporating the actuator or reporter into the first or second, respectively, electrically excitable cell is done by transforming first electrically excitable cell with a vector that includes a nucleic acid encoding the optical actuator of electrical activity. The optical actuator may be provided by a modified rhodopsin as discussed herein. The optical reporter may be a rhodopsin that has been modified (e.g., for voltage-sensitive fluorescence and absence of a steady-state photocurrent). The observed signal may include a probability of a voltage spike in response to the stimulation of the cell, a changed probability of a voltage spike in response to the stimulation of the cell relative to a control, a change in the waveform of a voltage spike, a sub-threshold increase in the membrane potential, or a decrease in the membrane potential. The characterized interaction may be applied in diagnosing a disease, evaluating a cellular response to exposure to a compound, or determining progress of a treatment.

Methods can include obtaining somatic cells and converting the somatic cells into the first electrically excitable cell and the second electrically excitable cell. Converting the somatic cells may be via direct conversion, via an iPS intermediary, or the first electrically excitable cell and the second electrically excitable cell may be derived from a human embryonic stem cell.

In certain embodiments, the optical actuator initiates an action potential in response to illuminating the first electrically excitable cell (e.g., done using spatially resolved light from a digital micromirror array). Preferably, the excitation of, and the signal from, the optical reporter comprise light that does not stimulate the first electrically excitable cell. Thus, the illuminating and obtaining the signal may be done simultaneously.

In some embodiments, obtaining the signal is done by observing a cluster of different cells with a microscope and using a computer to isolate the signal generated by the optical reporter from a plurality of signals from the different cells. A microscope obtains an image of a plurality of clusters of cells. The computer isolates the signal by performing an independent component analysis and identifying a spike train associated with the second electrically excitable cell.

DETAILED DESCRIPTION

Figure 1:
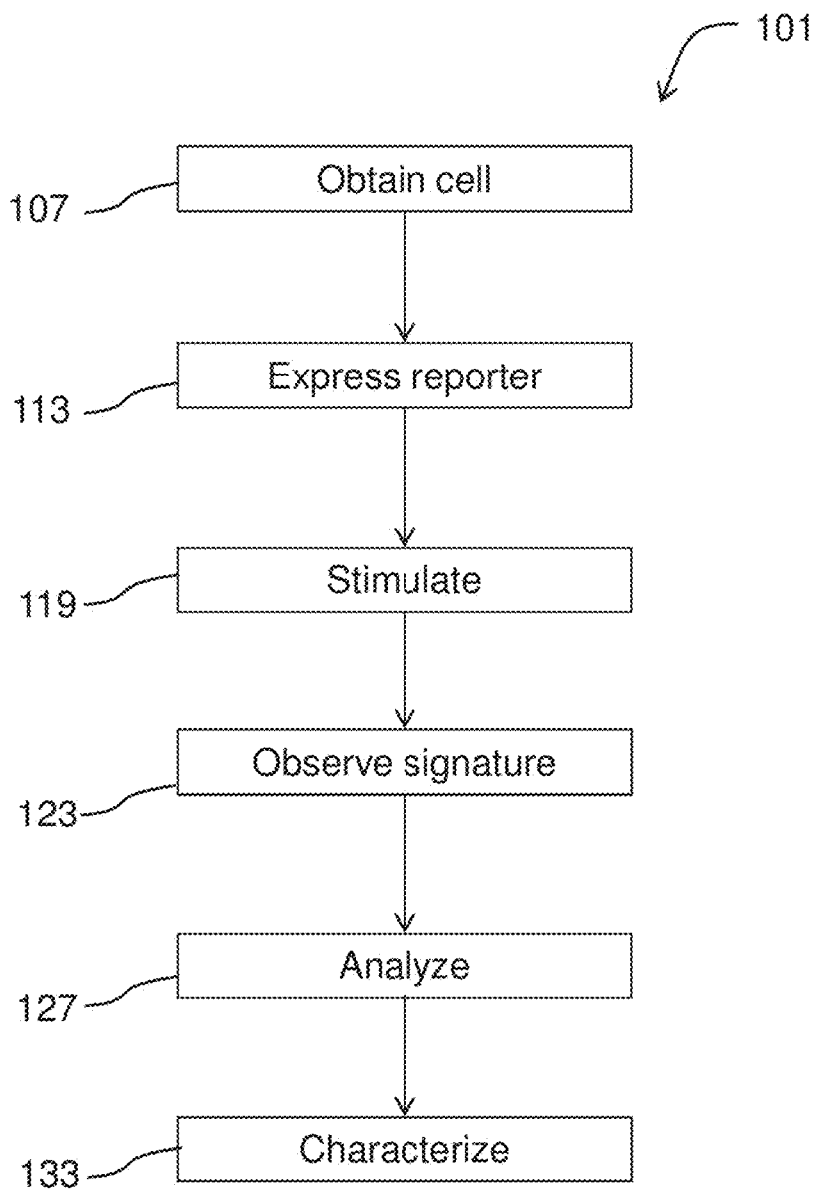
FIG. 1 illustrates a method for characterizing a cell.

FIG. 1 illustrates a method 101 to characterize 133 a cell. Methods are given to obtain 107 an electrically excitable cell. An optical actuator of, and an optical reporter of, electrical activity are incorporated into the cell. Preferably, the cell will express 113 (e.g., by translation) the reporter. An optical signal from the optical reporter in response to a stimulation of the cell is obtained. To characterize the cell, one may observe 123 a signature of the signal and analyze or evaluate 127 the signature. By evaluating the signal, one may characterize 133 the cell.

Additionally, methods of the invention may be employed to study and use network effects whereby one cell or genetically specified cell type is stimulated, and a different one is recorded. Both cells might have both actuator and reporter; or one might have actuator only, and the other reporter only. This ability to probe network effects may be particularly important as many genes, such as ones that are being implicated in schizophrenia and bipolar disorder, code for synaptic proteins. Network effects also promise to be important in the cardiac area, where for example a monolayer of cardiomyocytes may be illuminated with some cells expressing actuators of the invention while imaged via others expressing the reporters.

1. Obtaining Cell(s)

Cells that are useful according to the invention include eukaryotic and prokaryotic cells. Eukaryotic cells include cells of non-mammalian invertebrates, such as yeast, plants, and nematodes, as well as non-mammalian vertebrates, such as fish and birds. The cells also include mammalian cells, including mouse, rat, and human cells. The cells also include immortalized cell lines such as HEK, HeLa, CHO, 3T3, PC12, which may be particularly useful in applications of the methods for drug screens. The cells also include stem cells, embryonic stem cells, pluripotent cells, progenitor cells, and induced pluripotent cells. Differentiated cells including cells differentiated from the stem cells, pluripotent cells and progenitor cells are included as well.

Cells are obtained by any suitable means. For example, methods of the invention can include obtaining one or more cells such as fibroblasts from an organism such as a person or animal. In some embodiments, a dermal biopsy is performed to obtain dermal fibroblasts. The skin is anesthetized and a sterile 3 mm punch is used to apply pressure and make a drilling motion until the punch has pierced the epidermis. A biopsy sample is lifted out and transferred to a sterile BME fibroblast medium after optional washing with PBS and evaporation of the PBS. The biopsy site on the patient is dressed (e.g., with an adhesive bandage). Suitable methods and devices for obtaining the cells are discussed in U.S. Pat. No. 8,603,809; U.S. Pat. No. 8,403,160; U.S. Pat. No. 5,591,444; U.S. Pub. 2012/0264623; and U.S. Pub. 2012/0214236, the contents of each of which are incorporated by reference. Any tissue culture technique that is suitable for the obtaining and propagating biopsy specimens may be used such as those discussed in Freshney, Ed., 1986, Animal Cell Culture: A Practical Approach, IRL Press, Oxford England; and Freshney, Ed., 1987, Culture of Animal Cells: A Manual of Basic Techniques, Alan R. Liss & Co., New York, both incorporated by reference.

In some embodiments, the cells are cultured in vitro or ex vivo. In some embodiments, the cells are part of an organ or an organism.

In some embodiment, the cell is an "artificial cell" or a "synthetic cell" created by bioengineering (see, e.g., Gibson et al., 2010, Creation of a Bacterial Cell Controlled by a Chemically Synthesized Genome, Science 329(5987):52-56; Cans et al., 2008, Positioning Lipid Membrane Domains in Giant Vesicles by Micro-organization of Aqueous Cytoplasm Mimic, J Am Chem Soc 130:7400-7406.

The methods can also be applied to any other membrane-bound structure, which may not necessarily be classified as a cell. Such membrane bound structures can be made to carry the microbial rhodopsin proteins of the invention by, e.g., fusing the membranes with cell membrane fragments that carry the microbial rhodopsin proteins of the invention.

Cells may include zebrafish cardiomyocytes; immune cells (primary murine and human cultures and iPS-derived lines for all, in addition to the specific lines noted below), including B cells (e.g., human Raji cell line, and the DT40 chicken cell line), T cells (e.g., human Jurkat cell line), Macrophages, Dendritic cells, and Neutrophils (e.g., HL-60 line). Additionally, one can use glial cells: astrocytes and oligodendrocytes; pancreatic beta cells; hepatocytes; non-cardiac muscle cells;

endocrine cells such as parafollicular and chromaffin; and yeast cells. Cells further include neuronal cells, such as neurons.

The cell can also be a Gram positive or a Gram negative bacteria, as well as pathogenic bacteria of either Gram type. The pathogenic cells are useful for applications of the method to, e.g., screening of novel antibiotics that affect membrane potential to assist in destruction of the bacterial cell or that assist destruction of the bacterial cell in combination with the membrane potential affecting agent; or in the search for compounds that suppress efflux of antibiotics.

The membrane potential of essentially any cell, or any phospholipid bilayer enclosed structure, can be measured using the methods and compositions described herein. Examples of the cells that can be assayed are a primary cell e.g., a primary hepatocyte, a primary neuronal cell, a primary myoblast, a primary mesenchymal stem cell, primary progenitor cell, or it may be a cell of an established cell line. It is not necessary that the cell be capable of undergoing cell division; a terminally differentiated cell can be used in the methods described herein. In this context, the cell can be of any cell type including, but not limited to, epithelial, endothelial, neuronal, adipose, cardiac, skeletal muscle, fibroblast, immune cells, hepatic, splenic, lung, circulating blood cells, reproductive cells, gastrointestinal, renal, bone marrow, and pancreatic cells. The cell can be a cell line, a stem cell, or a primary cell isolated from any tissue including, but not limited to brain, liver, lung, gut, stomach, fat, muscle, testes, uterus, ovary, skin, spleen, endocrine organ and bone, etc. Where the cell is maintained under in vitro conditions, conventional tissue culture conditions and methods can be used, and are known to those of skill in the art. Isolation and culture methods for various cells are well within the knowledge of one skilled in the art. The cell can be a prokaryotic cell, a eukaryotic cell, a mammalian cell or a human cell. In one embodiment, the cell is a neuron or other cell of the brain. In some embodiment, the cell is a cardiomyocyte. In some embodiments, the cell is cardiomyocyte that has been differentiated from an induced pluripotent cell.

2. Converting Cell(s) into Neurons, Cardiomyocytes, or Specific Neural Sub-Types Obtained cells may be converted into any electrically excitable cells such as neurons, specific neuronal subtypes, astrocytes or other glia, cardiomyocytes, or immune cells. Additionally, cells may be converted and grown into co-cultures of multiple cell types (e.g. neurons+glia, neurons+cardiomyocytes, neurons+immune cells).

Figure 2:
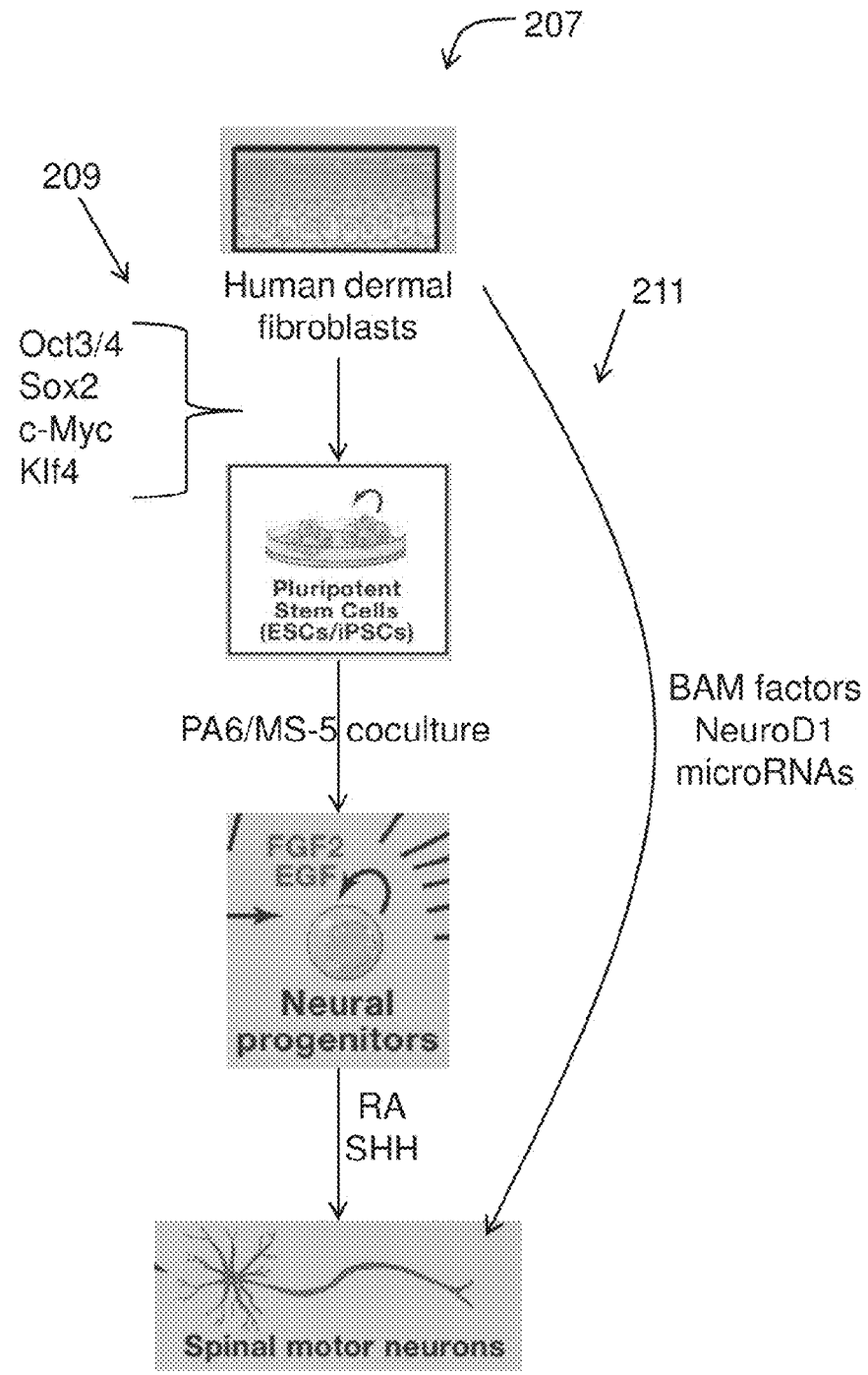
FIG. 2 illustrates exemplary pathways for converting cells into specific neural subtypes.

FIG. 2 illustrates exemplary pathways for converting cells into specific neural subtypes. A cell may be converted to a specific neural subtype (e.g., motor neuron). Suitable methods and pathways for the conversion of cells include pathway 209, conversion from somatic cells to induced pluripotent stem cells (iPSCs) and conversion of iPSCs to specific cell types, or pathways 211 direct conversion of cells in specific cell types.

2a. Conversion of Cells to iPSs and Conversion of iPSs to Specific Cell Types

Following pathways 209, somatic cells may be reprogrammed into induced pluripotent stem cells (iPSCs) using known methods such as the use of defined transcription factors. The iPSCs are characterized by their ability to proliferate indefinitely in culture while preserving their developmental potential to differentiate into derivatives of all three embryonic germ layers. In certain embodiments, fibroblasts are converted to iPSC by methods such as those discussed in Takahashi and Yamanaka, 2006, Induction of pluripotent stem cells from mouse embryonic and adult fibroblast cultures by defined factors Cell 126:663-676.; and Takahashi, et al., 2007, Induction of pluripotent stem cells from adult human fibroblasts by defined factors, *Cell* 131:861-872.

Induction of pluripotent stem cells from adult fibroblasts can be done by methods that include introducing four factors, Oct3/4, Sox2, c-Myc, and Klf4, under ES cell culture conditions. Human dermal fibroblasts (HDF) are obtained. A retroviruses containing human Oct3/4, Sox2, Klf4, and c-Myc is introduced into the HDF. Six days after transduction, the cells are harvested by trypsinization and plated onto mitomycin C-treated SNL feeder cells. See, e.g., McMahon and Bradley, 1990, Cell 62:1073-1085. About one day later, the medium (DMEM containing 10% FBS) is replaced with a primate ES cell culture medium supplemented with 4 ng/mL basic fibroblast growth factor (bFGF). See Takahashi, et al., 2007, Cell 131:861. Later, hES cell-like colonies are picked and mechanically disaggregated into small clumps without enzymatic digestion. Each cell should exhibit morphology similar to that of human ES cells, characterized by large nuclei and scant cytoplasm. The cells after transduction of HDF are human iPS cells. DNA fingerprinting, sequencing, or other such assays may be performed to verify that the iPS cell lines are genetically matched to the donor.

These iPS cells can then be differentiated into specific neuronal subtypes. Pluripotent cells such as iPS cells are by definition capable of differentiating into cell types characteristic of different embryonic germ layers. A property of both embryonic stem cells human iPS cells is their ability, when plated in suspension culture, to form embryoid bodies (EBs). EBs formed from iPS cells are treated with two small molecules: an agonist of the sonic hedgehog (SHH) signaling pathway and retinoic acid (RA). For more detail, see the methods described in Dimos et al., 2008, Induced pluripotent stem cells generated from patients with ALS can be differentiated into motor neurons, Science 321(5893):1218-21; Amoroso et al., 2013, Accelerated high-yield generation of limb-innervating motor neurons from human stem cells, J Neurosci 33(2):574-86; and Boulting et al., 2011, A functionally characterized test set of human induced pluripotent stem cells, Nat Biotech 29(3):279-286; Davis-Dusenbery et al., 2014, How to make spinal motor neurons, Development 141(3):491-501; Sandoe and Eggan, 2013, Opportunities and challenges of pluripotent stem cell neurodegenerative disease models, Nat Neuroscience 16(7):780-9; and Han et al., 2011, Constructing and deconstructing stem cell models of neurological disease, Neuron 70(4):626-44.

2b. Direct Conversion of Cells in Specific Cell Types

By pathway 211, human somatic cells are obtained and direct lineage conversion of the somatic cells into motor neurons may be performed. Conversion may include the use of lineage-specific transcription factors to induce the conversion of specific cell types from unrelated somatic cells. See, e.g., Davis-Dusenbery et al., 2014, How to make spinal motor neurons, Development 141:491; Graf, 2011, Historical origins of transdifferentiation and reprogramming, Cell Stem Cell 9:504-516. It has been shown that a set of neural lineage-specific transcription factors, or BAM factors, causes the conversion of fibroblasts into induced neuronal (iN) cells. Vierbuchen 2010 Nature 463:1035. MicroRNAs and additional pro-neuronal factors, including NeuroD1, may cooperate with or replace the BAM factors during conversion of human fibroblasts into neurons. See, for example, Ambasudhan et al., 2011, Direct reprogramming of adult human fibroblasts to functional neurons under defined conditions, *Cell Stem Cell* 9:113-118; Pang et al., 2011, Induction of human neuronal cells by defined transcription factors, Nature 476:220-223; also see Yoo et al., 2011, MicroRNA mediated conversion of human fibroblasts to neurons, Nature 476:228-231.

2c. Maintenance of Differentiated Cells

Differentiated cells such as motor neurons may be dissociated and plated onto glass coverslips coated with poly-d-lysine and laminin. Motor neurons may be fed with a suitable medium such as a neurobasal medium supplemented with N2, B27, GDNF, BDNF, and CTNF. Cells may be maintained in a suitable medium such as an N2 medium (DMEM/F, 12 [1:1] supplemented with laminin [1 µg/mL; Invitrogen], FGF-2 [10 ng/ml; R&D Systems, Minneapolis, Minn.], and N2 supplement [1%; Invitrogen]), further supplemented with GDNF, BDNF, and CNTF, all at 10 ng/ml. Suitable media are described in Son et al., 2011, Conversion of mouse and human fibroblasts into functional spinal motor neurons, *Cell Stem Cell* 9:205-218; Vierbuchen et al., 2010, Direct conversion of fibroblasts to functional neurons by defined factors, Nature 4 63:1035-1041; Kuo et al., 2003, Differentiation of monkey embryonic stem cells into neural lineages, Biology of Reproduction 68:1727-1735; and Wernig et al., 2002, Tau EGFP embryonic stem cells: an efficient tool for neuronal lineage selection and transplantation. J Neuroscience Res 69:918-24, each incorporated by reference.

3. Control Cell Line or Signature or Reference Value

Methods of the invention may include obtaining or observing a signal from the cell and comparing the observed signal to an expected signal, such as a signal obtained from a reference.

The term "reference" as used herein refers to a baseline value of any kind that one skilled in the art can use in the methods. In some embodiments, the reference is a cell that has not been exposed to a stimulus capable of or suspected to be capable of changing membrane potential. In one embodiment, the reference is the same cell transfected with the microbial rhodopsin but observed at a different time point. In another embodiment, the reference is the fluorescence of a homologue of Green Fluorescent Protein (GFP) operably fused to the microbial rhodopsin.

The reference signature may be obtained by obtaining a control cell that is also of the specific neural subtype and is genetically and phenotypically similar to the test cells. In certain embodiments—where, for example, a patient has a known mutation or allele at a certain locus—genetic editing is performed to correct the mutation and generate a control cell.

Genetic or genome editing techniques may proceed by any suitable method such as zinc-finger domain methods, transcription activator-like effector nucleases (TALENs), or clustered regularly interspaced short palindromic repeat (CRISPR) nucleases. Genome editing may be used to create a control cell that is isogenic but—for a variant of interest or to obtain other variants of the original genome, such as knocking out a gene, introducing a premature stop codon, interfering with a promoter region, or changing the function of an ion channel or other cellular protein. In certain embodiments, genome editing techniques are applied to the iPS cells. Genomic editing may be performed by any suitable method known in the art such as TALENs or CRISPR technology. TALENs and CRISPR methods provide one-to-one relationship to the target sites, i.e. one unit of the tandem repeat in the TALE domain recognizes one nucleotide in the target site, and the crRNA or gRNA of CRISPR/Cas system hybridizes to the complementary sequence in the DNA target. Methods can include using a pair of TALENs or a Cas9 protein with one gRNA to generate double-strand breaks in the target. The breaks are then repaired via non-homologous end-joining or homologous recombination (HR).

TALENs uses a nonspecific DNA-cleaving nuclease fused to a DNA-binding domain that can be to target essentially any sequence. For TALEN technology, target sites are identified and expression vectors are made. See Liu et al, 2012, Efficient and specific modifications of the *Drosophila* genome by means of an easy TALEN strategy, J. Genet. Genomics 39:209-215. The linearized expression vectors (e.g., by NotI) and used as template for mRNA synthesis. A commercially available kit may be use such as the mMESSAGE mMACHINE SP6 transcription kit from Life Technologies (Carlsbad, Calif.). See Joung & Sander, 2013, TALENs: a widely applicable technology for targeted genome editing, Nat Rev Mol Cell Bio 14:49-55.

CRISPR methodologies employ a nuclease, CRISPR-associated (Cas9), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas9 and guide RNA (gRNA) may be synthesized by known methods. Cas9/guide-RNA (gRNA) uses a non-specific DNA cleavage protein Cas9, and an RNA oligo to hybridize to target and recruit the Cas9/gRNA complex. See Chang et al., 2013, Genome editing with RNA-guided Cas9 nuclease in zebrafish embryos, Cell Res 23:465-472; Hwang et al., 2013, Efficient genome editing in zebrafish using a CRISPR-Cas system, Nat. Biotechnol 31:227-229; Xiao et al., 2013, Chromosomal deletions and inversions mediated by TALENS and CRISPR/Cas in zebrafish, Nucl Acids Res 1-11.

In certain embodiments, genome editing is performed using zinc finger nuclease-mediated process as described, for example, in U.S. Pub. 2011/0023144 to Weinstein.

Figure 3:
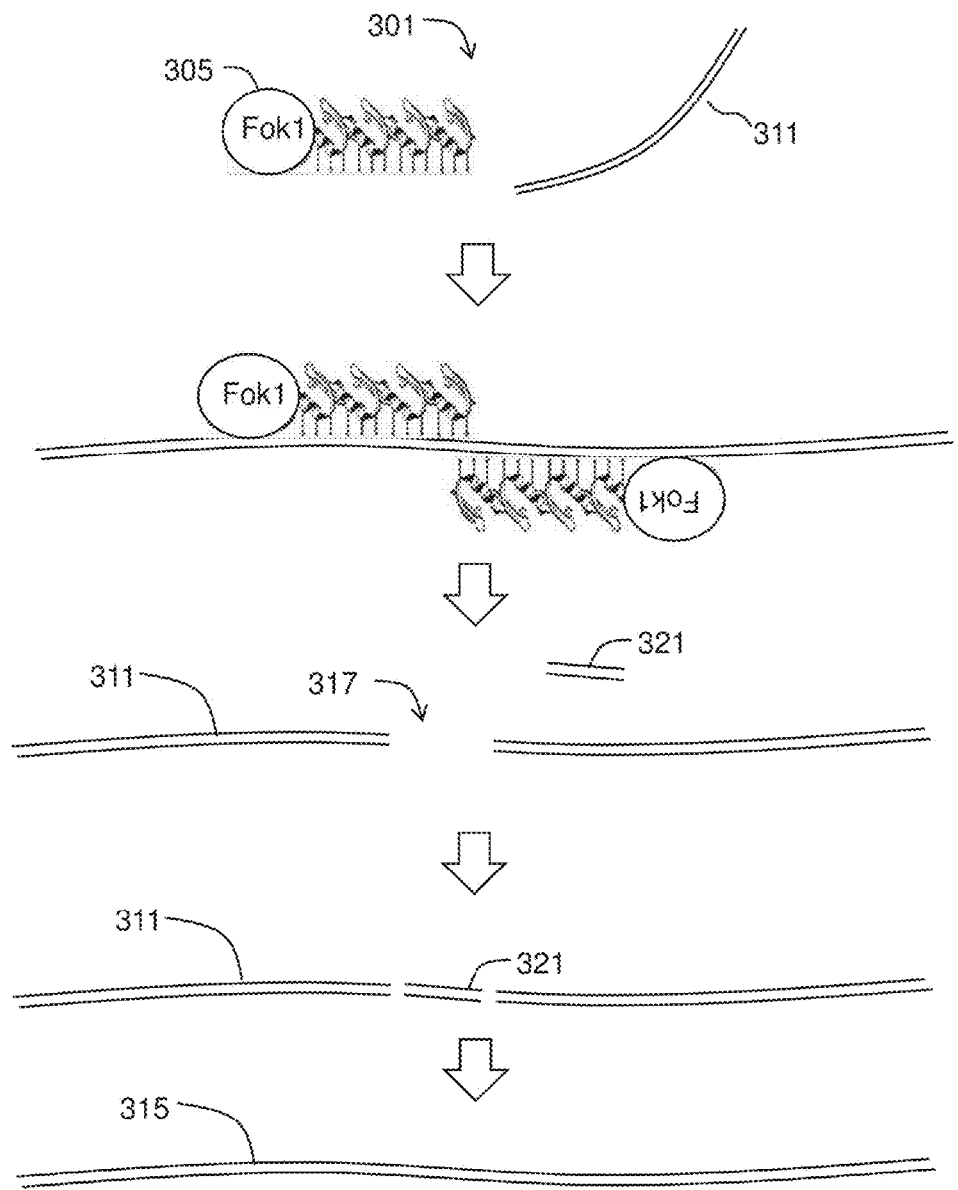
FIG. 3 gives an overview of a method for genome editing.

FIG. 3 gives an overview of a method 301 for zing-finger nuclease mediated editing. Briefly, the method includes introducing into the iPS cell at least one RNA molecule encoding a targeted zinc finger nuclease 305 and, optionally, at least one accessory polynucleotide. The cell includes target sequence 311. The cell is incubated to allow expression of the zinc finger nuclease 305, wherein a double-stranded break 317 is introduced into the targeted chromosomal sequence 311 by the zinc finger nuclease 305. In some embodiments, a donor polynucleotide or exchange polynucleotide 321 is introduced. Target DNA 311 along with exchange polynucleotide 321 may be repaired by an error-prone non-homologous end-joining DNA repair process or a homology-directed DNA repair process. This may be used to produce a control line with a control genome 315 that is isogenic to original genome 311 but for a changed site. The genomic editing may be used to establish a control line (e.g., where the patient is known to have a certain mutation, the zinc finger process may revert the genomic DNA to wild type) or to introduce a mutation (e.g., non-sense, missense, or frameshift) or to affect transcription or expression. See also Beerli & Barbas, 2002, Engineering polydactyl zing-finger transcription factors, Nat. Biotechnol, 20:135-141; Pabo et al., 2001, Design and selection of novel Cys2H is2 zinc finger proteins, Ann. Rev. Biochem 70:313-340; Isalan et al., 2001, A rapid generally applicable method to engineer zinc fingers illustrated by targeting the HIV-1 promoter, Nat. Biotechnol 19:656-660; Santiago et al., 2008, Targeted gene knockout in mammalian cells by using engineered zinc-finger nucleases, PNAS 105: 5809-5814; Santiago et al, 2008, Targeted gene knockout in mammalian cells by using engineered zinc finger nucleases, PNAS 105:5809-5814; Moehle et al., 2007, Targeted gene addition into a specified location in the human genome using designed zinc finger nucleases PNAS 104:3055-3060; Urnov et al., 2005, Highly efficient endogenous human gene correction using designed zinc-finger nucleases, Nature 435(7042): 646-51; and Lombardo et al., 2007, Gene editing in human stem cells using zinc finger nucleases and integrase-defective lentiviral vector delivery, Nat Biotechnol 25(11):1298-306; U.S. Pat. Nos. 6,607,882; 6,534,261 and 6,453,242; U.S. Pat. No. 5,789,538; U.S. Pat. No. 5,925,523; U.S. Pat. No. 6,007, 988; U.S. Pat. No. 6,013,453; U.S. Pat. No. 6,410,248; U.S. Pat. No. 6,140,466; U.S. Pat. No. 6,200,759; and U.S. Pat. No. 6,242,568, each of which is incorporated by reference.

Using genome editing for modifying a chromosomal sequence, a control cell or cell line can be generated, or any other genetic variant of the first cell may be created. In certain embodiments, control cells are obtained from healthy individuals, i.e., without using genome editing on cells taken from the subject. The control line can be used to generate a control signature, or reference, for comparison to test data. In some embodiments, a control signature is stored on-file after having been previously generated and stored and the stored control signature is used (e.g., a digital file such as a graph or series of measurements stored in a non-transitory memory in a computer system). For example, a control signature could be generated by assaying a large population of subjects of known phenotype or genotype and storing an aggregate result as a control signature for later downstream comparisons.

4. Optogenetic Systems

In a preferred embodiment, methods of the invention include characterizing a cell by incorporating into a cell an optical actuator of electrical activity and an optical reporter of electrical activity—i.e., both into one cell or each of a plurality of cells. In some embodiments, a cell will receive one of the actuator and reporter. In certain embodiments, a cell will receive both via transfection with a single vector that includes genes coding for each of the reporter and actuator. As used herein the term "optical reporter" refers to a structure or system employed to yield an optical signal indicative of cellular electrical or neural activity such as a voltage drop across a membrane, a synaptic transmission, an action potential, a release or uptake or non-uptake of a neurotransmitter, etc. As used herein, the term "membrane potential" refers to a calculated difference in voltage between the interior and exterior of a cell. In one embodiment membrane potential, $\Delta V$, is determined by the equation $\Delta V=V(\text{interior})-V(\text{exterior})$. By convention, $V(\text{exterior})$ is regarded as 0 V, so then $\Delta V=V(\text{interior})$.

4a. Optogenetic Reporters

The cell and the optional control line may be caused to express an optical reporter of neural or electrical activity. Examples of neural activity include action potentials in a neuron or fusion of vesicles releasing neurotransmitters. Exemplary electrical activity includes action potentials in a neuron, cardiomyocyte, astrocyte or other electrically active cell. Further examples of neural or electrical activity include ion pumping or release or changing ionic gradients across membranes. Causing a cell to express an optical reporter of neural activity can be done with a fluorescent reporter of vesicle fusion. Expressing an optical reporter of neural or electrical activity can include transformation with an optogenetic reporter. For example, the cell may be transformed with a vector comprising an optogenetic reporter and the cell may also be caused to express an optogenetic actuator by transformation. In certain embodiments, the differentiated neurons are cultured (e.g., for about 4 days) and then infected with lentivirus bearing a genetically encoded optical reporter of neural or electrical activity and optionally an optical voltage actuator.

Any suitable optical reporter of neural or electrical activity may be used. Exemplary reporters include fluorescent reporters of transmembrane voltage differences, pHluorin-based reporters of synaptic vesicle fusion, and genetically encoded calcium indicators. In a preferred embodiment, a genetically encoded voltage indicator is used. Genetically encoded voltage indicators that may be used or modified for use with methods of the invention include FlaSh (Siegel, 1997, A genetically encoded optical probe of membrane voltage. Neuron 19:735-741); SPARC (Ataka, 2002, A genetically targetable fluorescent probe of channel gating with rapid kinetics, Biophys J 82:509-516); and VSFP1 (Sakai et al., 2001, Design and characterization of a DNA encoded, voltage-sensitive fluorescent protein, Euro J Neuroscience 13:2314-2318). A genetically encoded voltage indicator based on the paddle domain of a voltage-gated phosphatase is CiVSP (Murata et al., 2005, Phosphoinositide phosphatase activity coupled to an intrinsic voltage sensor, Nature 435:1239-1243). Another indicator is the hybrid hVOS indicator (Chanda et al., 2005, A hybrid approach to measuring electrical activity in genetically specified neurons, Nat Neuroscience 8:1619-1626), which transduces the voltage dependent migration of dipicrylamine (DPA) through the membrane leaflet to "dark FRET" (fluorescence resonance energy transfer) with a membrane-targeted GFP. Methods of the invention may use a genetically encoded voltage indicator in which a fluorescent moiety is inserted in the voltage sensing domain. For example, in Accelerated Sensor of Action Potentials 1 (ASAP1), a circularly permuted green fluorescent protein is inserted in an extracellular loop of a voltage-sensing domain, rendering fluorescence responsive to membrane potential. In some embodiments, ASAP1 is used as a reporter. ASAP1 is described in St-Pierre et al., 2014, High-fidelity optical reporting of neuronal electrical activity with an ultrafast fluorescent voltage sensor, Nature Neuroscience 17(6):884-889.

In certain embodiments, an optical reporter of electrical activity in a cell is provided by a microbial rhodopsin or a modified microbial rhodopsin. A typical microbial rhodopsin is a light-driven proton pump structured as an integral membrane protein belonging to the family of archaeal rhodopsins. Archaeal rhodopsins are characterized by seven transmembrane helices with a retinal chromophore buried therein, the retinal chromophore being covalently bound to conserved lysine residue in one of the helices via a Schiff base. See Neutze et al., 2002, Bacteriorhodopsin: a high-resolution structural view of vectorial proton transport, Biochimica et Biophysica Acta 1565:144-167; Beja et al., 2001, Proteorhodopsin phototrophy in the ocean, Nature 411:786-789. The invention includes the insight that microbial rhodopsins or modified microbial rhodopsins that have reduced ion pumping activity—compared to the natural microbial rhodopsin protein from which they are derived—can be used as an optically detectable sensor to sense voltage across membranous structures, such as in cells and sub-cellular organelles when they are present in the lipid bilayer membrane. That is, the microbial rhodopsin proteins and the modified microbial rhodopsin proteins can be used as optical reporters to measure changes in membrane potential of a cell, including prokaryotic and eukaryotic cells. The optical reporters described herein are not constrained by the need for electrodes and permit electrophysiological studies to be performed in e.g., subcellular compartments (e.g., mitochondria) or in small cells (e.g., bacteria). The optical reporters described herein can be used in methods for drug screening, in research settings, and in in vivo imaging systems.

The retinal chromophore imbues microbial rhodopsins with unusual optical properties. The linear and nonlinear responses of the retinal are highly sensitive to interactions with the protein host: small changes in the electrostatic environment can lead to large changes in absorption spectrum. These electro-optical couplings provide the basis for voltage sensitivity in microbial rhodopsins.

Some of the optical reporters described herein are natural proteins without modifications and are used in cells that do not normally express the microbial rhodopsin transfected to the cell, such as eukaryotic cells. For example, as shown in the examples, the wild type Archaerhodopsin 3 can be used in neural cells to specifically detect membrane potential and changes thereto.

Some of the microbial rhodopsins are derived from a microbial rhodopsin protein by modification of the protein to reduce or inhibit light-induced ion pumping of the rhodopsin protein. Such modifications permit the modified microbial rhodopsin proteins to sense voltage without altering the membrane potential of the cell with its native ion pumping activity. Other mutations impart other advantageous properties to microbial rhodopsin voltage sensors, including increased fluorescence brightness, improved photostability, tuning of the sensitivity and dynamic range of the voltage response, increased response speed, and tuning of the absorption and emission spectra.

Provided herein are illustrative exemplary optical voltage reporters and directions for making and using such sensors. Other sensors that work in a similar manner as optical reporters can be prepared and used based on the description and the examples provided herein.

Exemplary microbial rhodopsins include: green-absorbing proteorhodopsin (GPR, Gen Bank #AF349983), a light-driven proton pump found in marine bacteria; blue absorbing proteorhodopsin (BPR, GenBank #AF349981), a light-driven proton pump found in marine bacteria; *Natronomonas pharaonis* sensory rhodopsin II (NpSR11, GenBank #Z35086.1), a light-activated signaling protein found in the halophilic bacterium *N. pharaonis*; bacteriorhodopsin (BR, GenBank #NC_010364.1), a light-driven proton pump found in *Halobacterium salinarum*; Archaerhodopsin 3 (Arch3, GenBank #P96787), a light-driven proton pump found in *Halobacterium sodomense*; variants of the foregoing; and others discussed herein. Additional rhodopsions that can be mutated as indicated in the methods of the invention include fungal opsin related protein (Mac, GenBank #AAG01180); Cruxrhodopsin (Crux, GenBank #BAA06678); Algal bacteriorhodopsin (Ace, GenBank #AAY82897); Archaerhodopsin 1 (Arch 1, GenBank #P69051); Archaerhodopsin 2 (Arch 2, GenBank #P29563); and Archaerhodopsin 4 (Arch 4, GenBank #AAG42454). Some of the foregoing are pointed to by Genbank number. However, a rhodopsin may vary from a sequence in GenBank. Based on the description of the motif described herein, a skilled artisan will easily be able to make homologous mutations in microbial rhodopsin genes to achieve the described or desired functions, e.g. reduction in the pumping activity of the microbial rhodopsin in question.

In one embodiment, the green-absorbing proteorhodopsin (GPR) is used as a starting molecule to provide an optical reporter. This molecule is selected for its relatively red-shifted absorption spectrum and its ease of expression in heterologous hosts such as *E. coli*. In another embodiment, the blue-absorbing proteorhodopsin (BPR) is used as an optical reporter of voltage. Microbial rhodopsins are sensitive to quantities other than voltage. Mutants of GPR and BPR, as described herein, are also sensitive to intracellular pH. It is also contemplated that mutants of halorhodopsin may be sensitive to local chloride concentration. GPR has seven spectroscopically distinguishable states that it passes through in its photocycle. In principle the transition between any pair of states is sensitive to membrane potential. In one embodiment, the acid-base equilibrium of the Schiff base is chosen as the wavelength-shifting transition, hence the name of the reporter: Proteorhodopsin Optical Proton Sensor (PROPS). The absorption spectrum of wild-type GPR is known to depend sensitively on the state of protonation of the Schiff base. When protonated, the absorption maximum is at 545 nm, and when deprotonated the maximum is at 412 nm. When GPR absorbs a photon, the retinal undergoes a 13-trans to cis isomerization, which causes a proton to hop from the Schiff base to nearby Asp97, leading to a shift from absorption at 545 nm to 412 nm. The PROPS design described herein seeks to recapitulate this shift in response to a change in membrane potential.

Two aspects of wild-type GPR can be changed for it to serve as an optimal voltage sensor. First, the pKa of the Schiff base can be shifted from its wild-type value of 12 to a value close to the ambient pH. When pKa approximately equals pH, the state of protonation becomes maximally sensitive to the membrane potential. Second, the endogenous charge-pumping capability can be eliminated so the reporter does not perturb the quantity under study. However, in some situations, a wild type microbial rhodopsin can be used, such as Arch 3 WT, which functions in neurons to measure membrane potential as shown in our examples.

In one embodiment, a single point mutation induces both changes in GPR. Mutating Asp97 to Asn eliminates a negative charge near the Schiff base, and destabilizes the proton on the Schiff base. The pKa shifts from about 12 to 9.8. In wild-type GPR, Asp97 also serves as the proton acceptor in the first step of the photocycle, so removing this amino acid eliminates proton pumping. This mutant of GPR is referred to herein as PROPS. Similarly, in an analogous voltage sensor derived from BPR, the homologous mutation Asp99 to Asn lowers the pKa of the Schiff base and eliminates the proton-pumping photocycle. Thus, in one embodiment the optical reporter is derived from BPR in which the amino acid residue Asp99 is mutated to Asn.

In GPR, additional mutations shift the pKa closer to the physiological value of 7.4. In particular, mutations Glu108 to Gln and Glu142 to Gln individually or in combination lead to decreases in the pKa and to further increases in the sensitivity to voltage. Many mutations other than those discussed herein may lead to additional changes in the pKa and improvements in the optical properties of PROPS and are contemplated herein.

The invention provides reporters based on rhodopsins with introduced mutations. For example, mutations that eliminate pumping in microbial rhodopsins in the present invention generally comprise mutations to the Schiff base counterion; a carboxylic amino acid (Asp or Glu) conserved on the third transmembrane helix (helix C) of the rhodopsin proteins. Mutations to the carboxylic residue directly affect the proton conduction pathway, eliminating proton pumping (e.g., Asp to Asn, Gln, or His mutation, or Glu to Asn Gln, or His mutation). Mutating the proton acceptor aspartic acid adjacent the Schiff base to asparagine suppresses proton pumping. Thus, in some embodiments, the mutations are selected from the group consisting of: D97N (green-absorbing proteorhodopsin), D95N (Archaerhodopsin 3), D99N (blue-absorbing proteorhodopsin), D75N (sensory rhodopsin II), and D85N (bacteriorhodopsin). In other embodiments, residues that can be mutated to inhibit pumping include (using bacteriorhodopsin numbering) D96, Y199, and R82, and their homologues in other microbial rhodopsins. In another embodiment, residue D95 can be mutated in Archaerhodopsin to inhibit proton pumping (e.g., D95N). Residues near the binding pocket can be mutated singly or in combination to tune the spectra to a desired absorption and emission wavelength. In bacteriorhodopsin these residues include, but are not limited to, L92, W86, W182, D212, I119, and M145. Homologous residues may be mutated in other microbial rhodopsins. Thus, in some embodiments, the mutation to modify the microbial rhodopsin protein is performed at a residue selected from the group consisting of L92, W86, W182, D212, I119, M145. Mutations can shift the dynamic range of voltage sensitivity into a desired band by shifting the distribution of charge in the vicinity of the Schiff base, and thereby changing the voltage needed to add or remove a proton from this group. Voltage-shifting mutations in green-absorbing proteorhodopsin include, but are not limited to, E108Q, E142Q, L217D, either singly or in combination using green-absorbing proteorhodopsin locations as an example, or a homologous residue in another rhodopsin. In one embodiment, a D95N mutation is introduced into Archaerhodopsin 3 to adjust the pKa of the Schiff base towards a neutral pH. Additionally or alternatively, mutations can enhance brightness, photostability, or both. Residues which, when mutated, may restrict the binding pocket to increase fluorescence include (using bacteriorhodopsin numbering) Y199, Y57, P49, V213, and V48.

Optical reporters that may be suitable for use with the invention include those that use the endogenous fluorescence of the microbial rhodopsin protein Archaerhodopsin 3 (Arch) from *Halorubum sodomense*. Arch resolves action potentials with high signal-to-noise (SNR) and low photo-toxicity.

Figure 4:
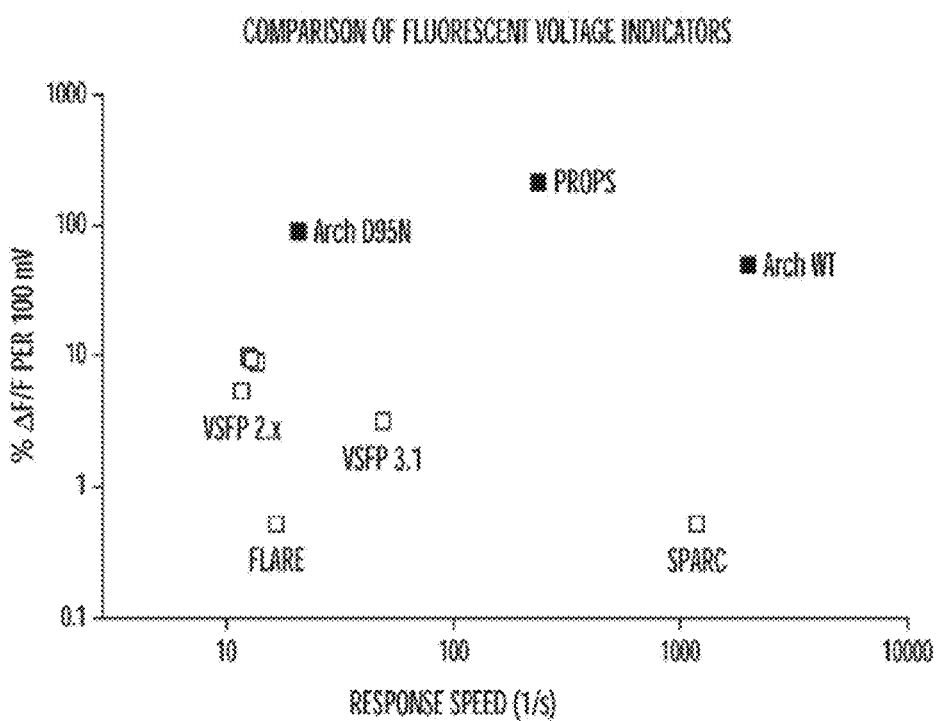
FIG. 4 shows genetically encoded fluorescent voltage indicators classified according to their sensitivity and speed.

FIG. 4 shows genetically encoded fluorescent voltage indicators classified according to their sensitivity and speed—the two key parameters that determine the performance of an indicator. The invention provides reporters such as Proteorhodopsin Optical Proton Sensor (PROPS), Arch 3 WT, and Arch 3 D95N, shown on the upper right. PROPS functions in bacteria, while Arch 3 WT and Arch 3 D95N function in mammalian cells. Such microbial rhodopsin-based voltage indicators are faster and far more sensitive than other indicators.

The invention may use optical reporters that include fluorescent voltage indicating proteins such as VSFP 2.3 (Knopfel et al., 2010, J Neurosci 30:14998-15004), which exhibits a response time of 78 ms and f (where f=(delta F/F per 100 mV)) of 9.5%. VSFP 2.4 (Ibid.) has a 72 ms response time and f of 8.9%. VSFP 3.1 (Lundby et al., 2008, PLoSOne 3:2514) has a response time of 1-20 ms and a F of 3%. Mermaid is a molecule described in Perron et al., 2009, Front Mol Neurosci 2:1-8 with a response time of 76 and a F of 9.2%. SPARC (Ataka & Pieribone, 2002, Biophys J 82:509-516) response time 0.8 ms and F 0.5%. Flash (Siegel, 1997, Neuron 19:735-741) has response time 2.8-85 ms and f of 5.1%. Arch 3 WT has a response time of <0.5 ms and f of 66%. Arch D95N has a response time of 41 ms and f of 100%.

Optical recording of action potentials were made in a single rat hippocampal neuron.

Figure 5:
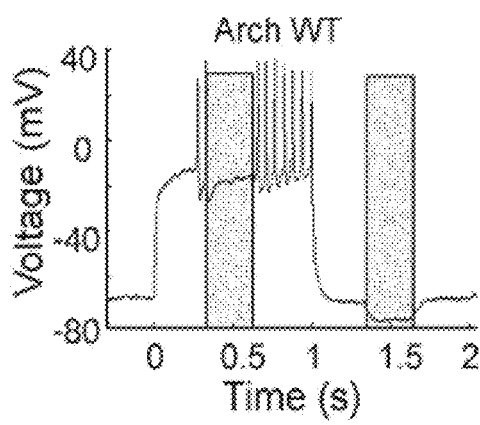
FIG. 5 shows electrically recorded membrane potential of a neuron expressing Arch WT.

FIG. 5 shows electrically recorded membrane potential of a neuron expressing Arch WT, subjected to pulses of current injection and laser illumination (I=1800 W/cm2, λ=640 nm). Illumination generated sufficient photocurrent to suppress action potentials when the cell was near threshold. Grey bars indicate laser illumination.

Figure 6:
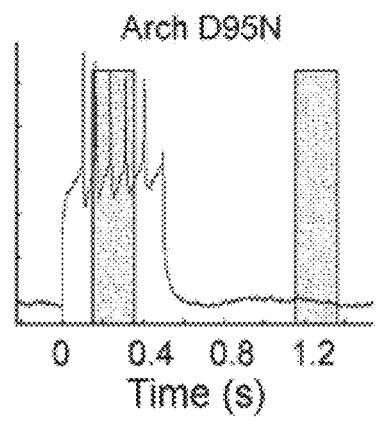
FIG. 6 shows electrically recorded membrane potential of a neuron expressing Arch D95N.

FIG. 6 shows electrically recorded membrane potential of a neuron expressing Arch D95N, showing no effect of illumination on spiking or resting potential. Experiments have shown a neuron expressing Arch D95N, showing Arch D95N fluorescence (shows in cyan in the experiment), and regions of voltage-dependent fluorescence (shown in red in the experiment).

Figure 7:
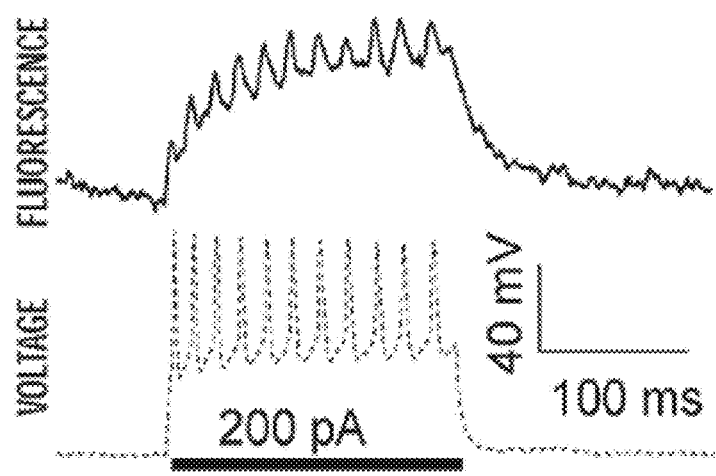
FIG. 7 shows whole-cell membrane potential determined via electrical recording.

FIG. 7 shows whole-cell membrane potential determined via electrical recording (bottom, voltage line) and weighted ArchD95N fluorescence (top, fluorescence line) during a single-trial recording of a train of action potentials. The data represents a single trial, in which spiking was induced by injection of a current pulse. The fluorescence shows clear bursts accompanying individual action potentials. This experiment is the first robust measurement of action potentials in a single mammalian neuron using a genetically encoded voltage indicator.

Figure 8:
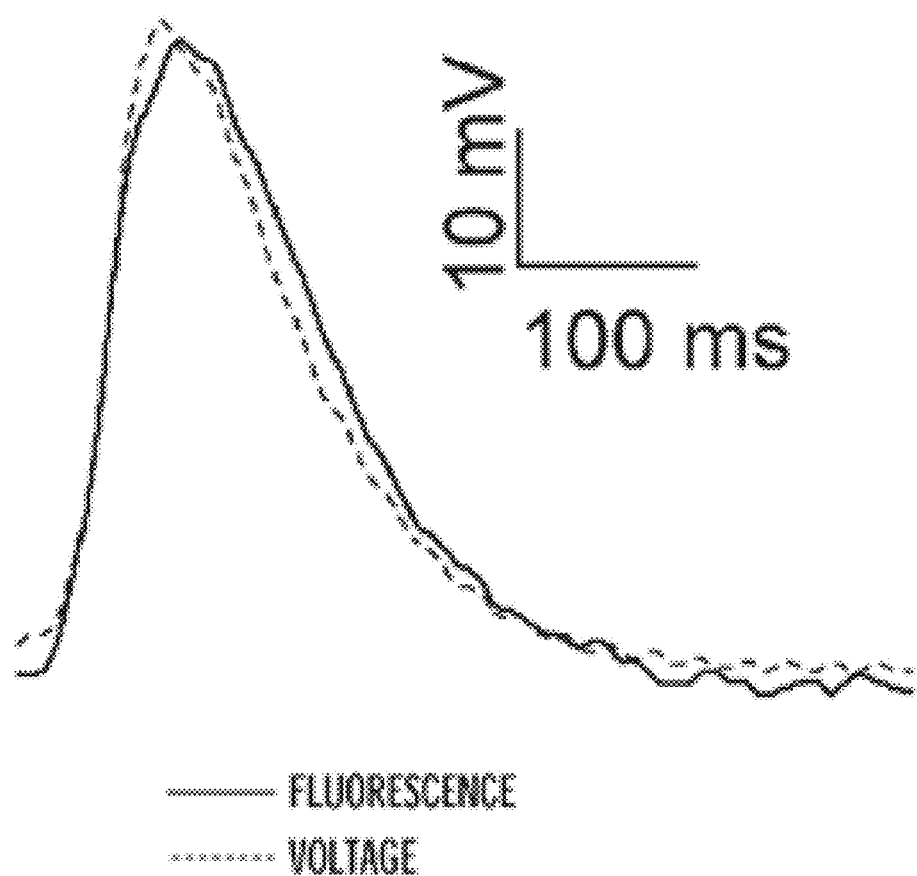
FIG. 8 shows optical recordings of action potentials in a single HL-1 mouse cardiomyocyte expressing Arch 3 D95N-eGFP.

FIG. 8 shows optical recordings of action potentials in a single HL-1 mouse cardiomyocyte expressing Arch 3 D95N-eGFP. Action potentials were recorded for up to 1000 s, with no signs of phototoxicity. This experiment shows quantitative measurement of cardiac action potentials with a genetically encoded voltage indicator. An overlay shows fluorescence of Arch D95N and GFP in a Arch D95N-GFP fusion. FIG. 8 shows a comparison of the action potential determined from patch clamp recording (dashed line) and fluorescence (solid line).

Figure 9:
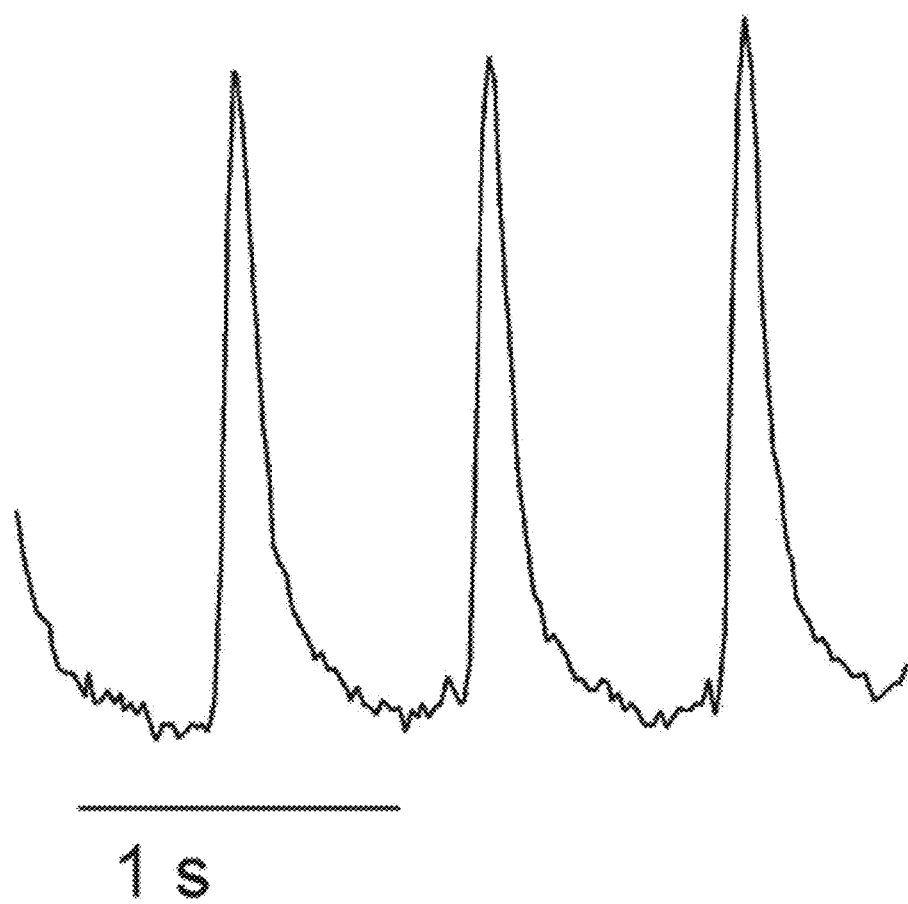
FIG. 9 shows optical recordings of the action potentials in a single HL-1 cell over time.

FIG. 9 shows optical recordings of the action potentials in a single HL-1 cell over time.

Arch and the above-mentioned variants target eukaryotic membranes and can image single action potentials and sub-threshold depolarization in cultured mammalian neurons. See Kralj et al, 2012, Optical recording of action potentials in mammalian neurons using a microbial rhodopsin, Nat Methods 9:90-95. See Hochbaum et al., All-optical electrophysiology in mammalian neurons using engineered microbial rhodopsins, Nature Methods, published online Jun. 22, 2014. Thus Arch and variants of Arch may provide good optical reporters of neural activity according to embodiments of the invention.

The invention provides optical reporters based on Archaerhodopsins that function in mammalian cells, including human stem cell-derived neurons and cardiomyocytes. These proteins indicate electrical dynamics with sub-millisecond temporal resolution and sub-micron spatial resolution and may be used in non-contact, high-throughput, and high-content studies of electrical dynamics in cells and tissues using optical measurement of membrane potential. These reporters are broadly useful, particularly in eukaryotic, such as mammalian, including human cells.

The invention includes reporters based on Archaerhodopsin 3 (Arch 3) and its homologues. Arch 3 is Archaerhodopsin from *H. sodomense* and it is known as a genetically-encoded reagent for high-performance yellow/green-light neural silencing. Gene sequence at GenBank: GU045593.1 (synthetic construct Arch 3 gene, complete cds. Submitted Sep. 28, 2009). These proteins localize to the plasma membrane in eukaryotic cells and show voltage-dependent fluorescence.

Exemplary sequences that can be used to generate virus constructs with Arch 3 include a lentivirus backbone with promoters such as CamKII (excitatory neuron specific); hSynapsin (pan neuronal); CAG enhancer (pan cellular); CMV (pan cellular); Ubiquitin (pan cellular); others; or a combination thereof.

The invention may use optical reporters that include fluorescent voltage indicating proteins such as VSFP 2.3 (Knopfel et al., 2010, Toward the second generation of optogenetic tools, J Neurosci 30:14998-15004), which exhibits a response time of 78 ms and f (where f=(delta F/F per 100 mV)) of 9.5%. VSFP 2.4 (Ibid.) has a 72 ms response time and f of 8.9%. VSFP 3.1 (Lundby et al., 2008, Engineering of a genetically encodable fluorescent voltage sensor exploiting fast Ci-VSP voltage-sensing movements, PLoSOne 3:2514) has a response time of 1-20 ms and a f of 3%. Mermaid is a molecule described in Perron et al., 2009, Second and third generation voltage-sensitive fluorescent proteins for monitoring membrane potential, Front Mol Neurosci 2:1-8 with a response time of 76 and a F of 9.2%. SPARC (Ataka & Pieribone, 2002, Biophys J 82:509-516) response time 0.8 ms and F 0.5%. Flash (Siegel, 1997, Neuron 19:735-741) has response time 2.8-85 ms and f of 5.1%. Arch 3 WT has a response time of 0.6 ms and f of 32%.

Fluorescence recordings may be acquired on an epifluorescence microscope, described in Kralj et al., 2012, Optical recording of action potentials in mammalian neurons using a microbial rhodopsin, Nat. Methods 9:90-95.

Optical reporters of the invention show high sensitivity. In mammalian cells, optical reporters show about 3-fold increase in fluorescence between −150 mV and +150 mV. The response is linear over most of this range. Membrane voltage can be measured with a precision of <1 mV in a 1 s interval. Reporters of the invention show high speed. Arch 3 WT shows 90% of its step response in 0.6 ms. A neuronal action potential lasts approximately 1 ms, so the speeds of Arch indicators meet the benchmark for imaging electrical activity of neurons. Arch 3 WT retains the photo-induced proton-pumping, so illumination slightly hyperpolarizes the cell. Reporters of the invention show high photo-stability and are comparable to GFP in the number of fluorescence photons produced prior to photobleaching. The reporters may also show far red spectrum. The voltage-indicating protein reporters, sometimes referred to as genetically encoded voltage indicators (GE-VIs), may be excited with a laser at wavelengths between 590-640 nm, and the emission is in the near infrared, peaked at 710 nm. The emission is farther to the red than any existing fluorescent protein. These wavelengths coincide with low cellular auto-fluorescence and good transmission through tissue. This feature makes these proteins particularly useful in optical measurements of action potentials as the spectrum facilitates imaging with high signal-to-noise ratio, as well as multi-spectral imaging in combination with other fluorescent probes.

The reporters can be targeted to specific locations or cell types including primary neuronal cultures, cardiomyocytes (HL-1 and human iPSC-derived), HEK cells, and Gram positive and Gram negative bacteria as well as to the endoplasmic reticulum, and to mitochondria. The constructs are useful also for in vivo imaging in *C. elegans*, zebrafish, mice, and rats. Using promoters specific to a particular cell type, time, or both, membrane potential may be imaged in any optically accessible cell type or organelle in a living organism. A reporter may include at least three elements: a promoter, a microbial rhodopsin voltage sensor, one or more targeting motifs, and an optional accessory fluorescent protein. Some non-limiting examples for each of these elements are rhodopsins are given above. Exemplary promoters include CMV, 14x UAS-E1b, HuC, ara, and lac. Exemplary targeting motifs include SS (beta-2nAChR) SS (PPL), ER export motif, TS from Kir2.1, and MS. Exemplary fluorescent proteins include Venus, EYFP, and TagRFP.

In one embodiment, at least one or more rhodopsin, promoter, targeting motif, and fluorescent protein is selected to create an optical voltage sensor with the desired properties. In some embodiments, methods and compositions for voltage sensing as described herein involves selecting: 1) a microbial rhodopsin protein, 2) one or more mutations to imbue the protein with sensitivity to voltage or to other quantities of interest and to eliminate light-driven charge pumping, 3) codon usage appropriate to the host species, 4) a promoter and targeting sequences to express the protein in cell types of interest and to target the protein to the sub-cellular structure of interest, 5) an optional fusion with a conventional fluorescent protein to provide ratiometric imaging, 6) a chromophore to insert into the microbial rhodopsin, and 7) an optical imaging scheme.

In one embodiment, the voltage sensor is selected from a microbial rhodopsin protein (wild-type or mutant) that provides a voltage-induced shift in its absorption or fluorescence. The starting sequences from which these constructs can be engineered include, but are not limited to, the rhodopsins and mutations discussed herein that can be made to the gene to enhance the performance of the protein product.

4b. Optogenetic Actuator

In a preferred embodiment, the cells are transformed with an optical voltage actuator. This can occur, for example, simultaneously with transformation with the vector comprising the optogenetic reporter. The far-red excitation spectrum of certain Arch-based reporters suggests that they may be paired with a blue light-activated channelrhodopsin to achieve all-optical electrophysiology. For spatially precise optical excitation, the channelrhodopsin should carry current densities sufficient to induce action potentials (APs) when only a subsection of a cell is excited. Preferably, light used for imaging the reporter should not activate the actuator, and light used for activating the actuator should not confound the fluorescence signal of the reporter. Thus in a preferred embodiment, an optical actuator and an optical reporter are spectrally orthogonal to avoid crosstalk and allow for simultaneous use. Spectrally orthogonal systems are discussed in Carlson and Campbell, 2013, Circular permutated red fluorescent proteins and calcium ion indicators based on mCherry, Protein Eng Des Sel 26(12):763-772.

Preferably, a genetically-encoded optogenetic actuator is used. One actuator is channelrhodopsin2 H134R, an optogenetic actuator described in Nagel, G. et al., 2005, Light activation of channelrhodopsin-2 in excitable cells of *Caenorhabditis elegans* triggers rapid behavioral responses, Curr Biol 15:2279-2284.

A screen of plant genomes has identified an optogenetic actuator, *Scherffelia dubia* ChR (sdChR), derived from a fresh-water green alga first isolated from a small pond in Essex, England. See Klapoetke et al., 2014, Independent optical excitation of distinct neural populations, Nat Meth Advance Online Publication 1-14; see also Melkonian & Preisig, 1986, A light and electron microscopic study of *Scherffelia dubia*, a new member of the scaly green flagellates (Prasinophyceae). Nord. J. Bot. 6:235-256, both incorporated by reference. SdChR may offer good sensitivity and a blue action spectrum.

An improved version of sdChR dubbed CheRiff may be used as an optical actuator. The gene for *Scherffelia dubia* Channelrhodopsin (sdChR) (selected from a screen of channelrhodopsins for its blue excitation peak (474 nm) and its large photocurrent relative to ChR2) is synthesized with mouse codon optimization, a trafficking sequence from Kir2.1 is added to improve trafficking, and the mutation E154A is introduced. CheRiff exhibits significantly decreased crosstalk from red illumination (to 10.5±2.8 pA) allowing its use in cells along with optogenetic reporters described herein. CheRiff shows good expression and membrane trafficking in cultured rat hippocampal neurons. The maximum photocurrent under saturating illumination (488 nm, 500 mW/cm$^2$) is 2.0±0.1 nA (n=10 cells), approximately 2-fold larger than the peak photocurrents of ChR2H134R or ChIEF (Lin et al., 2009, Characterization of engineered channelrhodopsin variants with improved properties and kinetics, Biophys J 96:1803-1814). In neurons expressing CheRiff, whole-cell illumination at only 22±10 mW/cm$^2$ induces a photocurrent of 1 nA. Compared to ChR2H134R and to ChIEF under standard channelrhodopsin illumination conditions (488 nm, 500 mW/cm$^2$). At 23° C., CheRiff reaches peak photocurrent in 4.5±0.3 ms (n=10 cells). After a 5 ms illumination pulse, the channel closing time constant was comparable between CheRiff and ChIEF (16±0.8 ms, n=9 cells, and 15±2 ms, n=6 cells, respectively, p=0.94), and faster than ChR2H134R (25±4 ms, n=6 cells, p<0.05). Under continuous illumination CheRiff partially desensitizes with a time constant of 400 ms, reaching a steady-state current of 1.3±0.08 nA (n=10 cells). Illumination of neurons expressing CheRiff induces trains of APs with high reliability and high repetition-rate.

When testing for optical crosstalk between Arch-based reporters and CheRiff in cultured neurons, illumination sufficient to induce high-frequency trains of APs (488 nm, 140 mW/cm$^2$) perturbed fluorescence of reporters by <1%. Illumination with high intensity red light (640 nm, 900 W/cm$^2$) induced an inward photocurrent through CheRiff of 14.3±3.1 pA, which depolarized neurons by 3.1±0.2 mV (n=5 cells). ChIEF and ChR2 H134R generated similar red light photocurrents and depolarizations. For most applications this level of optical crosstalk is acceptable.

4c. Vectors for Expression of Optogenetic Systems

The optogenetic reporters and actuators may be delivered in constructs described here as Optopatch constructs delivered through the use of an expression vector. Optopatch may be taken to refer to systems that perform functions traditionally associated with patch clamps, but via an optical input, readout, or both as provided for by, for example, an optical reporter or actuator. An Optopatch construct may include a bicistronic vector for co-expression of CheRiff-eGFP and a reporter (e.g., a suitable Arch-based reporter such as Arch D95N). The reporter and CheRiff constructs may be delivered separately, or a bicistronic expression vector may be used to obtain a uniform ratio of actuator to reporter expression levels.

The genetically encoded reporter, actuator, or both may be delivered by any suitable expression vector using methods known in the art. An expression vector is a specialized vector that contains the necessary regulatory regions needed for expression of a gene of interest in a host cell. Examples of vectors include plasmids (e.g. pBADTOPO, pCI-Neo, pcDNA3.0), cosmids, and viruses (such as a lentivirus, an adeno-associated virus, or a baculovirus). In some embodiments the gene of interest is operably linked to another sequence in the vector. In some embodiments, it is preferred that the viral vectors are replication defective, which can be achieved for example by removing all viral nucleic acids that encode for replication. A replication defective viral vector will still retain its infective properties and enters the cells in a similar manner as a replicating vector, however once admitted to the cell a replication defective viral vector does not reproduce or multiply. The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

Many viral vectors or virus-associated vectors are known in the art. Such vectors can be used as carriers of a nucleic acid construct into the cell. Constructs may be integrated and packaged into non-replicating, defective viral genomes like Adenovirus, Adeno-associated virus (AAV), serotypes of AAV that include AAV1-AAV9, or Herpes simplex virus (HSV) or others, including retroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, such as an Epstein Barr virus (EPV or EBV) vector. The inserted material of the vectors described herein may be operatively linked to an expression control sequence when the expression control sequence controls and regulates the transcription and translation of that polynucleotide sequence. In some examples, transcription of an inserted material is under the control of a promoter sequence (or other transcriptional regulatory sequence) which controls the expression of the recombinant gene. In some embodiments, a recombinant cell containing an inducible promoter is used and exposed to a regulatory agent or stimulus by externally applying the agent or stimulus to the cell or organism by exposure to the appropriate environmental condition or the operative pathogen. Inducible promoters initiate transcription only in the presence of a regulatory agent or stimulus. Examples of inducible promoters include the tetracycline response element and promoters derived from the beta-interferon gene, heat shock gene, metallothionein gene or any obtainable from steroid hormone-responsive genes. Inducible promoters which may be used in performing the methods of the present invention include those regulated by hormones and hormone analogs such as progesterone, ecdysone and glucocorticoids as well as promoters which are regulated by tetracycline, heat shock, heavy metal ions, interferon, and lactose operon activating compounds. See Gingrich and Roder, 1998, Inducible gene expression in the nervous system of transgenic mice, Annu Rev Neurosci 21:377-405. Tissue specific expression has been well characterized in the field of gene expression and tissue specific and inducible promoters are well known in the art. These promoters are used to regulate the expression of the foreign gene after it has been introduced into the target cell. In certain embodiments, a cell-type specific promoter or a tissue-specific promoter is used. A cell-type specific promoter may include a leaky cell-type specific promoter, which regulates expression of a selected nucleic acid primarily in one cell type, but cause expression in other cells as well. For expression of an exogenous gene specifically in neuronal cells, a neuron-specific enolase promoter can be used. See Forss-Petter et al., 1990, Transgenic mice expressing beta-galactosidase in mature neurons under neuron-specific enolase promoter control, Neuron 5(2):187-197.

Suitable delivery methods include viral and non-viral vectors, as well as biological or chemical methods of transfection. The methods can yield either stable or transient gene expression in the system used. In some embodiments, a viral vector such as an (i) adenovirus, (ii) adeno-associated virus, (iii) retrovirus, (iv) lentivirus, or (v) other is used.

(i) Adenovirus

Adenoviruses are double stranded, non-enveloped and icosahedral viruses containing a 36 kb viral genome (Kojaoghlanian et al., 2003, The impact of adenovirus infection on the immunocompromised host, Rev Med Virol 13:155-171). Their genes are divided into early (E1A, E1B, E2, E3, E4), delayed (IX, IVa2) and major late (L1, L2, L3, L4, L5) genes depending on whether their expression occurs before or after DNA replication. More than 51 human adenovirus serotypes have been described which can infect and replicate in a wide range of organs. These viruses have been used to generate a series of vectors for gene transfer cellular engineering. The initial generation of adenovirus vectors were produced by deleting the E1 gene (required for viral replication) generating a vector with a 4 kb cloning capacity. An additional deletion of E3 (responsible for host immune response) allowed an 8 kb cloning capacity (Bett et al., 1994, An efficient and flexible system for construction of adenovirus vectors with insertions or deletions in early regions 1 and 3, PNAS 91:8802-8806; Danthinne and Imperiale, 2000, Production of first generation adenovirus vector, a review, Gene Ther 7:1707-1714). The second generation of vectors was produced by deleting the E2 region (required for viral replication) and/or the E4 region (participating in inhibition of host cell apoptosis) in conjunction with E1 or E3 deletions. The resultant vectors have a cloning capacity of 10-13 kb (Armentano et al., 1995, Characterization of an adenovirus gene transfer vector containing an E4 deletion, Hum Gen Ther 6(10):1343-1353). The third "gutted" generation of vectors was produced by deletion of the entire viral sequence with the exception of the inverted terminal repeats (ITRs) and the cis acting packaging signals. These vectors have a cloning capacity of 25 kb (Kochanek et al., 2001, High-capacity "gutless" adenoviral vectors, Curr Op Mol Ther 3:454-463) and have retained their high transfection efficiency both in quiescent and dividing cells.

Importantly, the adenovirus vectors do not normally integrate into the genome of the host cell, but they have shown efficacy for transient gene delivery into adult stem cells. These vectors have a series of advantages and disadvantages. An important advantage is that they can be amplified at high titers and can infect a wide range of cells. The vectors are generally easy to handle due to their stability in various storing conditions. Adenovirus type 5 (Ad5) has been successfully used in delivering genes in human and mouse stem cells and without integration generally provides transient expression.

(ii) Adeno-Associated Virus

Adeno-Associated viruses (AAV) are ubiquitous, noncytopathic, replication-incompetent members of ssDNA animal virus of parvoviridae family (Gao et al., 2005, New recombinant serotypes of AAV vectors, Curr Gene Ther 5 (3):285-97). AAV is a small icosahedral virus with a 4.7 kb genome. These viruses have a characteristic termini consisting of palindromic repeats that fold into a hairpin. They replicate with the help of helper virus, which are usually one of the many serotypes of adenovirus. In the absence of helper virus they integrate into the human genome at a specific locus (AAVS1) on chromosome 19 and persist in latent form until helper virus infection occurs. AAV can transduce cell types from different species including mouse, rat and monkey. These viruses are similar to adenoviruses in that they are able to infect a wide range of dividing and non-dividing cells. Unlike adenovirus, they have the ability to integrate into the host genome at a specific site in the human genome.

In some embodiments the viral vector is an adeno-associated virus (AAV) vector. AAV can infect both dividing and non-dividing cells and may incorporate its genome into that of the host cell. One suitable viral vector uses recombinant adeno-associated virus (rAAV), which is widely used for gene delivery in the CNS. In certain embodiments, the vector may use AAV serotype 9 (AAV9). See Bell et al., 2011, The AAV9 receptor and its modification to improve in vivo lung gene transfer in mice, J Clin Invest 121(6):2427-2435; and Cearley & Wolfe, 2006, Transduction characteristics of adeno-associated virus vectors expressing cap serotypes 7, 8, 9, and Rh10 in the mouse brain, Mol Ther 13:528-537; and Foust et al., 2009, Intravascular AAV9 preferentially targets neonatal neurons and adult astrocytes, Nat Biotechnol 27:59-65.

(ii) Retroviruses

Retroviral genomes consist of two identical copies of single stranded positive sense RNAs, 7-10 kb in length coding for three genes; gag, pol and env, flanked by long terminal repeats (LTR) (Yu & Schaffer, 2006, Engineering retroviral and lentiviral vectors by selection of a novel peptide insertion library for enhanced purification, J. Virol. 80:3285-3292). The gag gene encodes the core protein capsid containing matrix and nucleocapsid elements that are cleavage products of the gag precursor protein. The pol gene codes for the viral protease, reverse transcriptase and integrase enzymes derived from gag-pol precursor gene. The env gene encodes the envelop glycoprotein which mediates viral entry. An important feature of the retroviral genome is the presence of LTRs at each end of the genome. These sequences facilitate the initiation of viral DNA synthesis, moderate integration of the proviral DNA into the host genome, and act as promoters in regulation of viral gene transcription. Retroviruses are subdivided into three general groups: the oncoretroviruses (Maloney Murine Leukenmia Virus, MoMLV), the lentiviruses (HIV), and the spumaviruses (foamy virus). Retroviral based vectors are the most commonly used integrating vectors for gene therapy. These vectors generally have a cloning capacity of approximately 8 kb and are generated by a complete deletion of the viral sequence with the exception of the LTRs and the cis acting packaging signals.

(ii) Lentivirus

Lentiviruses are members of Retroviridae family of viruses (Scherr et al., 2002, Gene transfer into hematopoietic stem cells using lentiviral vectors, Curr Gene Ther. 2(1):45-55). They have a more complex genome and replication cycle as compared to the oncoretroviruses (Beyer et al., 2002, Oncoretrovirus and lentivirus vectors pseudotyped with lymphocytic choriomeningitis virus glycoprotein: generation, concentration, and broad host range, J. Virol 76:1488-1495). They differ from simpler retroviruses in that they possess additional regulatory genes and elements, such as the tat gene, which mediates the transactivation of viral transcription and rev, which mediates nuclear export of un-spliced viral RNA. See also U.S. Pat. No. 5,665,577 to Sodroski, the contents of which are incorporated by reference.

Lentivirus vectors are derived from the human immunodeficiency virus (HIV-1) by removing the genes necessary for viral replication rendering the virus inert. Although they are devoid of replication genes, the vector can still efficiently integrate into the host genome allowing stable expression of the transgene. These vectors have the additional advantage of a low cytotoxicity and an ability to infect diverse cell types.

Lentiviral vectors may include a eukaryotic promoter. The promoter can be any inducible promoter, including synthetic promoters, that can function as a promoter in a eukaryotic cell. For example, the eukaryotic promoter can be, but is not limited to, CamKIIa promoter, human Synapsin promoter, ecdysone inducible promoters, E1a inducible promoters, tetracycline inducible promoters etc., as are well known in the art. In addition, the lentiviral vectors used herein can further comprise a selectable marker, which can comprise a promoter and a coding sequence for a selectable trait. Nucleotide sequences encoding selectable markers are well known in the art, and include those that encode gene products conferring resistance to antibiotics or anti-metabolites, or that supply an auxotrophic requirement. Examples of such sequences include, but are not limited to, those that encode thymidine kinase activity, or resistance to methotrexate, ampicillin, kanamycin, among others. Use of lentiviral vectors is discussed in Wardill et al., 2013, A neuron-based screening platform for optimizing genetically-encoded calcium indicators, PLoS One 8(10):e77728; Dottori, et al., Neural development in human embryonic stem cells-applications of lentiviral vectors, J Cell Biochem 112(8):1955-62; and Diester et al., 2011, An optogenetic toolbox designed for primates, Nat Neurosci 14(3):387-97. When expressed under a CaMKIIα promoter in cultured rat hippocampal neurons the Optopatch construct exhibits high expression and good membrane trafficking of both CheRiff and a reporter.

In certain embodiments, genetic material is delivered by a non-viral method. Non-viral methods include plasmid transfer, modified RNA, and the application of targeted gene integration through the use of integrase or transposase technologies. Exemplary recombinase systems include: cre recombinase from phage P1 (Lakso et al., 1992, Targeted oncogene activation by site-specific recombination in transgenic mice, PNAS 89:6232-6236; Orban et al., 1992, Tissue- and site-specific DNA recombination in transgenic mice, PNAS 89:6861-6865), FLP (flippase) from yeast 2 micron plasmid (Dymecki, 1998, Using Flp-recombinase to characterize expansion of Wnt1-expressing neural progenitors in the mouse, Dev Biol 201:57-65), and an integrase isolated from streptomyses phage I C31 (Groth et al., 2000, A phage integrase directs efficient site-specific integration in human cells, PNAS 97(11):5995-6000). Each of these recombinases recognize specific target integration sites. Cre and FLP recombinase catalyze integration at a 34 bp palindromic sequence called lox P (locus for crossover) and FRT (FLP recombinase target) respectively. Phage integrase catalyzes site-specific, unidirectional recombination between two short att recognition sites in mammalian genomes. Recombination results in integration when the att sites are present on two different DNA molecules and deletion or inversion when the att sites are on the same molecule. It has been found to function in tissue culture cells (in vitro) as well as in mice (in vivo).

The Sleeping Beauty (SB) transposon is comprised of two inverted terminal repeats of 340 base pairs each (Izsvak et al., 2000, Sleeping Beauty, a wide host-range transposon vector for genetic transformation in vertebrates, J Mol Biol 302(1): 93-102). This system directs the precise transfer of specific constructs from a donor plasmid into a mammalian chromosome. The excision and integration of the transposon from a plasmid vector into a chromosomal site is mediated by the SB transposase, which can be delivered to cells as either in a cis or trans manner (Kaminski et al., 2002, Design of a nonviral vector for site-selective, efficient integration into the human genome, FASEB J 6:1242-1247). A gene in a chromosomally integrated transposon can be expressed over the lifetime of a cell. SB transposons integrate randomly at TA-dinucleotide base pairs although the flanking sequences can influence integration.

In certain embodiments, methods of the invention use a Cre-dependent expression system. Cre-dependent expression includes Cre-Lox recombination, a site-specific recombinase technology that uses the enzyme Cre recombinase, which recombines a pair of short target sequences called the Lox sequences. This system can be implemented without inserting any extra supporting proteins or sequences. The Cre enzyme and the original Lox site called the LoxP sequence are derived from bacteriophage P1. Bacteriophage P1 uses Cre-lox recombination to circularize and replicate its genomic DNA.

This recombination strategy is employed in Cre-Lox technology for genome manipulation, which requires only the Cre recombinase and LoxP sites. Sauer & Henderson, 1988, Site-specific DNA recombination in mammalian cells by the Cre recombinase of bacteriophage P1, PNAS 85:5166-70 and Sternberg & Hamilton, 1981, Bacteriophage P1 site-specific recombination. I. Recombination between LoxP sites, J Mol Biol 150:467-86. Methods may use a Cre recombinase-dependent viral vector for targeting tools such as channelrhodopsin-2 (ChR2) to specific neurons with expression levels sufficient to permit reliable photostimulation. Optogenetic tools such as ChR2 tagged with a fluorescent protein such as mCherry (e.g., ChR2mCherry) or any other of the tools discussed herein are thus delivered to the cell or cells for use in characterizing those cells.

The delivery vector may include Cre and Lox. The vector may further optionally include a Lox-stop-Lox (LSL) cassette to prevent expression of the transgene in the absence of Cre-mediated recombination. In the presence of Cre recombinase, the LoxP sites recombine, and a removable transcription termination Stop element is deleted. Removal of the stop element may be achieved through the use of AdenoCre, which allows control of the timing and location of expression. Use of the LSL cassette is discussed in Jackson, et al., 2001, Analysis of lung tumor initiation and progression using conditional expression of oncogenic K-ras, Genes & Dev 15:3243-3248.

In certain embodiments, a construct of the invention uses a "flip-excision" switch, or FLEX switch (FLip EXicision), to achieve stable transgene inversion. The FLEX switch is discussed in Schnutgen et al., 2003, A directional strategy for monitoring Cre-mediated recombination at the cellular level in the mouse, Nat Biotechnol 21:562-565. The FLEX switch uses two pairs of heterotypic, antiparallel LoxP-type recombination sites which first undergo an inversion of the coding sequence followed by excision of two sites, leading to one of each orthogonal recombination site oppositely oriented and incapable of further recombination. A FLEX switch provides high efficiency and irreversibility. Thus in some embodiments, methods use a viral vector comprising rAAV-FLEX-rev-ChR2mCherry. Additionally or alternatively, a vector may include FLEX and any other optogenetic tool discussed herein (e.g., rAAV-FLEX-Arch D95N, rAAV-FLEX-CheRiff). Using rAAV-FLEX-rev-ChR2mCherry as an illustrative example, Cre-mediated inversion of the ChR2mCherry coding sequence results in the coding sequence being in the wrong orientation (i.e., rev-ChR2mCherry) for transcription until Cre inverts the sequence, turning on transcription of ChR2mCherry. FLEX switch vectors are discussed in Atasoy et al., 2009, A FLEX switch targets channelrhodopsin-2 to multiple cell types for imaging and long-range circuit mapping, J Neurosci 28(28):7025-7030.

Use of a viral vector such as Cre-Lox system with an optical reporter, optical actuator, or both (optionally with a FLEX switch and/or a Lox-Stop-Lox cassette) for labeling and stimulation of neurons allows for efficient photo-stimulation with only brief exposure (1 ms) to less than 100 μLW focused laser light or to light from an optical fiber. Such Further discussion may be found in Yizhar et al., 2011, Optogenetics in neural systems, Neuron 71(1):9-34; Cardin et al., 2010, Targeted optogenetic stimulation and recording of neurons in vivo using cell-type-specific expression of Channelrhodopsin-2, Nat Protoc 5(2):247-54; Rothermel et al., 2013, Transgene expression in target-defined neuron populations mediated by retrograde infection ith adeno-associated viral vectors, J Neurosci 33(38):195-206; and Saunders et al., 2012, Novel recombinant adeno-associated viruses for Cre activated and inactivated transgene expression in neurons, Front Neural Circuits 6:47.

In certain embodiments, actuators, reporters, or other genetic material may be delivered using chemically-modified mRNA. It may be found and exploited that certain nucleotide modifications interfere with interactions between mRNA and toll-like receptor, retinoid-inducible gene, or both. Exposure to mRNAs coding for the desired product may lead to a desired level of expression of the product in the cells. See, e.g., Kormann et al., 2011, Expression of therapeutic proteins after delivery of chemically modified mRNA in mice, Nat Biotech 29(2):154-7; Zangi et al., 2013, Modified mRNA directs the fate of heart progenitor cells and induces vascular regeneration after myocardial infarction, Nat Biotech 31:898-907.

It may be beneficial to culture or mature the cells after transformation with the genetically encoded optical reporter with optional actuator. In some embodiments, the neurons are matured for 8-10 days post infection. Using microscopy and analytical methods described herein, the cell and its action potentials may be observed. For additional discussion, see U.S. Pub. 2013/0224756, incorporated by reference in its entirety for all purposes.

Other methods for transfection include physical methods such as electroporation as well as methods that employ biomolecules.

Electroporation relies on the use of brief, high voltage electric pulses which create transient pores in the membrane by overcoming its capacitance. One advantage of this method is that it can be utilized for both stable and transient gene expression in most cell types. The technology relies on the relatively weak nature of the hydrophobic and hydrophilic interactions in the phospholipid membrane and its ability to recover its original state after the disturbance. Once the membrane is permeabilized, polar molecules can be delivered into the cell with high efficiency. Large charged molecules like DNA and RNA move into the cell through a process driven by their electrophoretic gradient.

Biomolecule-based methods include the use of protein transduction domains (PTD). PTDs are short peptides that are transported into the cell without the use of the endocytotic pathway or protein channels. The mechanism involved in their entry is not well understood, but it can occur even at low temperature (Derossi et al., 1996, J Biol Chem 271(30):18188-93). The two most commonly used naturally occurring PTDs are the trans-activating activator of transcription domain (TAT) of human immunodeficiency virus and the homeodomain of Antennapedia transcription factor. In addition to these naturally occurring PTDs, there are a number of artificial peptides that have the ability to spontaneously cross the cell membrane (Joliot and Prochiantz, 2004, Transduction peptides: from technology to physiology, Nat Cell Biol 6(3): 189-96). These peptides can be covalently linked to the pseudo-peptide backbone of PNA (peptide nucleic acids) to help deliver them into the cell.

Additionally or alternatively, liposomes may be used. Liposomes are synthetic vesicles that resemble the cell membrane. When lipid molecules are agitated with water they spontaneously form spherical double membrane compartments surrounding an aqueous center forming liposomes. They can fuse with cells and allow the transfer of "packaged" material into the cell. Liposomes have been successfully used to deliver genes, drugs, reporter proteins and other biomolecules into cells (Felnerova et al., 2004, Liposomes and virosomes as delivery systems for antigens, nucleic acids and drugs, Curr Opin Biotech 15: 518-529). The advantage of liposomes is that they are made of natural biomolecules (lipids) and are nonimmunogenic.

Diverse hydrophilic molecules can be incorporated into them during formation. For example, when lipids with positively charged head group are mixed with recombinant DNA they can form lipoplexes in which the negatively charged DNA is complexed with the positive head groups of lipid molecules. These complexes can then enter the cell through the endocytotic pathway and deliver the DNA into lysosomal compartments. The DNA molecules can escape this compartment with the help of dioleoylethanolamine (DOPE) and are transported into the nucleus where they can be transcribed (Tranchant et al., 2004, Physicochemical optimisation of plasmid delivery by cationic lipids, J Gene Med 6 Suppl 1:S24-35).

Immunoliposomes are liposomes with specific antibodies inserted into their membranes. The antibodies bind selectively to specific surface molecules on the target cell to facilitate uptake. The surface molecules targeted by the antibodies are those that are preferably internalized by the cells so that upon binding, the whole complex is taken up. This approach increases the efficiency of transfection by enhancing the intracellular release of liposomal components. These antibodies can be inserted in the liposomal surface through various lipid anchors or attached at the terminus of polyethylene glycol grafted onto the liposomal surface. In addition to providing specificity to gene delivery, the antibodies can also provide a protective covering to the liposomes that helps to limit their degradation after uptake by endogenous RNAses or proteinases (Bendas, 2001, Immunoliposomes: A promising approach to targeting cancer therapy, BioDrugs 15(4): 215-224). To further prevent degradation of liposomes and their contents in the lysosomal compartment, pH sensitive immunoliposomes can be employed (Torchilin et al., 2006, pH-sensitive liposomes, J Liposome Res 3:201-255). These liposomes enhance the release of liposomal content into the cytosol by fusing with the endosomal membrane within the organelle as they become destabilized and prone to fusion at acidic pH.

In general, non-viral gene delivery systems have not been as widely applied as a means of gene delivery into stem cells as viral gene delivery systems. However, promising results are demonstrated in a study looking at the transfection viability, proliferation and differentiation of adult neural stem/progenitor cells into the three neural lineages neurons. Non-viral, non-liposomal gene delivery systems (ExGen500 and FuGene6) had a transfection efficiency of between 16% (ExGen500) and 11% (FuGene6) of cells. FuGene6-treated cells did not differ from untransfected cells in their viability or rate of proliferation, whereas these characteristics were significantly reduced following ExGen500 transfection. Importantly, neither agent affected the pattern of differentiation following transfection. Both agents could be used to genetically label cells, and track their differentiation into the three neural lineages, after grafting onto ex vivo organotypic hippocampal slice cultures (Tinsley et al, 2006, Efficient non-viral transfection of adult neural stem/progenitor cells, without affecting viability, proliferation or differentiation, J Gene Med 8(1):72-81).

(iv) Polymer-Based Methods

The protonated epsilon-amino groups of poly L-lysine (PLL) interact with the negatively charged DNA molecules to form complexes that can be used for gene delivery. These complexes can be rather unstable and showed a tendency to aggregate. The conjugation of polyethylene glycol (PEG) was found to lead to an increased stability of the complexes.

To confer a degree of tissue-specificity, targeting molecules such as tissue-specific antibodies have also been employed. An additional gene carrier that has been used for transfecting cells is polyethylenimine (PEI) which also forms complexes with DNA. Due to the presence of amines with different pKa values, it has the ability to escape the endosomal compartment. PEG grafted onto PEI complexes was found to reduce the cytotoxicity and aggregation of these complexes. This can also be used in combination with conjugated antibodies to confer tissue-specificity. See Lee & Kim, 2014, Bioreducible polymers for therapeutic gene delivery, J Control Relase ePub; Wang et al., 2013, Non-viral gene delivery methods, Curr Pharm Biotechnol 14(1):46-40; and Gupta et al., 2012, Structuring polymers for delivery of DNA-based therapeutics: updated insights, Crit. Rev Ther Drug Carrier Syst 29(6): 447-85.

Optical actuators, reporters, or both as discussed herein may be targeted to intracellular organelles, including mitochondria, the endoplasmic reticulum, the sarcoplasmic reticulum, synaptic vesicles, and phagosomes. Accordingly, in one embodiment, the invention provides expression constructs, such as viral constructs comprising a reporter and/or actuatory operably linked to a sequence targeting the protein to an intracellular organelle, including a mitochondrion, an endoplasmic reticulum, a sarcoplasmic reticulum, a synaptic vesicle, and a phagosome. In some embodiments, the optical voltage sensor further comprises a localization or targeting sequence to direct or sort the sensor to a particular face of a biological membrane or subcellular organelle. Preferred localization sequences provide for highly specific localization of the protein, with minimal accumulation in other subcellular compartments. Localization signals are described in, e.g., "Protein Targeting", chapter of Stryer, L., Biochemistry (4th ed.). W. H. Freeman, 1995 and Chapter 12 (pages 551-598) of Molecular Biology of the Cell, Alberts et al. third edition, (1994) Garland Publishing Inc. In some embodiments, more than one discrete localization motif is used to provide for correct sorting by the cellular machinery. For example, correct sorting of proteins to the extracellular face of the plasma membrane can be achieved using an N-terminal signal sequence and a C-terminal GPI anchor or transmembrane domain.

Typically, localization sequences can be located almost anywhere in the amino acid sequence of the protein. In some cases the localization sequence can be split into two blocks separated from each other by a variable number of amino acids. The creation of such constructs via standard recombinant DNA approaches is well known in the art, as for example described in Maniatis, et al., Molecular Cloning A Laboratory Manual, Cold Spring Harbor Laboratory, N.Y, 1989).

Methods of the invention can be used to express proteins transiently, stably, or both. Transduction and transformation methods for transient expression of nucleic acids are well known to one skilled in the art. Transient transfection can be carried out, e.g., using calcium phosphate, by electroporation, or by mixing a cationic lipid with the material to produce liposomes, cationic polymers or highly branched organic compounds. All these are in routine use in genetic engineering.

Exemplary protocols for stable expression can be found, e.g., in Essential Stem Cell Methods, edited by Lanza and Klimanskaya, published in 2008, Academic Press. For example, one can generate a virus that integrates into the genome and comprises a selectable marker, and infect the cells with the virus and screen for cells that express the marker, which cells are the ones that have incorporated the virus into their genome. A VSV-g psuedotyped lenti virus with a puromycin selectable marker in HEK cells can be used according to established procedures. Generally, one can use a stem cell specific promoter to encode a GFP if FACS sorting is necessary. The hiPS cultures are cultivated on embryonic fibroblast (EF) feeder layers or on Matrigel in fibroblast growth factor supplemented EF conditioned medium. The cells are dissociated by trypsinization, plated, and maintained in an undifferentiated state, e.g., using EF conditioned medium. Cells are cultured with the virus for 24 hours; washed, typically with PBS, and fresh media is added with a selection marker, such as 1 micro g/mL puromycin. The medium is replaced about every 2 days with additional puromycin. Cells surviving after 1 week are re-plated, e.g., using the hanging drop method to form EBs with stable incorporation of gene.

In some embodiments, it is advantageous to express an optical voltage reporter (e.g., Arch D95N or a suitable variant thereof) in only a single cell-type within an organism, and further, if desired, to direct the reporter to a particular subcellular structure within the cell. Upstream promoters control when and where the gene is expressed. Constructs are made that optimize expression in all eukaryotic cells. In one embodiment, the optical voltage sensor is under the control of a neuron-specific promoter.

The promoter sequence can be selected to restrict expression of the protein to a specific class of cells and environmental conditions. Common promoter sequences include, but are not limited to, CMV (cytomegalovirus promoter; a universal promoter for mammalian cells), 14×UAS-E1b (in combination with the transactivator Gal4, this promoter allows combinatorial control of transgene expression in a wide array of eukaryotes. Tissue-specific expression can be achieved by placing Gal4 under an appropriate promoter, and then using Gal4 to drive the UAS-controlled transgene), HuC (drives pan-neuronal expression in zebrafish and other teleosts), ara (allows regulation of expression with arabinose in bacteria) and lac (allows regulation of expression with IPTG in bacteria).

Methods of the invention can be used to target actuators, reporters, or both to specific cellular sites such as the plasma membrane. In some embodiments, constructs are designed to include signaling sequences to optimize localization of the protein to the plasma membrane. These can include e.g., a C-terminal signaling sequence from the $O._2$ nicotinic acetylcholine receptor and/or an endoplasmic reticulum export motif from Kir2.1.

Additional improvements in plasma localization can be obtained by adding Golgi export sequences and membrane localization sequences. See Gong et al., 2014, Imaging neural spiking in brain tissue using FRET-opsin protein voltage sensors, Nat Comm 5:articel3674; and Gradinaru et al., 2010, Molecular and Cellular Approaches for Diversifying and Extending Optogenetics, *Cell* 141:154-165. In some embodiments, the targeting sequence is selected to regulate intracellular transport of the protein to the desired subcellular structure. In one embodiment the protein is targeted to the plasma membrane of a eukaryotic cell. In this case the targeting sequence can be designed following the strategy outlined in e.g., Gradinaru 2010. The term "signal sequence" refers to N-terminal domains that target proteins into a subcellular locale e.g., the endoplasmic reticulum (ER), and thus are on their way to the plasma membrane. Signal sequences used in optogenetic voltage sensors can be derived from the proteins beta-2-n-acetylcholine receptor (SS B2nAChR) and PPL. In addition, there is an endogenous signaling sequence on microbial rhodopsin proteins that can be harnessed for appropriate subcellular targeting. A trafficking signal (TS) can optionally be inserted into the genome C-terminal to the microbial rhodopsin and N-terminal to the accessory fluorescent protein. In one embodiment, the trafficking signal is derived from the Kir2.1 protein as specified in Gradinaru et al. In another embodiment, an ER export motif is inserted at the C-terminus of the accessory fluorescent protein.

A construct of the invention may be localized to the mitochondrial inner membrane or mitochondrial outer membrane, i.e., using appropriate signaling sequences added to the rhodopsin protein. Optogenetic reporters can be targeted to the inner mitochondrial membrane as that described in Hoffmann et al., 1994, Photoactive mitochondria: in vivo transfer of a light-driven proton pump into the inner mitochondrial membrane of *Schizosaccharomyces pombe*, PNAS 91:9367-9371.

As discussed above, the invention includes optogenetic reporters, optogenetic actuators, and vectors for the expression of microbial rhodopsins. See also U.S. Pat. No. 8,716,447 to Deisseroth; U.S. Pat. No. 8,647,870 to Hegemann; U.S. Pat. No. 8,617,876 to Farrar; U.S. Pat. No. 8,603,790 to Deisseroth; U.S. Pat. No. 8,580,937 to Spudich; U.S. Pat. No. 8,562,658 to Shoham; and U.S. Pat. No. 8,202,699 to Hegemann, the contents of each of which are incorporated by reference.

The invention further provides cells expressing the constructs, and further methods of measuring membrane potential changes in the cells expressing such constructs as well as methods of screening for agents that affect the membrane potential of one or more of the intracellular membranes.

5. Imaging Activity Assay

5a. Capturing Images

Methods of the invention may include stimulating the cells that are to be observed. Stimulation may be direct or indirect (e.g., optical stimulation of an optical actuator or stimulating an upstream cell in synaptic or gap junction-mediated communication with the cell(s) to be observed). Stimulation may be optical, electrical, chemical, or by any other suitable method. Stimulation may involve any pattern of a stimulation including, for example, regular, periodic pulses, single pulses, irregular patterns, or any suitable pattern. Methods may include varying optical stimulation patterns in space or time to highlight particular aspects of cellular function. For example, a pulse pattern may have an increasing frequency. In certain embodiments, imaging includes stimulating a neuron that expresses an optical actuator using pulses of light.

Optical reporters of the invention provide accurate values of the membrane potential, without systematic artifacts from photobleaching, variation in illumination intensity, cell movement, or variations in protein expression level. In cells that are accessible to patch clamp, one can calibrate the fluorescence as a function of membrane potential by varying the membrane potential under external control. However, constructs of the invention function in systems that are inaccessible to patch clamp. In these cases direct calibration is not possible.

The Arch 3 fusion with eGFP enables ratiometric determination of membrane potential. Similar ratiometric determinations may be made using other optical reporters such as those described in this application using the identical concept. The eGFP fluorescence is independent of membrane potential, The ratio of Arch 3 fluorescence to eGFP fluorescence provides a measure of membrane potential that is independent of variations in expression level, illumination, or movement.

In the methods of the invention, the cells are excited with a light source so that the emitted fluorescence can be detected. The wavelength of the excitation light depends on the fluorescent molecule. For example, the Archaerhodopsin constructs in the examples are all excitable using light with wavelengths varying between lambda=594 nm and lambda=645 nm. Alternatively, the range may be between lambda=630-645 nm. For example a commonly used Helium Neon laser emits at lambda=632.8 nm and can be used in excitation of the fluorescent emission of these molecules.

In some embodiments a second light is used. For example, if the cell expresses a reference fluorescent molecule or a fluorescent molecule that is used to detect another feature of the cell, such a pH or Calcium concentration. In such case, the second wavelength differs from the first wavelength. Examples of useful wavelengths include wavelengths in the range of lambda=447-594 nm, for example, lambda=473 nm, lambda=488 nm, lambda=514 nm, lambda=532 nm, and lambda=561 nm.

Methods of the invention allow for the measurement of action potentials with sub-millisecond temporal resolution. A neuron expressing an Optopatch construct may be exposed to whole-field illumination with pulses of blue light (10 ms, 25 mW/cm$^2$) to stimulate CheRiff, and simultaneous constant illumination with red light (800 W/cm$^2$) to excite fluorescence of the reporter (e.g., Arch D95N or a suitable variant thereof). The fluorescence of the reporter may be imaged at a 1 kHz frame rate. Key parameters include temporal precision with which single spikes can be elicited and recorded, signal-to-noise ratio (SNR) in fluorescence traces, and long-term stability of the reporter signal. Methods provided herein may be found to optimize those parameters. Further discussion may be found in Foust et al., 2010, Action potentials initiate in the axon initial segment and propagate through axon collaterals reliably in cerebellar Purkinje neurons, J. Neurosci 30:6891-6902; and Popovic et al., 2011, The spatio-temporal characteristics of action potential initiation in layer 5 pyramidal neurons: a voltage imaging study, J. Physiol. 589:4167-4187.

In some embodiments, measurements are made using a low-magnification microscope that images a 1.2×3.3 mm field of view with 3.25 μm spatial resolution and 2 ms temporal resolution. In other embodiments, measurements are made using a high-magnification microscope that images a 100 μm field of view with 0.8 μm spatial resolution and 1 ms temporal resolution. A suitable instrument is an inverted fluorescence microscope, similar to the one described in the Supplementary Material to Kralj et al., 2012, Optical recording of action potentials in mammalian neurons using a microbial rhodopsin, Nat. Methods 9:90-95. Briefly, illumination from a red laser 640 nm, 140 mW (Coherent Obis 637-140 LX), is expanded and focused onto the back-focal plane of a 60× oil immersion objective, numerical aperture 1.45 (Olympus 1-U2B616).

Figure 10:
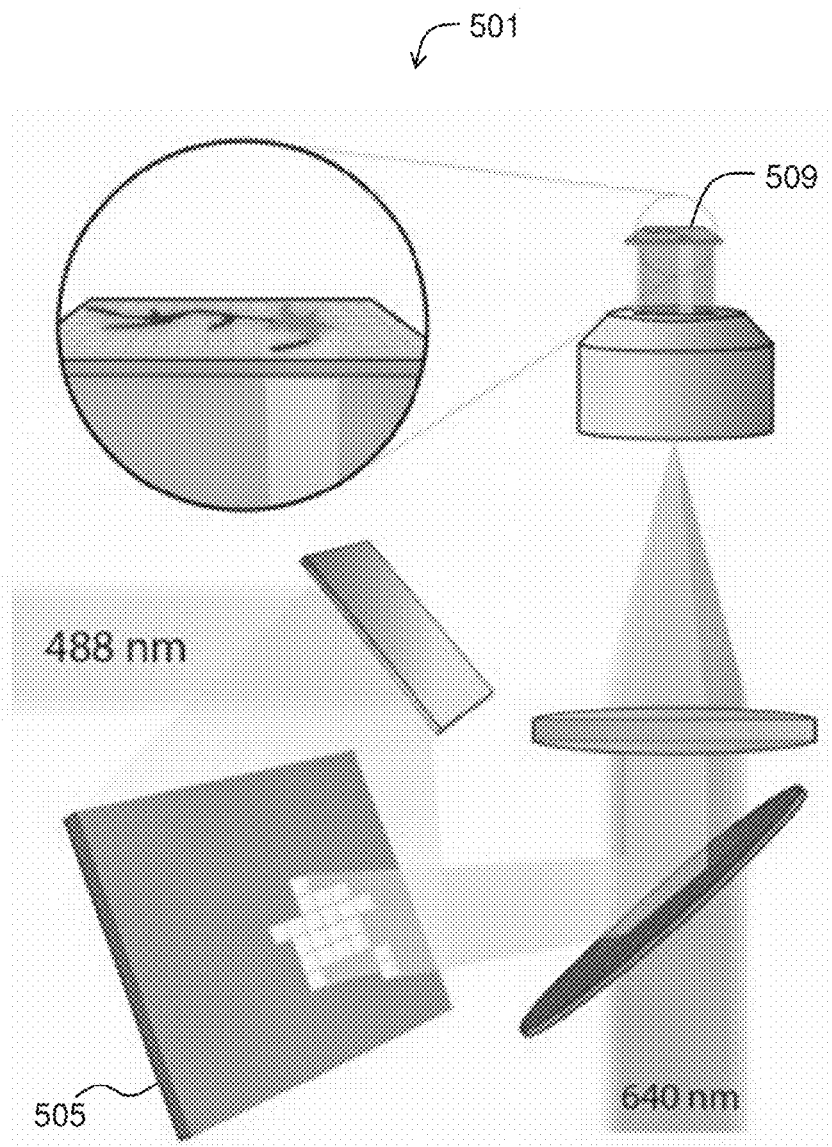
FIG. 10 gives a functional diagram of components of an optical imaging apparatus.

FIG. 10 gives a functional diagram of components of an optical imaging apparatus 501 according to certain embodiments. A 488 nm blue laser beam is modulated in intensity by an acousto-optic modulator (not shown), and then reflected off a digital micromirror device (DMD) 505. The DMD imparted a spatial pattern on the blue laser beam (used for CheRiff excitation) on its way into the microscope. The micromirrors were re-imaged onto the sample 509, leading to an arbitrary user-defined spatiotemporal pattern of illumination at the sample. Simultaneous whole-field illumination with 640 nm red light excites fluorescence of the reporter.

With the inverted fluorescence microscope, illumination from a blue laser 488 nm 50 mW (Omicron PhoxX) is sent through an acousto-optic modulator (AOM; Gooch and Housego 48058-2.5-0.55-5W) for rapid control over the blue intensity. The beam is then expanded and modulated by DMD 505 with 608×684 pixels (Texas Instruments LightCrafter). The DMD is controlled via custom software (Matlab) through a TCP/IP protocol. The DMD chip is re-imaged through the objective onto the sample, with the blue and red beams merging via a dichroic mirror. Each pixel of the DMD corresponds to 0.65 μm in the sample plane. A 532 nm laser is combined with the red and blue beams for imaging of mOrange2. Software is written to map DMD coordinates to camera coordinates, enabling precise optical targeting of any point in the sample.

To achieve precise optical stimulation of user-defined regions of a neuron, pixels on DMD 505 are mapped to pixels on the camera. The DMD projects an array of dots of known dimensions onto the sample. The camera acquires an image of the fluorescence. Custom software locates the centers of the dots in the image, and creates an affine transformation to map DMD coordinates onto camera pixel coordinates.

A dual-band dichroic filter (Chroma zt532/635rpc) separates reporter (e.g., Arch) from excitation light. A 531/40 nm bandpass filter (Semrock FF01-531/40-25) may be used for eGFP imaging; a 710/100 nm bandpass filter (Chroma, HHQ710/100) for Arch imaging; and a quad-band emission filter (Chroma ZET405/488/532/642m) for mOrange2 imaging and pre-measurement calibrations. A variable-zoom camera lens (Sigma 18-200 mm f/3.5-6.3 II DC) is used to image the sample onto an EMCCD camera (Andor iXon+DU-860), with 128×128 pixels. Images may be first acquired at full resolution (128×128 pixels). Data is then acquired with 2×2 pixel binning to achieve a frame rate of 1,000 frames/s. For runs with infrequent stimulation (once every 5 s), the red illumination is only on from 1 s before stimulation to 50 ms after stimulation to minimize photobleaching. Cumulative red light exposure may be limited to <5 min. per neuron.

Low magnification wide-field imaging is performed with a custom microscope system based around a 2×, NA 0.5 objective (Olympus MVX-2). Illumination is provided by six lasers 640 nm, 500 mW (Dragon Lasers 635M500), combined in three groups of two. Illumination is coupled into the sample using a custom fused silica prism, without passing through the objective. Fluorescence is collected by the objective, passed through an emission filter, and imaged onto a scientific CMOS camera (Hamamatsu Orca Flash 4.0). Blue illumination for channelrhodopsin stimulation is provided by a 473 nm, 1 W laser (Dragon Lasers), modulated in intensity by an AOM and spatially by a DMD (Digital Light Innovations DLi4130–ALP HS). The DMD is re-imaged onto the sample via the 2× objective. During a run, neurons may be imaged using wide-field illumination at 488 nm and eGFP fluorescence. A user may select regions of interest on the image of the neuron, and specify a time course for the illumination in each region. The software maps the user-selected pixels onto DMD coordinates and delivers the illumination instructions to the DMD.

The inverted fluorescence micro-imaging system records optically from numerous (e.g., 50) expressing cells or cell clusters in a single field of view. The system may be used to characterize optically evoked firing patterns and AP waveforms in neurons expressing an Optopatch construct. Each field of view is exposed to whole-field pulses of blue light to evoke activity (e.g., 0.5 s, repeated every 6 s, nine intensities increasing from 0 to 10 mW/cm$^2$). Reporter fluorescence such as from Arch D95N may be simultaneously monitored with whole-field excitation at 640 nm, 100 W/cm$^2$. Additional useful discussion of microscopes and imaging systems may be found in U.S. Pat. No. 8,532,398 to Filkins; U.S. Pat. No. 7,964,853 to Araya; U.S. Pat. No. 7,560,709 to Kimura; U.S. Pat. No. 7,459,333 to Richards; U.S. Pat. No. 6,972,892 to DeSimone; U.S. Pat. No. 6,898,004 to Shimizu; U.S. Pat. No. 6,885,492 to DeSimone; and U.S. Pat. No. 6,243,197 to Schalz, the contents of each of which are incorporated by reference.

Figure 11:
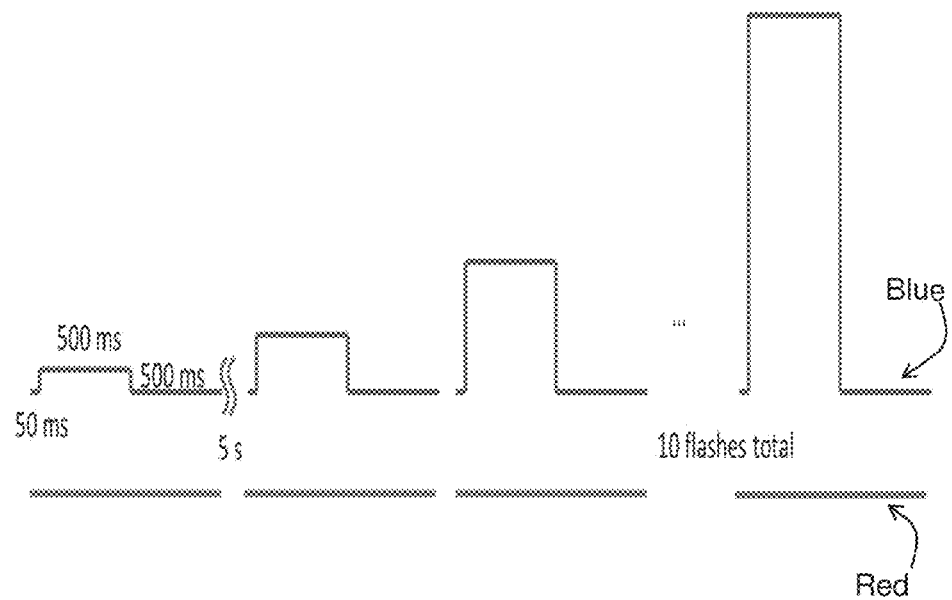
FIG. 11 illustrates a pulse sequence of red and blue light used to record action potentials.

FIG. 11 illustrates a pulse sequence of red and blue light used to record action potentials under increasing optical stimulation. In some embodiments, neurons are imaged on a high resolution microscope with 640 nm laser (600 W/cm$^2$) for voltage imaging. In certain embodiments, neurons are imaged on a high resolution microscope with 640 nm laser (600 W/cm$^2$) for voltage imaging and excited with a 488 nm laser (20-200 mW/cm$^2$). Distinct firing patterns can be observed (e.g., fast adapting and slow-adapting spike trains). System measurements can detect rare electrophysiological phenotypes that might be missed in a manual patch clamp measurement. Specifically, the cells' response to stimulation (e.g., optical actuation) may be observed. Instruments suitable for use or modification for use with methods of the invention are discussed in U.S. Pub. 2013/0170026 to Cohen, incorporated by reference.

Using the described methods, populations of cells may be measured. For example, both diseased and corrected (e.g., by zing finger domains) motor neurons may be measured. A cell's characteristic signature such as a neural response as revealed by a spike train may be observed.

5b. Extracting Fluorescence from Movies

Fluorescence values are extracted from raw movies by any suitable method. One method uses the maximum likelihood pixel weighting algorithm described in Kralj et al., 2012, Optical recording of action potentials in mammalian neurons using a microbial rhodopsin, Nat Methods 9:90-95. Briefly, the fluorescence at each pixel is correlated with the whole-field average fluorescence. Pixels that showed stronger correlation to the mean are preferentially weighted. This algorithm automatically finds the pixels carrying the most information, and de-emphasizes background pixels.

In movies containing multiple cells, fluorescence from each cell is extracted via methods known in the art such as Mukamel et al., 2009, Automated analysis of cellular signals from large-scale calcium imaging data, Neuron 63(6):747-760, or Maruyama et al., 2014, Detecting cells using non-negative matrix factorization on calcium imaging data, Neural Networks 55:11-19. These methods use the spatial and temporal correlation properties of action potential firing events to identify clusters of pixels whose intensities co-vary, and associate such clusters with individual cells.

Alternatively, a user defines a region comprising the cell body and adjacent neurites, and calculates fluorescence from the unweighted mean of pixel values within this region. In low-magnification images, direct averaging and the maximum likelihood pixel weighting approaches may be found to provide optimum signal-to-noise ratios.

6. Signal Processing

6a. Signal Processing with Independent Component Analysis to Associate Signals with Cells An image or movie may contain multiple cells in any given field of view, frame, or image. In images containing multiple neurons, the segmentation is performed semi-automatically using an independent components analysis (ICA) based approach modified from that of Mukamel, et al., 2009, Automated analysis of cellular signals from large-scale calcium imaging data, Neuron 63:747-760. The ICA analysis can isolate the image signal of an individual cell from within an image.

FIG. 12-FIG. 15 illustrate the isolation of individual cells in a field of view. Individual cells are isolated in a field of view using an independent component analysis.

Figure 12:
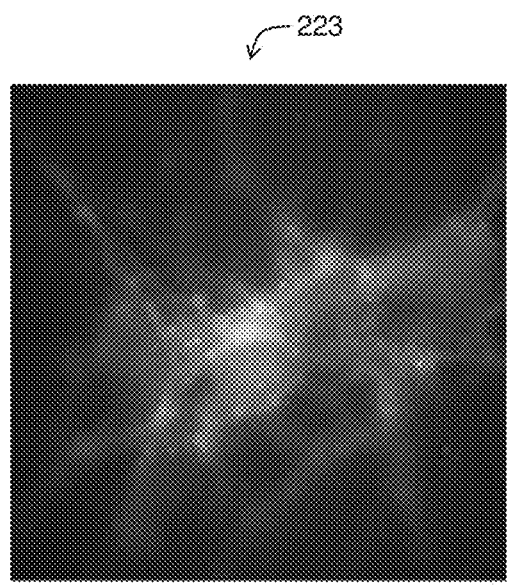
FIG. 12 shows an image that contains five neurons whose images overlap.

FIG. 12 shows an image that contains five neurons whose images overlap with each other. The fluorescence signal at each pixel is an admixture of the signals from each of the neurons underlying that pixel.

Figure 13:
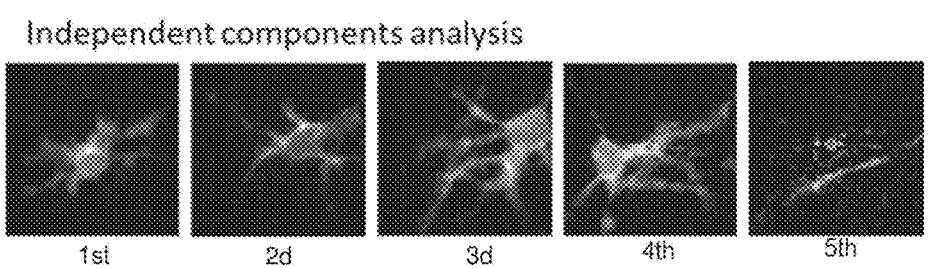
FIG. 13 shows clusters of pixels whose intensity varies synchronously found by an independent component analysis (ICA).

As shown in FIG. 13, the statistical technique of independent components analysis finds clusters of pixels whose intensity is correlated within a cluster, and maximally statistically independent between clusters. These clusters correspond to images of individual cells comprising the aggregate image of FIG. 12.

From the pseudo-inverse of the set of images shown in FIG. 13 are calculated spatial filters with which to extract the fluorescence intensity time-traces for each cell. Filters are created by setting all pixel weights to zero, except for those in one of the image segments. These pixels are assigned the same weight they had in the original ICA spatial filter.

Figure 14:
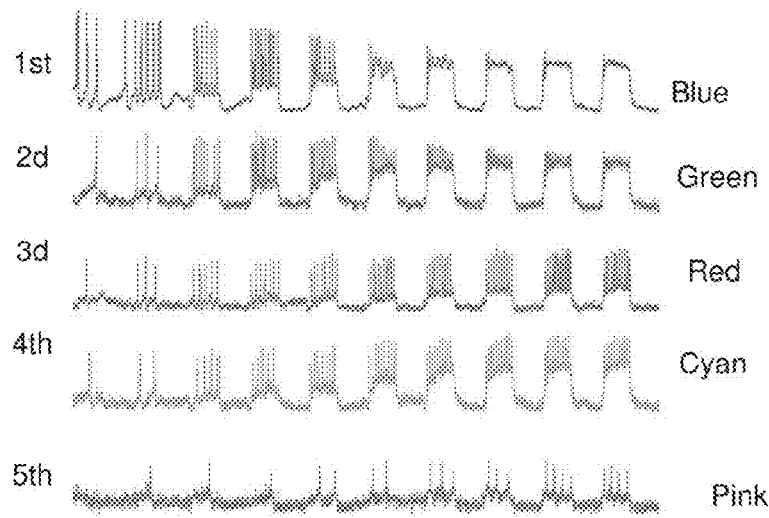
FIG. 14 illustrates contributions from individual cells to the ICA time course.

In FIG. 14, by applying the segmented spatial filters to the movie data, the ICA time course has been broken into distinct contributions from each cell. Segmentation may reveal that the activities of the cells are strongly correlated, as expected for cells found together by ICA. In this case, the spike trains from the image segments are similar but show a progress corresponding to different physiological responses of the cells to the stimulus pattern shown in FIG. 11.

Figure 15:
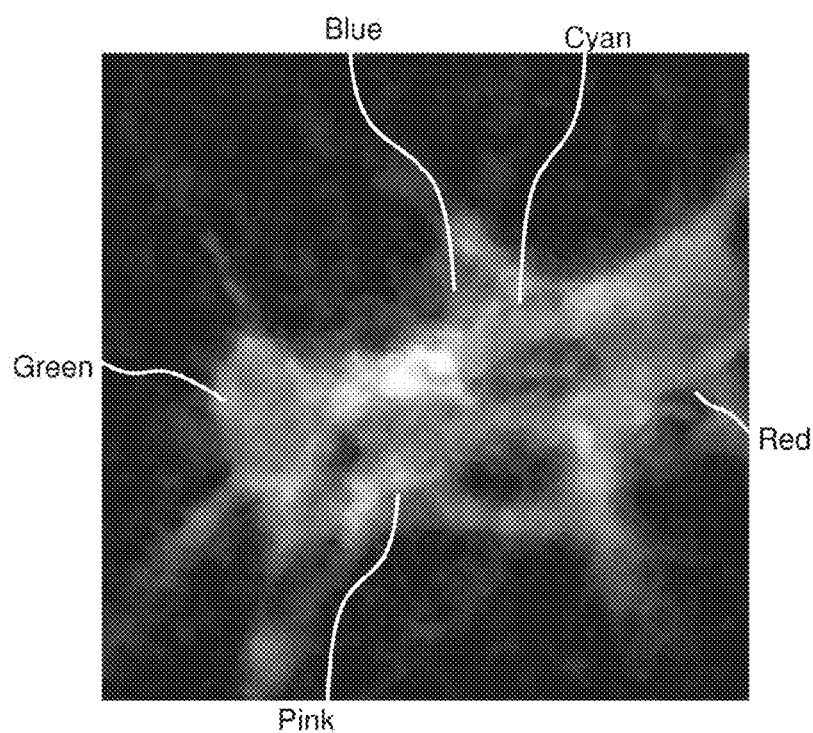
FIG. 15 shows an overlay of filters used to map individual cells in an image.

FIG. 15 shows an overlay of the individual filters used to map (and color code) individual cells from the original image.

6b. Signal Processing Via Sub-Nyquist Action Potential Timing (SNAPT)

For individual cells, the sub-cellular details of action potential propagation can be represented by the timing at which an interpolated action potential crosses a threshold at each pixel in the image. Identifying the wavefront propagation may be aided by first processing the data to remove noise, normalize signals, improve SNR, other pre-processing steps, or combinations thereof. Action potential signals may first be processed by removing photobleaching, subtracting a median filtered trace, and isolating data above a noise threshold. The AP wavefront may then be identified using an algorithm based on sub-Nyquist action potential timing such as an algorithm based on the interpolation approach of Foust, et al., 2010, Action potentials initiate in the axon initial segment and propagate through axon collaterals reliably in cerebellar Purkinje neurons. J. Neurosci 30, 6891-6902 and Popovic et al, 2011, The spatio-temporal characteristics of action potential initiation in layer 5 pyramidal neurons: a voltage imaging study. J. Physiol. 589, 4167-4187.

A sub-Nyquist action potential timing (SNAPT) algorithm highlights subcellular timing differences in AP initiation. For example, the algorithm may be applied for neurons expressing Optopatch 1, containing a voltage reporter such as Arch D95N or a suitable variant thereof and a voltage actuator such as CheRiff. Either the soma or a small dendritic region is stimulated via repeated pulses of blue light. The timing and location of the ensuing APs is monitored.

Figure 16:
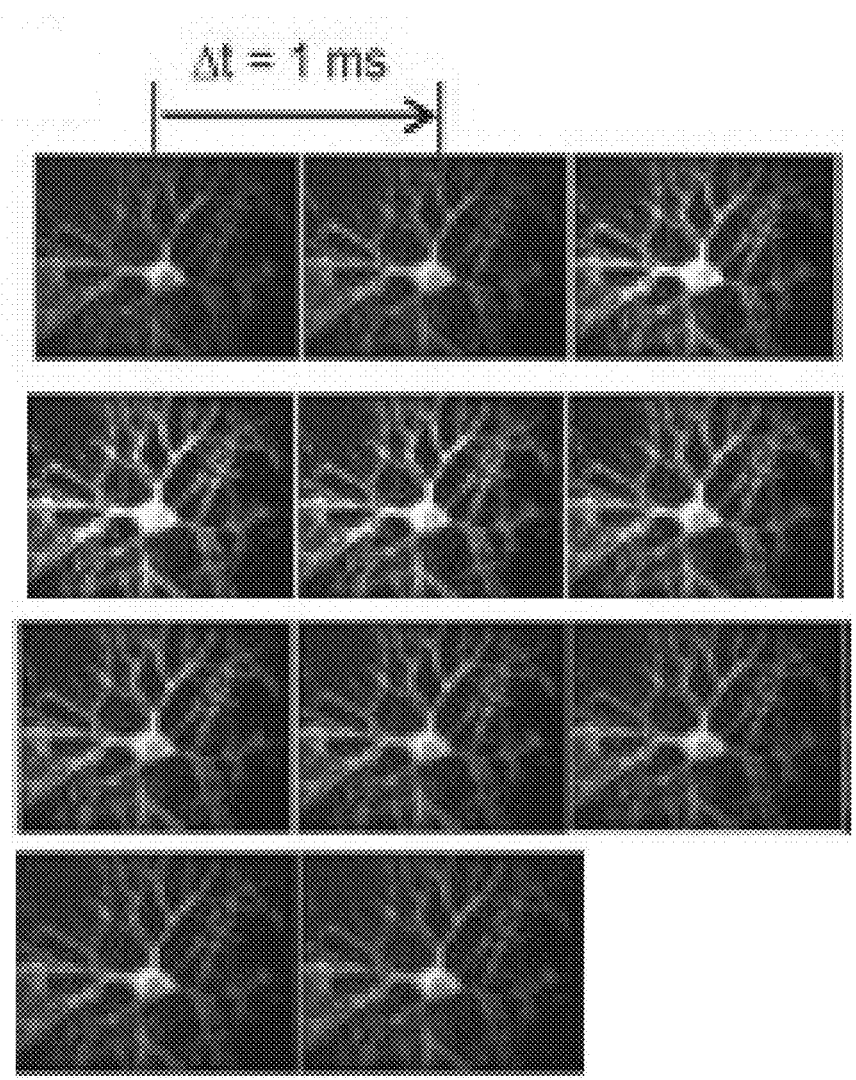
FIG. 16 shows a patterned optical excitation being used to induce action potentials.

FIG. 16 shows a patterned optical excitation being used to induce action potentials. Movies of individual action potentials are acquired (e.g., at 1,000 frames/s), temporally registered, and averaged.

The first step in the temporal registration of spike movies is to determine the spike times. Determination of spike times is performed iteratively. A simple threshold-and-maximum procedure is applied to the whole-field fluorescence trace, F(t), to determine approximate spike times, {T0}. Waveforms in a brief window bracketing each spike are averaged together to produce a preliminary spike kernel $K_0(t)$. A cross-correlation of $K_0(t)$ with the original intensity trace F(t) is calculated. Whereas the timing of maxima in F(t) is subject to errors from single-frame noise, the peaks in the cross-correlation, located at times {T}, are a robust measure of spike timing. A movie showing the mean AP propagation may be constructed by averaging movies in brief windows bracketing spike times {T}. Typically 100-300 APs are included in this average. The AP movie has high signal-to-noise ratio. A reference movie of an action potential is thus created by averaging the temporally registered movies (e.g., hundreds of movies) of single APs.

Spatial and temporal linear filters may further decrease the noise in AP movie. A spatial filter may include convolution with a Gaussian kernel, typically with a standard deviation of 1 pixel. A temporal filter may be based upon Principal Components Analysis (PCA) of the set of single-pixel time traces. The time trace at each pixel is expressed in the basis of PCA eigenvectors. Typically the first 5 eigenvectors are sufficient to account for >99% of the pixel-to-pixel variability in AP waveforms, and thus the PCA eigen-decomposition is truncated after 5 terms. The remaining eigenvectors represented uncorrelated shot noise.

Figure 17:
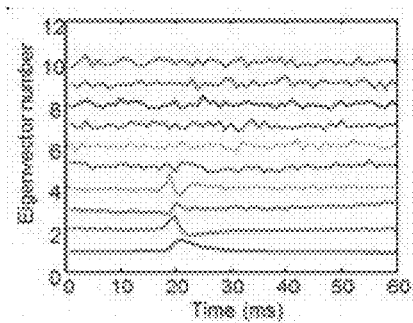
FIG. 17 shows eigenvectors resulting from a principal component analysis of a single action potential waveform.

FIG. 17 shows eigenvectors resulting from a principal component analysis (PCA) smoothing operation performed to address noise. Photobleaching or other such non-specific background fluorescence may be addressed by these means.

Figure 18:
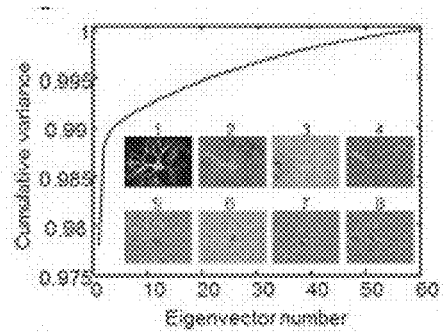
FIG. 18 shows a relation between cumulative variance and eigenvector number for the principal component analysis of FIG. 17.
Figure 19:
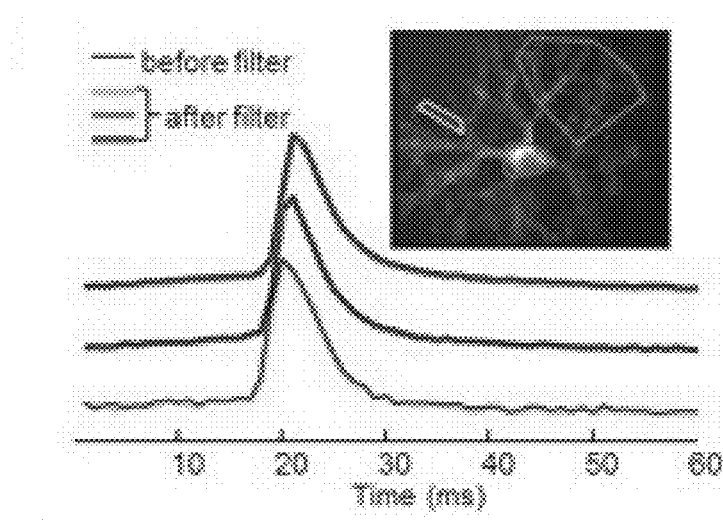
FIG. 19 compares action potential waveforms before and after smoothing operations.

FIG. 18 shows a relation between cumulative variance and eigenvector number. FIG. 19 gives a comparison of action potential waveforms before and after the spatial and PCA smoothing operations.

A smoothly varying spline function may be interpolated between the discretely sampled fluorescence measurements at each pixel in this smoothed reference AP movie. The timing at each pixel with which the interpolated AP crosses a user-selected threshold may be inferred with sub-exposure precision. The user sets a threshold depolarization to track (represented as a fraction of the maximum fluorescence transient), and a sign for dV/dt (indicating rising or falling edge. The filtered data is fit with a quadratic spline interpolation and the time of threshold crossing is calculated for each pixel.

Figure 20:
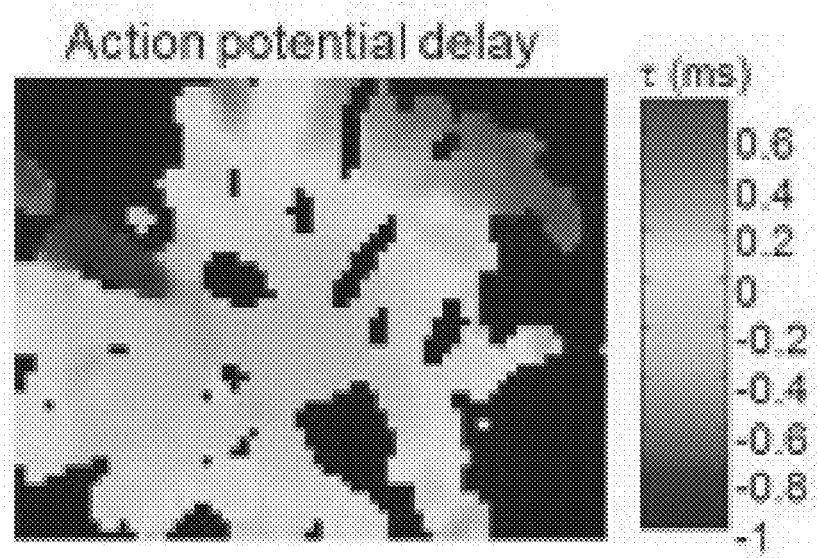
FIG. 20 shows an action potential timing map.

FIG. 20 shows an action potential timing map. The timing map may be converted into a high temporal resolution SNAPT movie by highlighting each pixel in a Gaussian time course centered on the local AP timing. The SNAPT fits are converted into movies showing AP propagation as follows. Each pixel is kept dark except for a brief flash timed to coincide with the timing of the user-selected AP feature at that pixel. The flash followed a Gaussian time-course, with amplitude equal to the local AP amplitude, and duration equal to the cell-average time resolution, a. Frame times in the SNAPT movies are selected to be ~2-fold shorter than a. Converting the timing map into a SNAPT movie is for visualization; propagation information is in the timing map.

Figure 21:
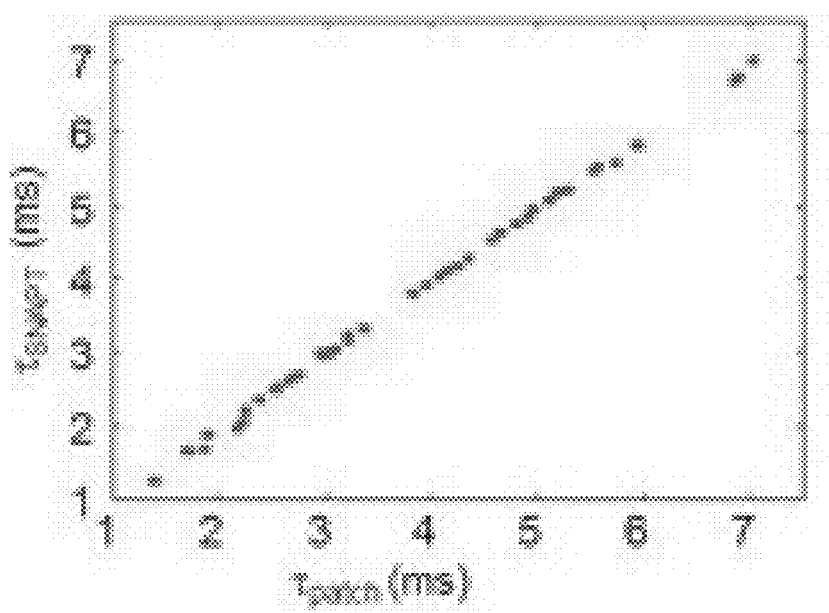
FIG. 21 shows the accuracy of timing extracted by a sub-Nyquist action-potential timing (SNAPT) algorithm.
Figure 22:
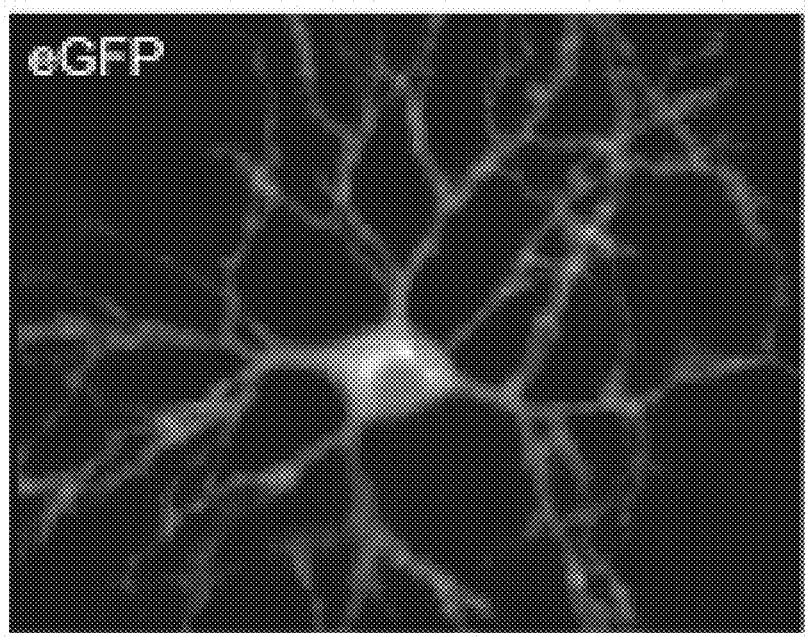
FIG. 22 gives an image of eGFP fluorescence, indicating CheRiff distribution in a neuron.

FIG. 21 shows the accuracy of timing extracted by the SNAPT algorithm for voltage at a soma via comparison to a simultaneous patch clamp recording. FIG. 22 gives an image of eGFP fluorescence, indicating CheRiff distribution.

Figure 23:
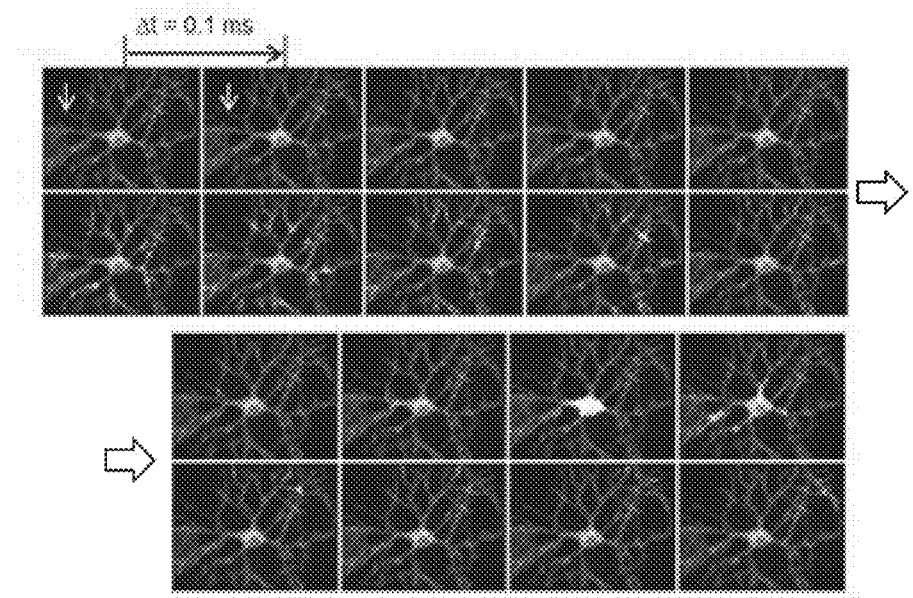
FIG. 23 presents frames from a SNAPT movie.

FIG. 23 presents frames from a SNAPT movie formed by mapping the timing information from FIG. 20 onto a high spatial resolution image from FIG. 22. In FIG. 23, the white arrows mark the zone of action potential initiation in the presumed axon initial segment (AIS). FIGS. 20-23 demonstrate that methods of the invention can provide high resolution spatial and temporal signatures of cells expressing an optical reporter of neural activity.

After acquiring Optopatch data, cells may be fixed and stained for ankyrin-G, a marker of the axon initial segment (AIS). Correlation of the SNAPT movies with the immunostaining images establish that the AP initiated at the distal end of the AIS. The SNAPT technique does not rely on an assumed AP waveform; it is compatible with APs that change shape within or between cells.

The SNAPT movies show AP initiation from the soma in single neurites in measured cells. The described methods are useful to reveal latencies between AP initiation at the AIS and arrival in the soma of 320±220 µs, where AP timing is measured at 50% maximum depolarization on the rising edge. Thus Optopatch can resolve functionally significant subcellular details of AP propagation. Discussion of signal processing may be found in Mukamel et al., 2009, Automated analysis of cellular signals from large-scale calcium imaging data, Neuron 63(6):747-760.

Methods of the invention are used to obtain a signature from the observed cell or cells tending to characterize a physiological parameter of the cell. The measured signature can include any suitable electrophysiology parameter such as, for example, activity at baseline, activity under different stimulus strengths, tonic vs. phasic firing patterns, changes in AP waveform, others, or a combination thereof. Measurements can include different modalities, stimulation protocols, or analysis protocols. Exemplarily modalities for measurement include voltage, calcium, ATP, or combinations thereof. Exemplary stimulation protocols can be employed to measure excitability, to measure synaptic transmission, to test the response to modulatory chemicals, others, and combinations thereof. Methods of invention may employ various analysis protocols to measure: spike frequency under different stimulus types, action potential waveform, spiking patterns, resting potential, spike peak amplitude, others, or combinations thereof.

In certain embodiments, the imaging methods are applied to obtain a signature mean probability of spike for cells from a subject and may also be used to obtain a signature from a control line of cells such as a wild-type control (which may be produced by genome editing as described above so that the control and the wild-type are isogenic but for a single site). The observed signature can be compared to a control signature and a difference between the observed signature and the expected signature corresponds to a characteristic of the cell.

Figure 24:
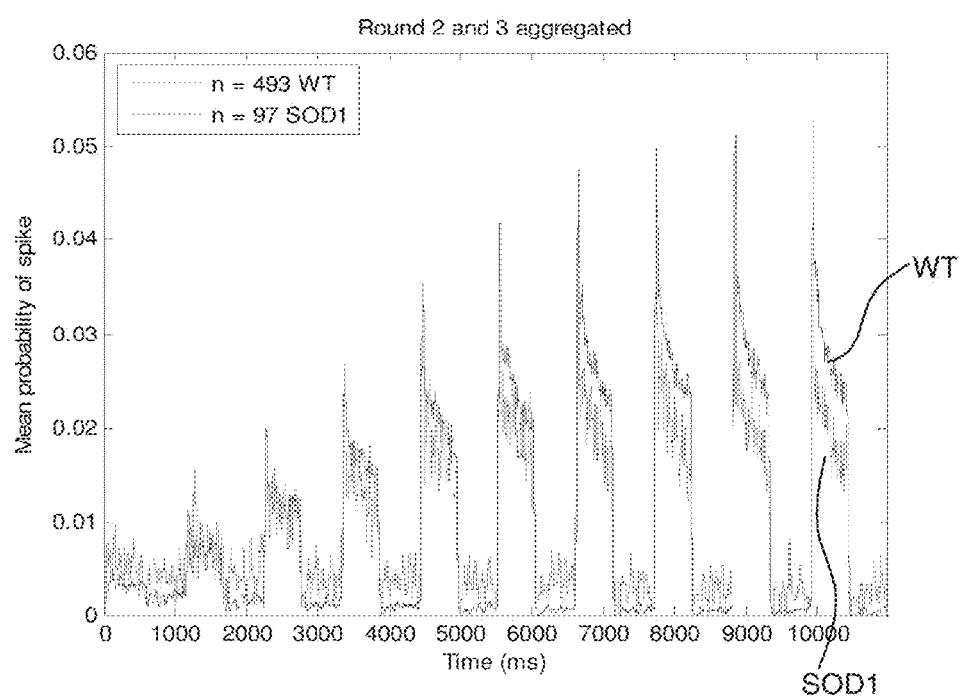
FIG. 24 illustrates an output from measuring action potentials in hiPSC-derived motor neurons containing a mutation associated with amyotrophic lateral sclerosis.

FIG. 24 shows a mean probability of spike of wild-type (WT) and mutant (SOD1 A4V) motor neurons derived from human induced pluripotent stem cells. The SOD1 A4V mutations is associated with amyotrophic lateral sclerosis (ALS). Cellular excitability was measured by probability of spiking during each blue light stimulation, and during no stimulation (spontaneous firing). The mutant neurons had increased rate of firing in the absence of optical stimulation, but a decreased rate of firing under strong optical stimulation.

8. Additional Methods & Applications

Methods of the invention may include the use of tool/test compounds or other interventional tools applied to the observed cell or cells. Application of test compounds can reveal effects of those compounds on cellular electrophysiology. Use of tool compounds can achieve greater specificity in diagnosis or for determining disease mechanisms, e.g. by blocking certain ion channels. By quantifying the impact of the compound, one can quantify the level of that channel in the cell.

With a tool or test compound, a cell may be caused to express an optical reporter of neural or electrical activity and may also be exposed to a compound such as a drug. A signature of the cell can be observed before, during, or after testing the compound. Any combination of different cells and cell types can be exposed to one or any combination of compounds, including different test compound controls. Multi-well plates, multi-locus spotting on slides, or other multi-compartment lab tools can be used to cross-test any combination of compounds and cell types.

In certain embodiments, tool compounds are added to cells and their effect on the cells is observed to distinguish possible diseases or causes or mechanisms of diseases. For example, where two or more cells in synaptic connection with one another are observed, extrinsic stimulation of an upstream cell should manifest as an action potential in a downstream cell. A compound that is known to inhibit neurotransmitter reuptake may be revealed to work on only certain neural subtypes thus indicating a specific disease pattern.

In some embodiments, methods of the invention are used to detect, measure, or evaluate synaptic transmission. A signature may be observed for a cell other than the cell to which direct stimulation was applied. In fact, using the signal processing algorithms discussed herein, synaptic transmission among a plurality of cells may be detected thus revealing patterns of neural connection. Establishing an assay that successfully detects firing of a downstream neuron upon stimulation of an upstream neuron can reveal, where the subject cell to be observed fails to fire upon stimulation of an upstream neuron, a disease or condition characterized by a failure of synaptic transmission.

Test compounds can be evaluated as candidate therapies to determine suitability of a treatment prior to application to a patient. E.g. one can test epilepsy drugs to find the one that reverts the firing pattern back to wild-type. In some embodiments, the invention provides systems and methods for identifying possible therapies for a patient by testing compounds, which systems and methods may be employed as personalized medicine. Due to the nature of the assays described herein, it may be possible to evaluate the effects of candidate therapeutic compounds on a per-patient basis thus providing a tool for truly personalized medicine. For example, an assay as described herein may reveal that a patient suffering from a certain disease has neurons or neural subtypes that exhibit a disease-type physiological phenotype under the assays described herein. One or a number of different compounds may be applied to those neurons or neural subtypes. Cells that are exposed to one of those different compounds (or a combination of compounds) may exhibit a change in physiological phenotype from disease-type to normal. The compound or combination of compounds that affects the change in phenotype from disease-type to normal is thus identified as a candidate treatment compound for that patient.

Provided herein are areas in which an improved optical voltage indicator can be applied both in commercial and scientific endeavors.

Network Effects

Systems and methods of the invention may be used to study and use network effects, e.g. where one set or class of neurons or cardiomyocytes contains the actuator and a different set or class of cells (either intermixed or adjacent) contains the reporter. More specifically, both cell sets might have both actuator and reporter; or one set might have the actuator only, and the other set may have the reporter only. This ability to probe network effects may be particularly important as many genes, such as ones that are being implicated in schizophrenia and bipolar disorder, code for synaptic proteins. See background discussion neural activity in U.S. Pat. No. 8,401,609 to Deisseroth, the contents of which are incorporated by reference.

Network effects also promise to be important in the cardiac area, where for example a monolayer of cardiomyocytes may be illuminated with some cells expressing actuators of the invention while imaged via others expressing the reporters.

Cells of the invention (e.g., neurons, cardiomyocytes, etc.) may be visualized via a microscope of the invention. Those cells may be in electrical or synaptic communication with one another.

Additionally, it is noted that where networks of cells signal, the signals may propagate from cell to cell in a one-to-one, one-to-many, many-to-one, many-to-many schema, or a combination thereof. That is, axon terminals of two or more neurons may be in synaptic communication with dendrites of one or more other neurons. Where a plurality of cells form a network, signal processing described in section 6 above may be employed to discern which individual cells have signaled which, when, and how quickly. Thus systems and methods of the invention may be used to—for example—study, discover, or diagnose a condition affecting a synaptic protein.

In some embodiments, the invention provides a method in which one first set of cells each includes an actuator and a second set of cells each includes an optical reporter. The method includes stimulating the first set of cells and measuring a signal from the optical reporter, thereby evaluating whether cells of the first set of cells transmitted a signal to cells of the second set of cells. Preferably, the actuator is an optical actuator such as CheRiff and stimulating the first set of cells includes illuminating the CheRiff actuator.

Cardiomyocytes

Methods and systems of the invention may be used to characterize cardiac cells. A cell can be obtained and converted into a cardiomyocyte. For example, using methods described herein, fibroblasts may be converted to cardiomyocytes via induced pluripotent stem cells. An optical actuator of electrical activity, an optical reporter of electrical activity, or both may be incorporated into any one or more of cardiomyocytes as described above. As shown in FIGS. 24-30, a signal may be obtained from the optical reporter in response to a stimulation of the cardiomyocytes. By evaluating the signal, the cardiomyocytes are characterized.

Figure 25:
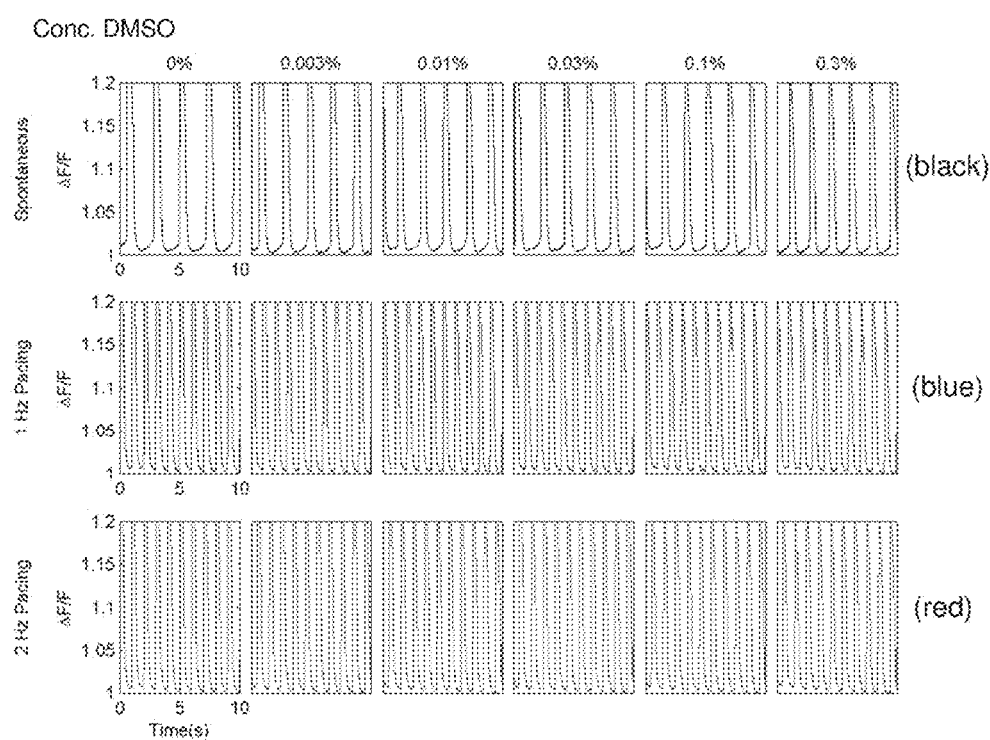
FIG. 25 demonstrates effects of dimethyl sulfoxide (DMSO) on hiPSC-derived cardiomyocytes action potential waveform.

FIG. 25 demonstrates effects of DMSO vehicle control on the action potential (AP) waveforms of hiPSC-derived cardiomyocytes. Representative segments of the mean fluorescence ($\Delta F/F$) versus time (seconds, s) traces at each concentration (0% 'blank', 0.003%, 0.01%, 0.03%, 0.1% and 0.3% DMSO) are shown for spontaneously beating cells (top panel) as well as the same cells optogenetically paced at 1 Hz (middle panel) and 2 Hz (bottom panel). Traces are taken from a single dish of cells and a single field-of-view. Data was taken at 100 Hz frame rate.

Figure 26:
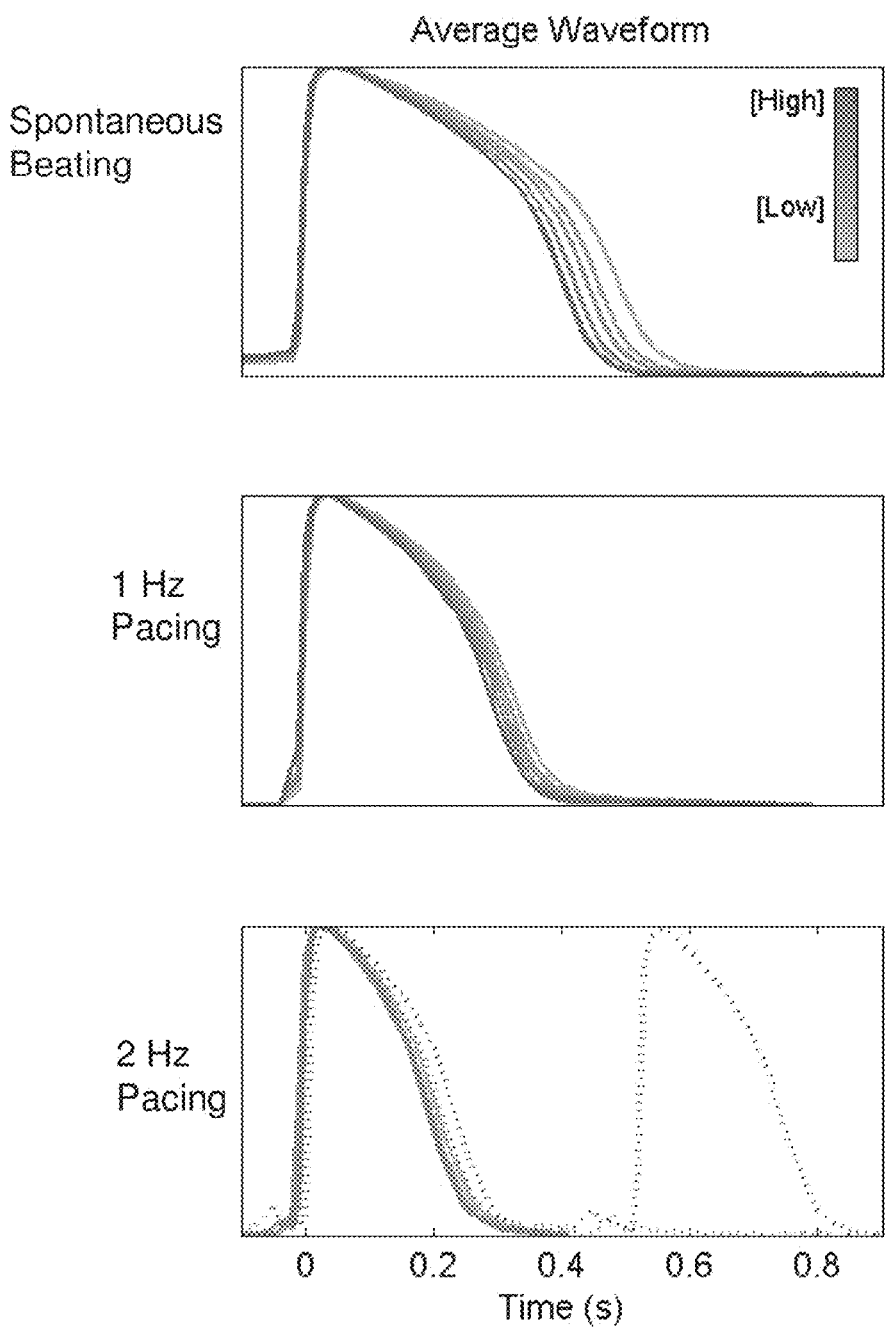
FIG. 26 presents the effects of DMSO control vehicle and pacing rate on the average action potential waveform.

FIG. 26 presents the effects of DMSO control vehicle on the average AP waveform. The average waveform for the range of concentrations tested (cyan to magenta; lowest to highest concentrations tested, respectively) is shown. The top, middle, and bottom panels correspond to spontaneous beating, 1 Hz pacing and 2 Hz pacing, respectively. Dashed lines indicate that the cells did not beat at the specified pacing rate. In the case of spontaneous beating, this criterion did not apply. Panels are calculated from data taken at 100 Hz.

Figure 27:
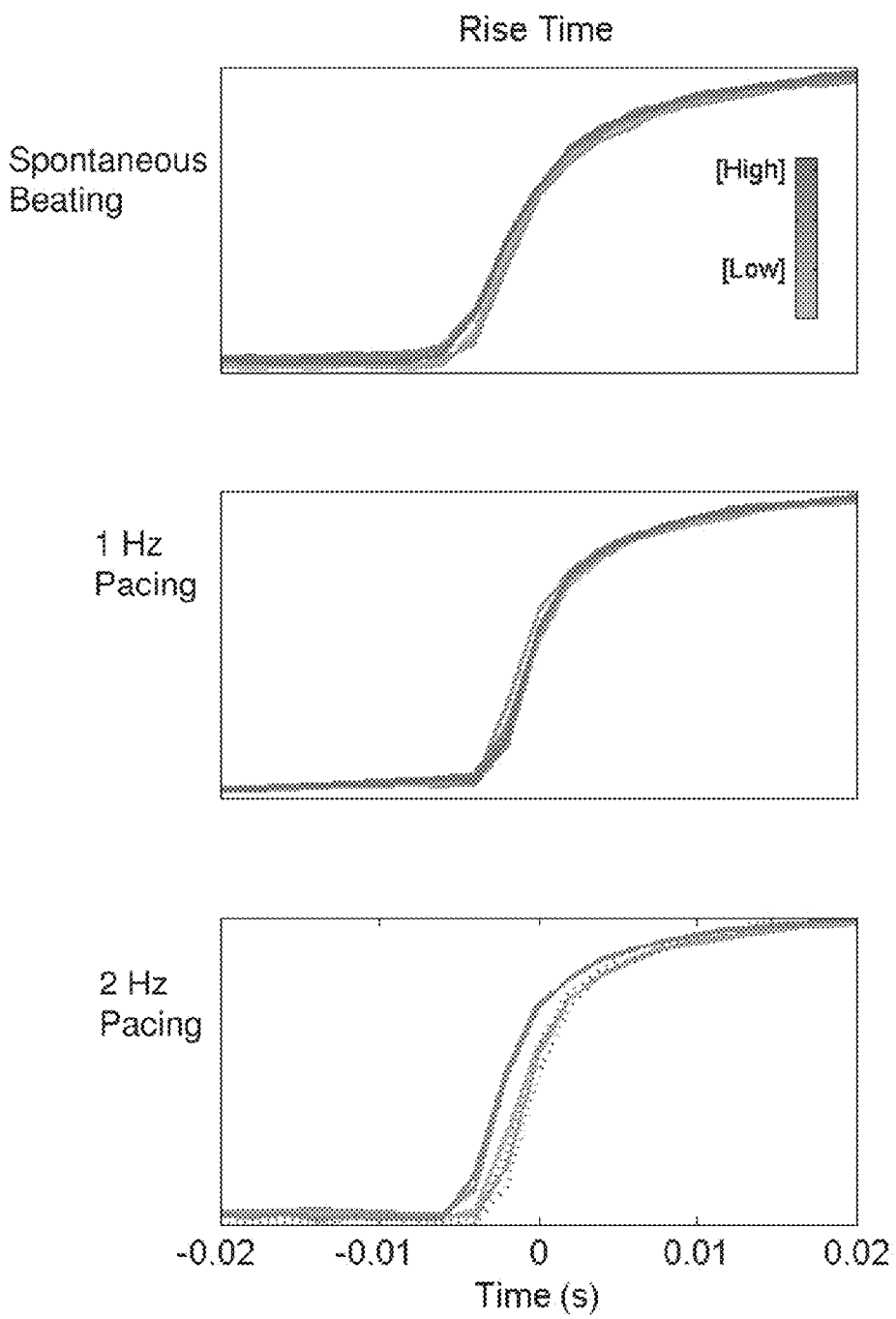
FIG. 27 presents the effects of DMSO control vehicle and pacing rate on the average rise time.

FIG. 27 presents the effects of DMSO control vehicle on the average rise time. The average rise time for the range of concentrations tested (cyan to magenta; lowest to highest concentrations tested, respectively) is shown. The top, middle, and bottom panels correspond to spontaneous beating, 1 Hz pacing and 2 Hz pacing, respectively. Dashed lines indicate that the cells did not beat at the specified pacing rate. In the case of spontaneous beating, this criterion did not apply. Panels are calculated from data taken at 500 Hz.

FIGS. 28-31 illustrate the quantification of the effect of DMSO addition on AP waveform.

Figure 28:
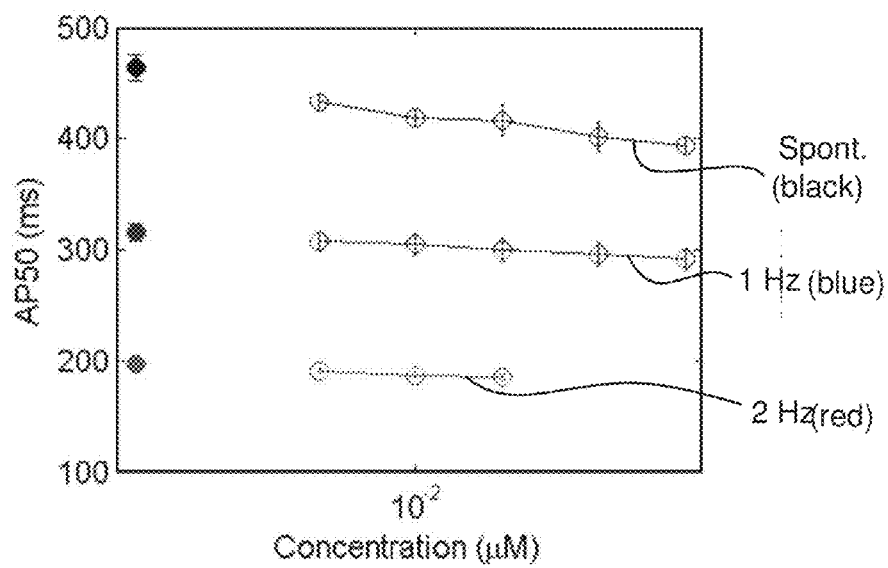
FIG. 28 shows the dose dependent response of action potential width at 50% repolarization (AP50) to increasing concentrations of DMSO.

FIG. 28 shows the dose dependence of the action potential duration at 50% of repolarization (AP50).

Figure 29:
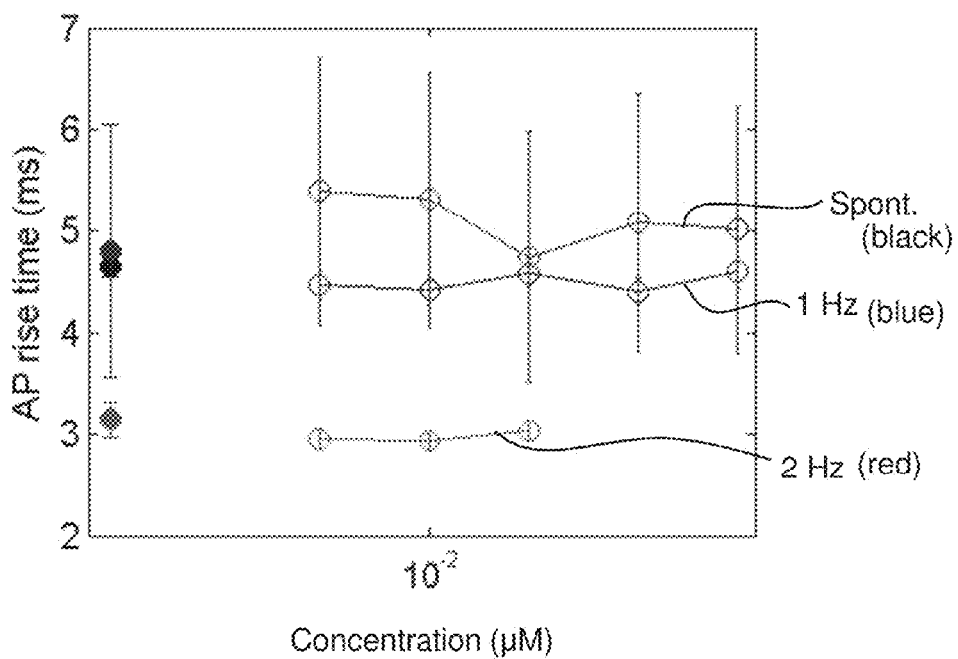
FIG. 29 shows the dose dependent response of action potential rise time to increasing concentrations of DMSO

FIG. 29 shows the dose dependence of the action potential duration at 90% of repolarization (AP90).

Figure 30:
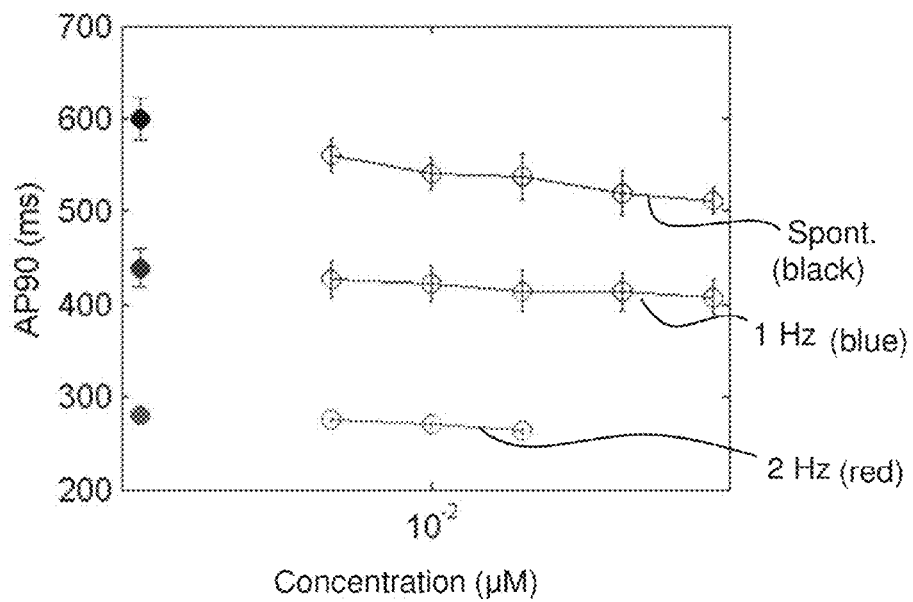
FIG. 30 shows the dose dependent response of action potential width at 90% repolarization (AP90) to increasing concentrations of DMSO.

FIG. 30 shows the dose dependence of the AP rise time.

Figure 31:
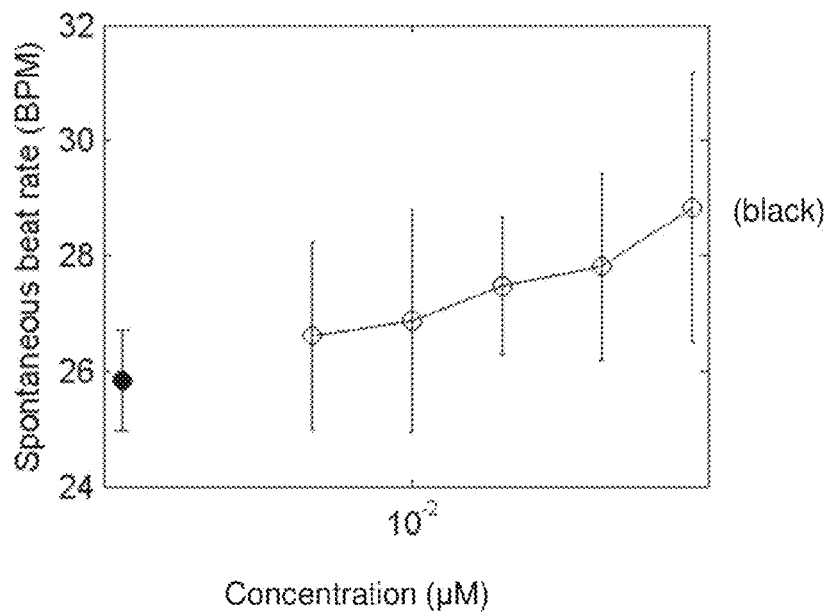
FIG. 31 shows the dose dependence of the spontaneous beat rate as a function of DMSO concentration.

FIG. 31 shows the dose dependence of the spontaneous beat rate.

In FIGS. 28-31, closed circles are used to represent the 'blank' addition of imaging buffer alone whereas open circles are used to represent the addition of compound at varying concentrations. Analysis was performed on fluorescence versus time traces acquired under conditions of spontaneous beating (black) as well as pacing regimens of 1 Hz (blue) and 2 Hz (red). Note that in the case of 1 Hz and 2 Hz pacing, data points are omitted from the plot in the event that the cells do not pace at the specified pace rate. Data points are also omitted in the event that the cells stop beating. Data and error bars are reported as the mean+/−standard error of the mean.

Brain Imaging

The human brain functions by sending electrical impulses along its neurons. These patterns of firing are the origin of human thought and action. The invention potentially provides methods for observing large-scale patterns of electrical activity in an intact brain. (For some background, see Baker et al., 2008, Genetically encoded fluorescent sensors of membrane potential, Brain Cell Biol 36(1-4):53-67.) Use of optical actuators and reporters of the invention may provide unprecedented insights in neuroscience. Methods and device of the invention may allow mapping of brain activity in patients or cells of patients with psychiatric and neurological diseases, and in victims of traumatic injuries or animal models modeling such diseases and injuries.

Optical imaging of neuronal activity can also form the basis for improved brain-machine interfaces for people with disabilities. For imaging in the brain, the optical reporter is administered by direct injection into the site to be analyzed (with or without accompanying electroporation) or the optical reporter is delivered using a viral vector. Alternatively the optical reporter may be administered through the formation of a transgenic organism, or through application of the Cre-Lox recombination system.

Diagnosis

Methods of the invention may be used in the diagnosis of medical conditions.

FIG. 31 illustrates an output from measuring action potentials in cells affected by a mutation and control cells isogenic but for the mutation. The recordings were acquired on motor neurons formed from hiPSCs and expressing the CheRiff voltage actuator and an Arch-based voltage reporter. In the illustrated example, a patient known to have SOD1A4V—a risk factor for amyotrophic lateral sclerosis (ALS)—is studied and the bottom trace is obtained from cells of that patient's genotype. The top trace labeled "WT" refers to cells from that patient that were edited to be SOD1V4A and thus wild-type at the locus of the patient's known mutation but otherwise to provide the genetic context present in the patient. A clinician may diagnosis a neurodegenerative disease based on a signature spike train manifest by the patient's cells. Here, a difference between the signature observed in the patient's cells and the control signature may be correlated to a positive diagnosis of a neurodegenerative disease.

Any suitable method of correlating the patient's signature to a diagnosis may be used. For example, in some embodiments, visual inspection of a signature may be used. In certain embodiments, a computer system may be used to automatically evaluate that an observed signature of the test cells satisfies predetermined criteria for a diagnosis. Any suitable criteria can be used. For example, a computer system may integrate under the spike train for both the test cells and the control cells over a range of time of at least a few seconds and compare a difference between the results. Any suitable difference between the observed and expected signals can be used, for example, the difference may include a modified probability of a voltage spike in response to the stimulation of the cell relative to a control. In certain embodiments (e.g., FIG. 31) the difference between the observed signal and the expected signal comprises a decreased probability of a voltage spike in response to the stimulation of the cell relative to a control and an increased probability of a voltage spike during periods of no stimulation of the cell relative to a control. In one embodiment, systems and methods of the invention detect a decreased probability of a voltage spike in response to the stimulation of the cell relative to a control.

To give one example, a difference of at least 5% can be reported as indicative of an increased risk or diagnosis of a condition. In another example, a computer system can analyze a probability of spike at a certain time point (e.g., 5500 ms) and look for a statistically significant difference. In another example, a computer system can be programmed to first identify a maximal point in the WT spike train (control signature) and then compare a probability at that point in the control signature to a probability in the patient's test signature at the same point and look for a reportable difference (e.g., at least 5% different). One of skill in the art will recognize that any suitable criterion can be used in the comparison of the test signature to the control signature. In certain embodiments, a computer system is trained by machine learning (e.g., numerous instances of known healthy and known diseased are input and a computer system measures an average difference between those or an average signature pattern of a disease signature). Where the computer system stores a signature pattern for a disease phenotype, a diagnosis is supported when the computer system finds a match between the test signature and the control signature (e.g., <5% different or less than 1% different at some point or as integrated over a distance). While obtaining a control signature from a genome-edited cell line from the patient has been discussed, one of skill in the art will recognize that the control signature can be a template or documented control signature stored in computer system of the invention.

In certain embodiments, observation of a signature from a cell is used in a diagnosis strategy in which the observed signature phenotype contributes to arriving at a final diagnosis. For example, with certain disease of the nervous system such as ALS, different neuron types may be affected differently. In some embodiments, a diagnostic method includes comparing different neuron types from the same patient to diagnose a sub-type specific disease.

Microbiology

Methods of the invention may be used in microbiology, for example, to study electrophysiology of microorganisms. Bacteria are host to dozens of ion channels of unknown function (Martinac et al., 2009, Ion channels in microbes, Physiol Rev 88(4):1449). Most bacteria are too small for direct electrophysiological measurements, so their electrical properties are almost entirely unknown. Upon expressing PROPS in *E. coli*, it was found that *E. coli* undergo a previously unknown electrical spiking behavior. The data described herein in the Examples section is the first report of spontaneous electrical spiking in any bacterium. This result establishes the usefulness of voltage sensors in microbes.

Furthermore, studies with PROPS revealed that electrical spiking in *E. coli* is coupled to efflux of a cationic membrane permeable dye. It is thus plausible that electrical spiking is correlated to efflux of other cationic compounds, including antibiotics. Optical voltage indicators may prove useful in screens for inhibitors of antibiotic efflux.

Optical voltage sensors will unlock the electrophysiology of the millions of species of microorganisms which have proven too small to probe via conventional electrophysiology. This information will be useful for understanding the physiology of bacteria with medical, industrial, and ecological applications. Additional discussion may be found in Kralj et al, 2011, Electrical spiking in *Escherichia coli* probed with a fluorescent voltage-indicating protein, Science 333(6040): 345-348.

Mitochondria and Metabolic Diseases

Mitochondria are membrane-bound organelles which act as the ATP factories in eukaryotic cells. A membrane voltage powers the mitochondrial ATP synthase. Dysfunction of mitochondria has been implicated in a variety of neurodegenerative diseases, diabetes, cancer, cardiovascular disease, and aging. Thus there is tremendous interest in measuring mitochondrial membrane potential in vivo, although currently available techniques are severely limited (Verburg & Hollenbeck, 2009, Mitochondrial membrane potential in axons increases with local NGF or semaphoring signaling, Neurosci. 28(33):8306-8315; Ichas et al., 1997, Mitochondria are excitable organelles capable of generating and conveying electrical and calcium signals, *Cell* 89(7):1145-1154.)

The exemplary optical voltage sensor described herein (PROPS) can be tagged with peptide sequences that direct it to the mitochondrial inner membrane (Hoffmann et al., 1994, Photoactive mitochondria: In vivo transfer of a light-driven proton pump into the inner mitochondrial membrane of *Schizosaccharoyces pombe*, PNAS 91:9367-9371) or the mitochondrial outer membrane, where it serves as an optical indicator of mitochondrial membrane potential.

Imaging in Human Cells and Vertebrate Models (e.g., Rat, Mouse, Zebrafish)

An optical reporter such as Arch 3 may be expressed in human embryonic kidney 293 (HEK293T) cells. Fluorescence of Arch 3 in HEK 293T cells was readily imaged in an inverted fluorescence microscope with red illumination ($\lambda$=640 nm, I=540 W/cm$^2$), a high numerical aperture objective, a Cy5 filter set, and an EMCCD camera.

Figure 32:
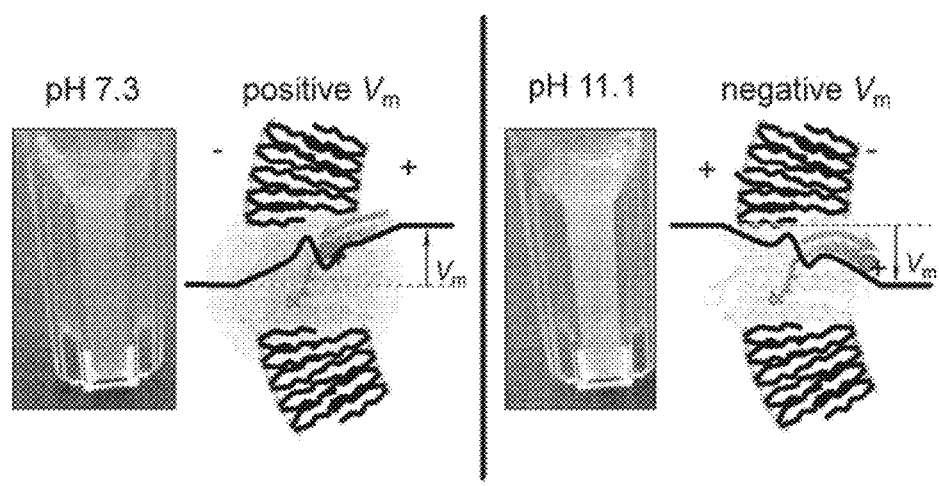
FIG. 32 shows a model of Arch as a voltage sensor.

FIG. 32 shows a model of Arch as a voltage sensor. pH and membrane potential can both alter the protonation of the Schiff base. The crystal structure shown is bacteriorhodopsin; the structure of Arch has not been solved.

Figure 33:
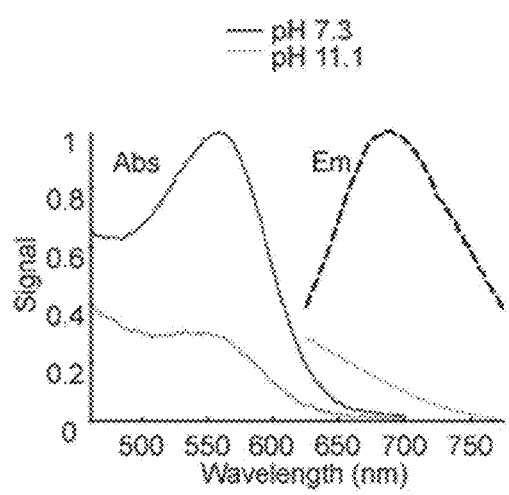
FIG. 33 shows absorption and fluorescence emission spectra.

FIG. 33 shows absorption (solid line) and fluorescence emission (Em, see, dashed line) spectra of purified Arch at neutral and high pH.

Figure 34:
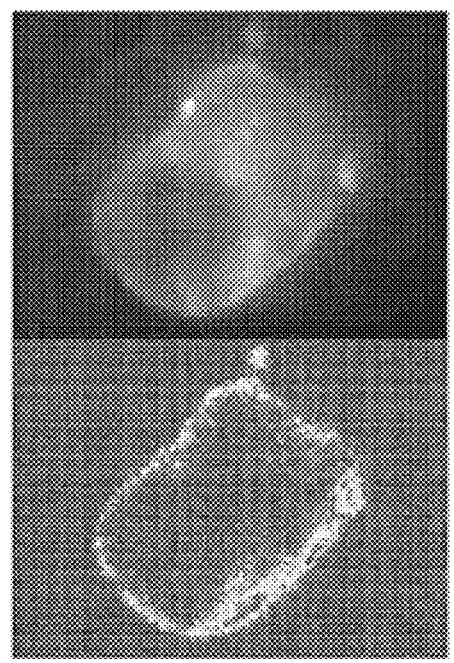
FIG. 34 top shows a HEK cell expressing Arch, visualized via Arch fluorescence.

FIG. 34 top shows a HEK cell expressing Arch, visualized via Arch fluorescence. FIG. 34 bottom shows a pixel-weight matrix regions of voltage-dependent fluorescence. Scale bar 10 µm.

Fluorescence of Arch 3 in HEK 293 cells was readily imaged in an inverted fluorescence microscope with red illumination (lambda=640 nm, I=540 W/cm^2), a high numerical aperture objective, a Cy5 filter set, and an EMCCD camera. The cells exhibited fluorescence predominantly localized to the plasma membrane (FIG. 34). Cells not expressing Arch were not fluorescent. Cells showed 17% photobleaching over a continuous 10-minute exposure, and retained normal morphology during this interval.

The fluorescence of HEK cells expressing Arch was highly sensitive to membrane potential, as determined via whole-cell voltage clamp. We developed an algorithm to combine pixel intensities in a weighted sum such that the output, was a nearly optimal estimate of membrane potential V determined by conventional electrophysiology. FIG. 34 shows an example of a pixel-weight matrix, indicating that the voltage-sensitive protein was localized to the cell membrane; intracellular Arch contributed fluorescence but no voltage-dependent signal.

Figure 35:
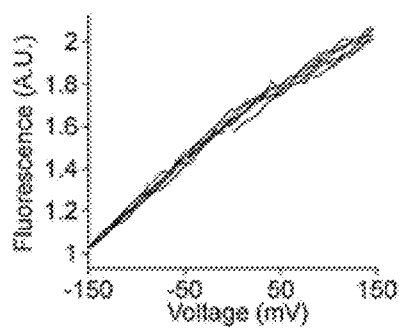
FIG. 35 shows fluorescence of Arch as a function of membrane potential.

FIG. 35 shows fluorescence of Arch as a function of membrane potential. The fluorescence was divided by its value at −150 mV. The fluorescence increased by a factor of 2 between −150 mV and +150 mV, with a nearly linear response throughout this range (FIG. 35). The response of fluorescence to a step in membrane potential occurred within the 500 micro s time resolution of our imaging system on both the rising and falling edge.

Figure 36:
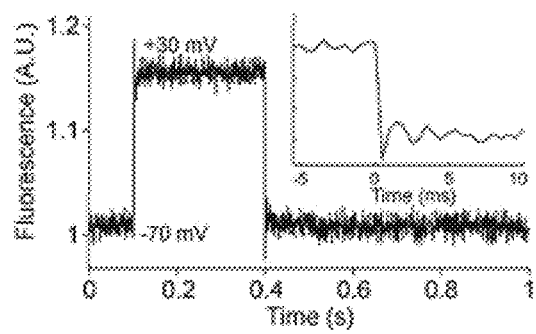
FIG. 36 shows dynamic response of Arch to steps in membrane potential.
Figure 37:
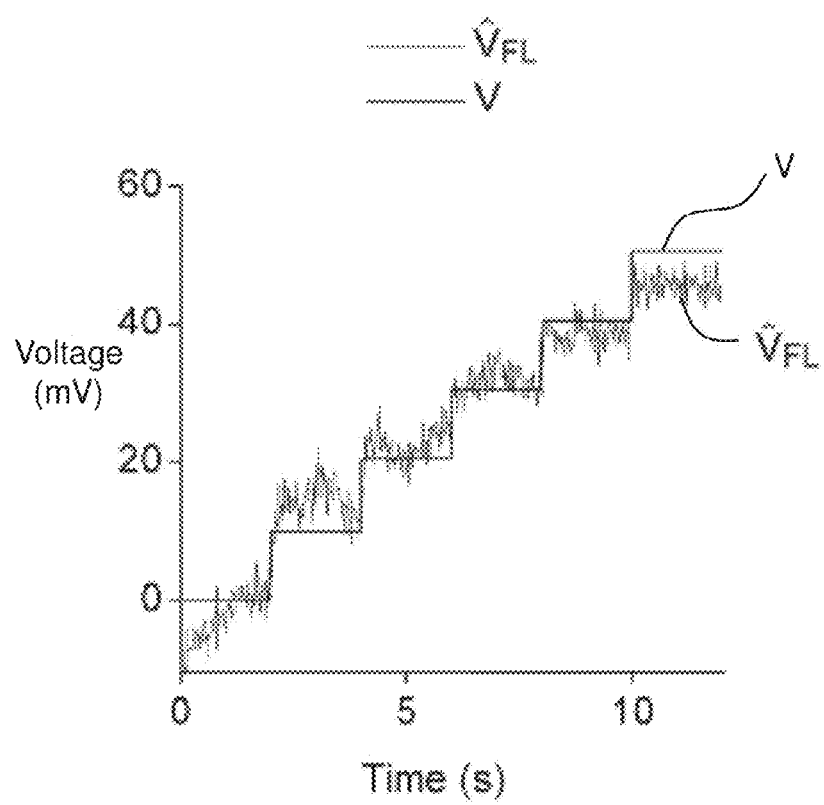
FIG. 37 shows sensitivity of Arch 3 WT to small steps in membrane voltage.
Figure 38:
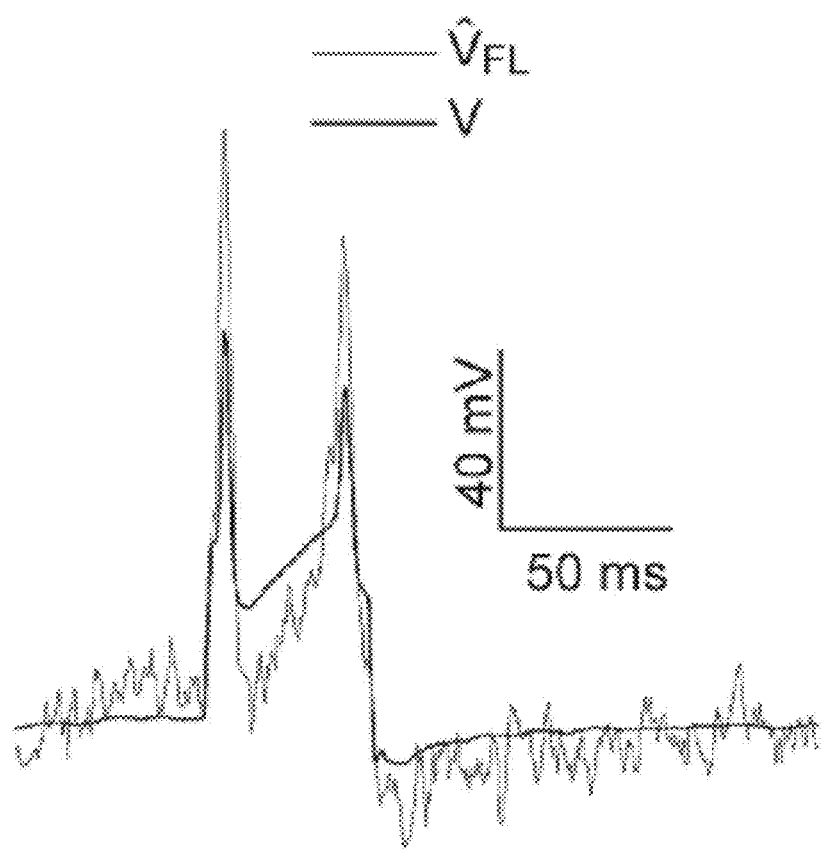
FIG. 38 shows that Arch 3 reports action potentials without exogenous retinal.

FIG. 36 shows dynamic response of Arch to steps in membrane potential between −70 mV and +30 mV. The overshoots on the rising and falling edges were an artifact of electronic compensation circuitry. Data were an average of 20 cycles. Inset shows that step response occurred in less than the 0.5 ms resolution of the imaging system. The cells exhibited fluorescence predominantly localized to the plasma membrane (FIG. 34). Cells not expressing Arch 3 were not fluorescent. Cells showed 17% photobleaching over a continuous 10-minute exposure, and retained normal morphology during this interval. Application of a sinusoidally varying membrane potential led to sinusoidally varying fluorescence; at f=1 kHz, the fluorescence oscillations retained 55% of their low-frequency amplitude (FIG. 37). Arch reported voltage steps as small as 10 mV, with an accuracy of 625 micro V/(Hz)^(½) over timescales<12 s (FIG. 38). Over longer timescales laser power fluctuations and cell motion degraded the accuracy.

FIG. 37 shows sensitivity of Arch 3 WT to voltage steps of 10 mV. Whole-cell membrane potential determined via direct voltage recording, V, (bolded black line, showing step-like line on the graph) and weighted Arch 3 fluorescence, $\hat{V}_{FL}$, (solid narrower line showing serrations on the graph).

FIG. 38 shows that Arch 3 reports action potentials without exogenous retinal. We made an image of 14 day in vitro (DIV) hippocampal neuron imaged via Arch 3 fluorescence with no exogenous retinal. Electrical (bolded solid black line) and fluorescence (non-bolded line, showing serrated line in the graph) records of membrane potential from the neuron during a current pulse. Action potentials are clearly resolved.

Drug Screens

A recent article reported that "Among the 100 top-selling drugs, 15 are ion-channel modulators with a total market value of more than $15 billion." See Molokanova & Savchenko, 2008, Bright future of optical assays for ion channel drug discovery, Drug Discov Today 13:14-22. However, searches for new ion-channel modulators are limited by the absence of good indicators of membrane potential. See Przybylo et al., 2010, Fluorescence techniques for determination of the membrane potentials in high throughput screening, J Fluoresc 20(6):1139-1157. In some embodiments, the optical reporters described herein are used to measure or monitor membrane potential changes in response to a candidate ion channel modulator. Such screening methods can be performed in a high throughput manner by simultaneously screening multiple candidate ion channel modulators in cells.

The constructs disclosed in the present application can be used in methods for drug screening, e.g., for drugs targeting the nervous system. In a culture of cells expressing specific ion channels, one can screen for agonists or antagonists without the labor of applying patch clamp to cells one at a time. In neuronal cultures one can probe the effects of drugs on action potential initiation, propagation, and synaptic transmission. Application in human iPSC-derived neurons will enable studies on genetically determined neurological diseases, as well as studies on the response to environmental stresses (e.g. anoxia).

Similarly, the optical voltage sensing using the constructs provided herein provides a new and much improved method to screen for drugs that modulate the cardiac action potential and its intercellular propagation. These screens will be useful both for determining safety of candidate drugs and to identify new cardiac drug leads. Identifying drugs that interact with the hERG channel is a particularly promising direction because inhibition of hERG is associated with ventricular fibrillation in patients with long QT syndrome. Application in human iPSC-derived cardiomyocytes will enable studies on genetically determined cardiac conditions, as well as studies on the response to environmental stresses (e.g. anoxia).

Additionally, the constructs of the present invention can be used in methods to study development and wound healing. The role of electrical signaling in normal and abnormal development, as well as tissue repair, is poorly understood. Voltage-indicating protein reporters (aka GEVIs) enable studies of voltage dynamics over long times in developing or healing tissues, organs, and organisms, and lead to drugs that modulate these dynamics.

In yet another embodiment, the invention provides methods to screen for drugs that affect membrane potential of mitochondria. Mitochondria play an essential role in ageing, cancer, and neurodegenerative diseases. Currently there is no good probe for mitochondrial membrane potential. Optical reporters provide such a probe, enabling searches for drugs that modulate mitochondrial activity.

Prior to optical reporters, no measurement of membrane potential had been made in any intact prokaryote. The PROPS voltage indicator enabled the discovery that bacteria have complex electrical dynamics. Optical reporters may provide screens for drugs that modulate the electrophysiology of a wide range of medically, industrially, and environmentally significant microorganisms. For instance, we found that electrical activity is correlated with efflux pumping in E. coli.

Changes in membrane potential are also associated with activation of macrophages. However, this process is poorly understood due to the difficulty in applying patch clamp to motile cells. Voltage indicating proteins enable studies of the electrophysiology of macrophages and other motile cells, including sperm cells for fertility studies. Thus the voltage indicating proteins of the invention can be used in methods to screen for drugs or agents that affect, for example, immunity and immune diseases, as well as fertility.

The examples describe expression of voltage indicating proteins in rat hippocampal neurons and human iPSC-derived neurons. In all cell types, single action potentials (APs) were readily observed.

For example, in one embodiment, the invention provides a method wherein the cell expressing a microbial rhodopsin is further exposed to a stimulus capable of or suspected to be capable of changing membrane potential.

Stimuli that can be used include candidate agents, such as drug candidates, small organic and inorganic molecules, larger organic molecules and libraries of molecules and any combinations thereof. One can also use a combination of a known drug, such as an antibiotic with a candidate agent to screen for agents that may increase the effectiveness of the one or more of the existing drugs, such as antibiotics.

The methods of the invention are also useful for vitro toxicity screening and drug development. For example, using the methods described herein one can make a human cardiomyocyte from induced pluripotent cells that stably expresses a modified Archaerhodopsin wherein the proton pumping activity is substantially reduced or abolished. Such cells are particularly useful for in vitro toxicity screening in drug development.

Multimodal Sensing/Multiplexing

Membrane potential is only one of several mechanisms of signaling within cells. One may correlate changes in membrane potential with changes in concentration of other species, such as Ca++, H+ (i.e. pH), Na+, ATP, cAMP. We constructed fusions of Arch with pHluorin (a fluorescent pH indicator) and GCaMP6f (a fluorescent Ca++ indicator). One can also use fusions with other protein-based fluorescent indicators to enable other forms of multimodal imaging using the concept as taught herein. Concentration of ions such as sodium, potassium, chloride, and calcium can be simultaneously measured when the nucleic acid encoding the microbial rhodopsin is operably linked to or fused with an additional fluorescent ion sensitive indicator.

Additional fluorescent proteins may be included. The term "additional fluorescent molecule" refers to fluorescent proteins other than microbial rhodopsins. Such molecules may include, e.g., green fluorescent proteins and their homologs.

Fluorescent proteins that are not microbial rhodopsins are well known and commonly used, and examples can be found, e.g., in a review Wachter, 2006, The Family of GFP-Like Proteins: Structure, Function, Photophysics and Biosensor Applications. Introduction and Perspective, Photochem and Photobiol 82(2):339-344. Also, Shaner et al., 2005, A guide to choosing fluorescent proteins, Nat Meth 2:905-909 provides examples of additional useful fluorescent proteins.

One can combine imaging of voltage indicating proteins with other structural and functional imaging, of e.g. pH, calcium, or ATP. One may also combine imaging of voltage indicating proteins with optogenetic control of membrane potential using e.g. channelrhodopsin, halorhodopsin, and Archaerhodopsin. If optical measurement and control are combined in a feedback loop, one can perform all-optical patch clamp to probe the dynamic electrical response of any membrane.

The invention provides high-throughput methods of characterizing cells. Robotics and custom software may be used for screening large libraries or large numbers of conditions which are typically encountered in high throughput drug screening methods.

Measurement Methodologies

The spectroscopic states of microbial rhodopsins are typically classified by their absorption spectrum. However, in some cases there is insufficient protein in a single cell to detect spectral shifts via absorbance alone. Any of the following several optical imaging techniques can be used to probe other state-dependent spectroscopic properties.

a) Fluorescence

It was found that many microbial rhodopsin proteins and their mutants produce measurable fluorescence. For example, fluorescence of an Arch-based reporter may be excited by light with a wavelength between wavelength of 500 and 650 nm, and emission is peaked at 710 nm. The rate of photobleaching of the reporter decreases at longer excitation wavelengths, so one preferable excitation wavelength is in the red portion of the spectrum, near 633 nm. These wavelengths are further to the red than the excitation and emission wavelengths of any other fluorescent protein, a highly desirable property for in vivo imaging. Preferably, the fluorescence of the reporter shows negligible photobleaching, in stark contrast to all other known fluorophores. When excited at 633 nm, the reporter and GFP emit a comparable numbers of photons prior to photobleaching. Thus microbial rhodopsins constitute a new class of highly photostable, membrane-bound fluorescent markers. It may be found that fluorescence of the reporter is sensitive to the state of protonation of the Schiff base in that the protonated form preferentially fluoresces. Thus voltage-induced changes in protonation enhance changes in fluorescence. In some embodiments, the fluorescence of the reporter is detected using e.g., a fluorescent microscope, a fluorescent plate reader, FACS sorting of fluorescent cells, etc.

b) Electrochromic Fluorescence Resonance Energy Transfer (eFRET)

FRET is a useful tool to quantify molecular dynamics in biophysics and biochemistry, such as protein-protein interactions, protein-DNA interactions, and protein conformational changes. For monitoring the complex formation between two molecules (e.g., retinal and microbial rhodopsin), one of them is labeled with a donor and the other with an acceptor, and these fluorophore-labeled molecules are mixed. When they are dissociated, the donor emission is detected upon the donor excitation. On the other hand, when the donor and acceptor are in proximity (1-10 nm) due to the interaction of the two molecules, the acceptor emission is predominantly observed because of the intermolecular FRET from the donor to the acceptor.

A fluorescent molecule appended to a microbial rhodopsin can transfer its excitation energy to the retinal, but only if the absorption spectrum of the retinal overlaps with the emission spectrum of the fluorophore. Changes in the absorption spectrum of the retinal lead to changes in the fluorescence brightness of the fluorophore. To perform electrochromic FRET, a fluorescent protein is fused with the microbial rhodopsin voltage sensor, and the fluorescence of the protein is monitored. This approach has the advantage over direct fluorescence that the emission of fluorescent proteins is far brighter than that of retinal, but the disadvantage of being an indirect readout, with smaller fractional changes in fluorescence.

In some embodiments, voltage-induced changes in the absorption spectrum of microbial rhodopsins are detected using electrochromic FRET.

c) Rhodopsin Optical Lock-In Imaging (ROLI)

The absorption spectrum of many of the states of retinal is temporarily changed by a brief pulse of light. In ROLI, periodic pulses of a "pump" beam are delivered to the sample. A second "probe" beam measures the absorbance of the sample at a wavelength at which the pump beam induces a large change in absorbance. Thus the pump beam imprints a periodic modulation on the transmitted intensity of the probe beam. These periodic intensity changes are detected by a lock-in imaging system. In contrast to conventional absorption imaging, ROLI provides retinal-specific contrast. Modulation of the pump at a high frequency allows detection of very small changes in absorbance.

In some embodiments, the voltage-induced changes in the absorption spectrum of a microbial rhodopsin are detected using rhodopsin optical lock-in imaging.

d) Raman

Raman spectroscopy is a technique that can detect vibrational, rotational, and other low-frequency modes in a system. The technique relies on inelastic scattering of monochromatic light (e.g., a visible laser, a near infrared laser or a near ultraviolet laser). The monochromatic light interacts with molecular vibrations, phonons or other excitations in the system, resulting in an energy shift of the laser photons. The shift in energy provides information about the phonon modes in the system.

Retinal in microbial rhodopsin molecules is known to have a strong resonant Raman signal. This signal is dependent on the electrostatic environment around the chromophore, and therefore is sensitive to voltage.

In some embodiments, voltage-induced changes in the Raman spectrum of microbial rhodopsins are detected using Raman microscopy.

e) Second Harmonic Generation (SHG)

Second harmonic generation, also known in the art as "frequency doubling" is a nonlinear optical process, in which photons interacting with a nonlinear material are effectively "combined" to form new photons with twice the energy, and therefore twice the frequency and half the wavelength of the initial photons.

SHG signals have been observed from oriented films of bacteriorhodopsin in cell membranes. SHG is an effective probe of the electrostatic environment around the retinal in optical voltage sensors. Furthermore, SHG imaging involves excitation with infrared light which penetrates deep into tissue. Thus SHG imaging can be used for three-dimensional optical voltage sensing using the optical reporters described herein.

In some embodiments, voltage-induced changes in the second harmonic spectrum of microbial rhodopsins are detected using SHG imaging.

f) Photothermal Imaging

Photothermal imaging senses the change in refractive index in a medium arising from a change in temperature, where the change in temperature is induced by optical absorption. In photothermal imaging, a "pump" beam of light is absorbed by a sample and generates local heating. A second "probe" beam of light, at a wavelength that is not absorbed by the sample, propagates through the sample. Temperature-induced changes in the optical path length are detected by one of several optical configurations, e.g. Schlieren imaging or differential interference contrast (DIC) microscopy.

In some embodiments, photothermal imaging is used to detect voltage-induced changes in the absorption spectrum of a microbial rhodopsin.

Chromophore

In the wild, microbial rhodopsins contain a bound molecule of retinal which serves as the optically active element. These proteins will also bind and fold around many other chromophores with similar structure, and possibly preferable optical properties. Analogues of retinal with locked rings cannot undergo trans-cis isomerization, and therefore have higher fluorescence quantum yields (Brack et al., Picosecond time-resolved adsorption and fluorescence dynamics in the artificial bacteriorhodopsin pigment BR6.11, Biophys. J. 65(2):964-972). Analogues of retinal with electron-withdrawing substituents have a Schiff base with a lower pKa than natural retinal and therefore may be more sensitive to voltage (Sheves et al., 1986, Controlling the pKa of the bacteriorhodopsin Schiff base by use of artificial retinal analogs, PNAS 83(10):3262-3266; Rousso et al., 1995, pKa of the protonated Schiff base and asparatic 85 in the Bacteriorhodopsin binding site is controlled by a specific geometry between the two resdidues, Biochemistry 34(37):12059-12065). Covalent modifications to the retinal molecule may lead to optical voltage sensors with significantly improved optical properties and sensitivity to voltage.

Advantages of the Methods and Compositions Described Herein

Key figures of merit for an optical voltage sensor are its response speed and its sensitivity (fractional change in fluorescence per 100 mV change in membrane potential). FIG. 4 compares these attributes for previous protein-based fluorescent voltage indicators and those contemplated herein. Additional important attributes include the ability to target the indicator to a particular cell type or sub-cellular structure, photostability, and low phototoxicity.

Previous protein-based efforts focused on fusing one or more fluorescent proteins to transmembrane voltage sensing domains. A change in voltage induces a conformational change in the voltage sensing domain, which moves the fluorescent proteins, and changes their fluorescence. The reliance on conformational motion of multiple large protein domains makes these approaches unavoidably slow. Furthermore, the conformational shifts of most voltage sensing domains are small, leading to small changes in fluorescence.

The most sensitive indicators from the VSFP 2.x family have a change in fluorescence of $\Delta F/F=10\%$ per 100 mV. VSFP 2.x proteins respond in approximately 100 milliseconds, far too slow to detect a 1 ms action potential in a neuron (Perron et al., 2009, Second and third generation voltage-sensitive fluorescent proteins for monitoring membrane potential, Front Mol Neurosci 2:5; Mutoh et al., 2009, Spectrally-resolved response properties of the three most advanced FRET based fluorescent protein voltage probes, PLoS One 4:e4555). The SPARC family of voltage sensors has a 1 ms response time, but shows a fluorescence change of <1% per 100 mV (Baker et al., 2007, Three fluorescent protein voltage sensor exhibit low plasma membranse expression in mammalian cells, J. Neurosci. Methods 161(1):32-38; Ataka & Pieribone, 2002, A genetically targetable fluorescent probe of channel gating with rapid kinetics, Biophys J 82(1 Pt 1):509-516). The most sensitive voltage-sensitive fluorescent proteins are the ArcLight proteins, which show a voltage sensitivity of $\Delta F/F=-32\%$ per 100 mV. ArcLight and related probes are described in Jin et al., 2012, Single action potentials and subthreshold electrical events imaged in neurons with a fluorescent protein voltage probe, Neuron 75(5):779-785. However, the ArcLight proteins have a slow response, with half-response times of approximately 100 ms at room temperature. The ASAP1 protein offers the most promising combination of sensitivity and speed, with of $\Delta F/F=-29\%$ per 100 mV and a half-response time of approximately 2 ms. Prior to the present study described herein, two decades of research on fluorescent voltage sensors had not yet yielded a protein that could signal individual neuronal action potentials in vivo.

Some organic dyes show voltage-sensitive fluorescence. These lipophilic molecules incorporate into the cell membrane where voltage leads to shifts in conformation or electronic energy levels and thereby to changes in optical properties. These molecules respond quickly (less than 1 ms, typically), and have sensitivities as large as 34% per 100 mV, but cannot be targeted, are often difficult to deliver, and are highly toxic (Krauthamer et al., 1991, Action potential-induced fluorescence changes resolved with an optical fiber carrying excitation light, J. Fluoresc. 1(4):207-213; Fromherz et al., 2008, ANNINE-6plus, a voltage-sensitive dye with good solubility, strong membrane binding and high sensitivity, Eur Biophys J 37(4):509-514; Sjulso & Miesenbock, 2008, Rational optimization and imaging in vivo of a genetically encoded optical voltage reporter, J Neurosci 28(21): 5582-93), see e.g. U.S. Pat. No. 6,991,910 to Adorante, U.S. Pat. No. 6,107,066 to Tsien; U.S. Pat. No. 5,661,035 to Tsien; and U.S. Pub. 2014/0093907 to Miller). None of these optical voltage sensors employs a microbial rhodopsin protein that is configured to run "backwards" to convert changes in membrane potential into changes in an optically detectable signal.

The approach to optical voltage sensing described herein is different from previous efforts. As described herein a protein is used that has a strong electro-optical coupling in the wild.

Microbial rhodopsins in the wild serve to transduce sunlight into a membrane potential. The optical voltage sensors described herein use this function in reverse, transducing a membrane potential into a readily detectable optical signal. As FIG. 4 shows, suitable microbial rhodopsin voltage sensors are provided.

9. Systems of the Invention

Figure 39:
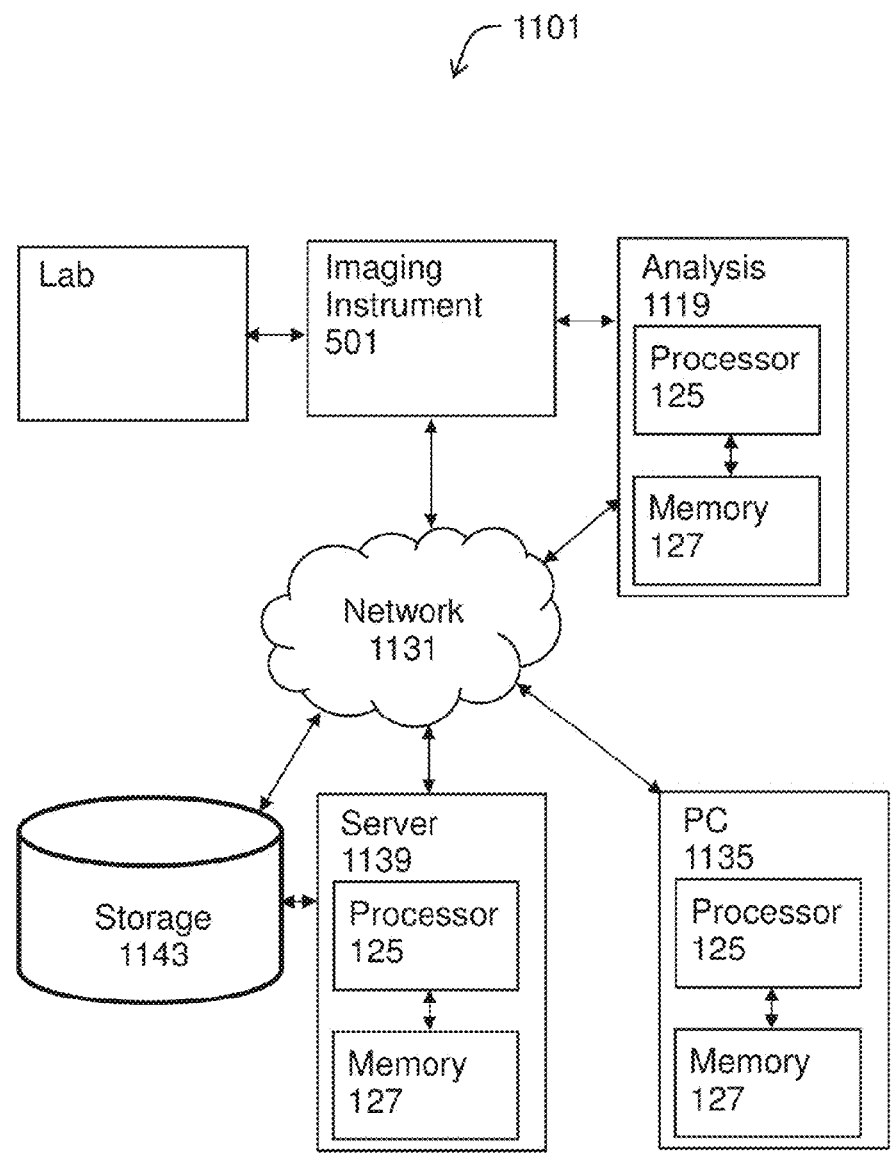
FIG. 39 presents a system useful for performing methods of the invention.

FIG. 39 presents a system 1101 useful for performing methods of the invention. Results from a lab (e.g., transformed, converted patient cells) are loaded into imaging instrument 501. Imaging instrument 501 is operably coupled to an analysis system 1119, which may be a PC computer or other device that includes a processor 125 coupled to a memory 127. A user may access system 1101 via PC 1135, which also includes a processor 125 coupled to a memory 127. Analytical methods described herein may be performed by any one or more processor 125 such as may be in analysis system 1119, PC 1135, or server 1139, which may be provided as part of system 1101. Server 1139 includes a processor 125 coupled to a memory 127 and may also include optional storage system 1143. Any of the computing device of system 1101 may be communicably coupled to one another via network 1131. Any, each, or all of analysis system 1119, PC 1135, and server 1139 will generally be a computer. A computer will generally include a processor 125 coupled to a memory 127 and at least one input/output device.

A processor 125 will generally be a silicon chip microprocessor such as one of the ones sold by Intel or AMD. Memory 127 may refer to any tangible, non-transitory memory or computer readable medium capable of storing data or instructions, which—when executed by a processer 125—cause components of system 1101 to perform methods described herein. Typical input/output devices may include one or more of a monitor, keyboard, mouse, pointing device, network card, Wi-Fi card, cellular modem, modem, disk drive, USB port, others, and combinations thereof. Generally, network 1131 will include hardware such as switches, routers, hubs, cell towers, satellites, landlines, and other hardware such as makes up the Internet.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for characterizing a cell, the method comprising:
   incorporating into an electrically excitable cell an optical actuator of, and an optical reporter of, electrical activity;
   obtaining a signal from the optical reporter in response to a stimulation of the cell; and
   evaluating the signal, thereby characterizing the cell.

2. The method of claim 1, wherein incorporating the actuator and reporter into the cell comprises transforming the electrically active cell with a vector that includes a nucleic acid encoding the optical actuator of, and the optical reporter of, electrical activity.

3. The method of claim 1, further comprising obtaining a somatic cell and converting the somatic cell into the electrically excitable cell.

4. The method of claim 3, wherein converting the somatic cell into the electrically active cell comprises one selected from the list consisting of: direct conversion; and via an iPS intermediary.

5. The method of claim 1 wherein the electrically excitable cell is derived from a human embryonic stem cell.

6. The method of claim 1, wherein the electrically excitable cell is one selected from the list consisting of a neuron, a cardiomyocyte, and a glial cell.

7. The method of claim 1, wherein the optical actuator initiates an action potential in response to the stimulation.

8. The method of claim 7, wherein the stimulation comprises illuminating the cell.

9. The method of claim 8, wherein illuminating the cell is done using spatially resolved light from a digital micromirror array.

10. The method of claim 8, wherein the excitation of, and the signal from, the optical reporter comprise light that does not stimulate the cell.

11. The method of claim 8, further comprising illuminating the cell and obtaining the signal simultaneously.

12. The method of claim 1, wherein the optical actuator comprises a modified rhodopsin.

13. The method of claim 1, wherein the optical actuator comprises CheRiff.

14. The method of claim 1, wherein the optical reporter comprises a rhodopsin that has been modified for voltage-sensitive fluorescence and absence of a steady-state photocurrent.

15. The method of claim 1, wherein the optical reporter comprises Arch D95N.

16. The method of claim 1, further comprising obtaining a control cell and observing a control signal generated by a control optical reporter in the control cell.

17. The method of claim 16, wherein obtaining the control cell comprises editing a genome from the cell such that the control cell and the cell are isogenic but for a mutation.

18. The method of claim 1, wherein obtaining the signal comprises observing a cluster of different cells with a microscope and using a computer to isolate the signal generated by the optical reporter from a plurality of signals from the different cells.

19. The method of claim 18, wherein the computer isolates the signal by performing an independent component analysis and identifying a spike train associated with the cell.

20. The method of claim 19, further comprising using the microscope to obtain an image of a plurality of clusters of cells.

21. The method of claim 1, wherein the observed signal comprises a probability of a voltage spike in response to the stimulation of the cell.

22. The method of claim 1, wherein the observed signal comprises a changed probability of a voltage spike in response to the stimulation of the cell relative to a control.

23. The method of claim 1, wherein the observed signal comprises a change in the waveform of a voltage spike.

24. The method of claim 1, wherein the observed signal comprises a sub-threshold increase in the membrane potential.

25. The method of claim 1, wherein the observed signal comprises a decrease in the membrane potential.

26. The method of claim 1, wherein characterizing the cell comprises diagnosing a disease.

27. The method of claim 26, wherein the disease is selected from the group consisting of Cockayne syndrome, Down Syndrome, Dravet syndrome, familial dysautonomia, Fragile X Syndrome, Friedreich's ataxia, Gaucher disease, hereditary spastic paraplegias, Machado-Joseph disease, Phelan-McDermid syndrome (PMDS), polyglutamine (polyQ)-encoding CAG repeats, spinal muscular atrophy, Timothy syndrome, Alzheimer's disease, frontotemporal lobar degeneration, Huntington's disease, multiple sclerosis, Parkinson's disease, spinal and bulbar muscular atrophy, and amyotrophic lateral sclerosis.

28. The method of claim 1, wherein characterizing the cell comprises evaluating a response of the cell to exposure to a compound.

29. The method of claim 1, wherein characterizing the cell further comprises measuring a concentration of an ion.

30. The method of claim 1, wherein characterizing the cell comprises determining progress of a treatment.

31. The method of claim 1, further comprising editing the genome of the electrically active cells.

32. A method for characterizing an interaction between cells, the method comprising:
incorporating into a first electrically excitable cell an optical actuator of electrical activity incorporating into a second electrically excitable cell an optical reporter of electrical activity;
culturing the first electrically excitable cell and the second electrically excitable cell in proximity to one another;
obtaining a signal from the optical reporter in response to a stimulation of the first electrically excitable cell; and
evaluating the signal, thereby characterizing an interaction between the first electrically excitable cell and the second electrically excitable cell.

33. The method of claim 32, wherein the first electrically excitable cell and the second electrically excitable cell are of the same cell type.

34. The method of claim 33, wherein the cell type is one selected from the list consisting of a neuron, a cardiomyocyte, and a glial cell.

35. The method of claim 32, wherein the first electrically excitable cell and the second electrically excitable cell are each of a different cell type.

36. The method of claim 32, wherein the characterized interaction comprises excitatory neurotransmission.

37. The method of claim 32, wherein the characterized interaction comprises inhibitory neurotransmission.

38. The method of claim 32, wherein characterizing the interaction comprises measurement of conduction velocity of cardiac action potential.

39. The method of claim 32, wherein incorporating the actuator into the first electrically excitable cell comprises transforming first electrically excitable cell with a vector that includes a nucleic acid encoding the optical actuator of electrical activity.

40. The method of claim 32, wherein incorporating the reporter into the second electrically excitable cell comprises transforming the second electrically excitable cell with a vector that includes a nucleic acid encoding the optical reporter of, electrical activity.

41. The method of claim 32, further comprising obtaining somatic cells and converting the somatic cells into the first electrically excitable cell and the second electrically excitable cell.

42. The method of claim 41, wherein converting the somatic cells comprises one selected from the list consisting of: direct conversion; and via an iPS intermediary.

43. The method of claim 32, wherein the first electrically excitable cell and the second electrically excitable cell are derived from a human embryonic stem cell.

44. The method of claim 32, wherein the optical actuator initiates an action potential in response to the stimulation.

45. The method of claim 44, wherein the stimulation comprises illuminating the first electrically excitable cell.

46. The method of claim 45, wherein the illuminating is done using spatially resolved light from a digital micromirror array.

47. The method of claim 45, wherein the excitation of, and the signal from, the optical reporter comprise light that does not stimulate the first electrically excitable cell.

48. The method of claim 47, wherein the illuminating and obtaining the signal are done simultaneously.

49. The method of claim 32, wherein the optical actuator comprises a modified rhodopsin.

50. The method of claim 32, wherein the optical actuator comprises CheRiff.

51. The method of claim 32, wherein the optical reporter comprises a rhodopsin that has been modified for voltage-sensitive fluorescence and absence of a steady-state photocurrent.

52. The method of claim 32, wherein the optical reporter comprises Arch D95N.

53. The method of claim 32, wherein obtaining the signal comprises observing a cluster of different cells with a microscope and using a computer to isolate the signal generated by the optical reporter from a plurality of signals from the different cells.

54. The method of claim 53, wherein the computer isolates the signal by performing an independent component analysis and identifying a spike train associated with the second electrically excitable cell.

55. The method of claim 54, further comprising using the microscope to obtain an image of a plurality of clusters of cells.

56. The method of claim 32, wherein the observed signal comprises a probability of a voltage spike in response to the stimulation of the cell.

57. The method of claim 32, wherein the observed signal comprises a changed probability of a voltage spike in response to the stimulation of the cell relative to a control.

58. The method of claim 32, wherein the observed signal comprises a change in the waveform of a voltage spike.

59. The method of claim 32, wherein the observed signal comprises a sub-threshold increase in the membrane potential.

60. The method of claim 32, wherein the observed signal comprises a decrease in the membrane potential.

61. The method of claim 32, wherein characterizing the interaction comprises diagnosing a disease.

62. The method of claim 32, wherein characterizing the interaction comprises evaluating a cellular response to exposure to a compound.

63. The method of claim 32, wherein characterizing the interaction comprises determining progress of a treatment.

64. The method of claim 32, further comprising editing the genome of the electrically active cells.

* * * * *